United States Patent
Weiss et al.

(10) Patent No.: US 8,697,081 B2
(45) Date of Patent: Apr. 15, 2014

(54) METHOD OF MODULATING NEOVASCULARIZATION

(75) Inventors: Stephen J. Weiss, Ann Arbor, MI (US); Robert G. Rowe, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 654 days.

(21) Appl. No.: 12/420,649

(22) Filed: Apr. 8, 2009

(65) Prior Publication Data

US 2009/0258006 A1 Oct. 15, 2009

Related U.S. Application Data

(60) Provisional application No. 61/043,610, filed on Apr. 9, 2008.

(51) Int. Cl.
*A61K 39/00* (2006.01)

(52) U.S. Cl.
USPC .................. 424/184.1; 424/185.1; 424/190.1; 514/21.3

(58) Field of Classification Search
None
See application file for complete search history.

(56) References Cited

U.S. PATENT DOCUMENTS

| | | | |
|---|---|---|---|
| 4,179,337 | A | 12/1979 | Davis |
| 4,301,144 | A | 11/1981 | Iwashita |
| 4,331,647 | A | 5/1982 | Goldenberg |
| 4,496,689 | A | 1/1985 | Nutter |
| 4,640,835 | A | 2/1987 | Shimizu |
| 4,670,417 | A | 6/1987 | Iwasaki |
| 4,791,192 | A | 12/1988 | Nakagawa |
| 5,877,397 | A | 3/1999 | Lonberg |
| 6,833,373 | B1 | 12/2004 | McKearn |
| 2003/0091556 | A1 | 5/2003 | Ruoslahti |
| 2007/0015708 | A1 | 1/2007 | Rouslahti |
| 2008/0199476 | A1* | 8/2008 | Parry et al. ................ 424/139.1 |
| 2008/0248034 | A1* | 10/2008 | Zhou et al. ................ 424/133.1 |

FOREIGN PATENT DOCUMENTS

| | | |
|---|---|---|
| EP | 0399806 | 11/1990 |
| EP | 1595548 | 11/2005 |
| WO | WO 98/12226 | 3/1998 |
| WO | WO 02/057290 | 7/2002 |
| WO | WO2004007685 | * 1/2004 |
| WO | WO 2006/119897 | 11/2006 |
| WO | WO 2008/130635 | 10/2008 |

OTHER PUBLICATIONS

Aziz Rehman., Fibronectin Matrix Assembly: Effects of Thrombospondin on Formation of FITC-70-kDa Fragment Linear Arrays and FITC-FN Fibrils University of Wisconsin-Madison, Center for Biology Education, Program History: 2002, pp. 97-101.*

Dings et al. Discovery and development of anti-angiogenic peptides: A structural link. Angiogenesis 6: 83-91, 2003.*
Fogarty M. Learning from angiogenesis trial failures. The Scientist. Mar. 18, 2002, 16:33-35.*
Adams et al., *Nat. Rev. Mol. Cell Biol.*, 8:464-478 (2007).
Aebi et al., *Nature*, 323:560-564 (1986.).
Ambesi et al., *Cancer Res.*, 65(1):148-156 (2005).
Baneyx et al., *Proc. Natl. Acad. Sci. USA*, 99(8):5139-5143 (2002).
Ben-Ze'evl et al, *Cell*, 21, 365-372.
Benecke, et al., *Cell*, 14, 931-939 (1978).
Bershadsky et al., *Curr. Opin. Cell Biol.*, 18(5):472-481 (2006).
Bouroulous et al., *J. Cell Biol.*, 143(1):267-276 (1998).
Chen et al., *Science*, 276:1425-1428 (1997).
Chernousov et al., *J. Biol. Chem.*, 266(17):10851-10858 (1991).
Chernousov et al., *FEBS Lett.*, 217(1): 124-8 (1987).
Chun et al., *Cell*, 125, 577-591 (2006).
Chun et al., *J. Cell Biol.*, 167, 757-767 (2004).
Clark et al., *J. Exp. Med.*, 156(2):646-651 (1982).
Cohen et al., *Development*, 134, 1385-1395 (2007).
Columbaro et al., *Cell Mol. Life Sci.*, 62:2669-2678 (2005).
Corbett et al., *J. Biol. Chem.*, 274 (30): 20943-20948 (1999).
Corson et al., *Development*, 130(19):4527-4527 (2003).
Crisp et al., *FEBS Lett.*, 582:2023-2032 (2008).
Crisp et al., *J. Cell Biol.*, 172:41-53 (2005).
Csoka et al., *Aging Cell*, 3:235-243 (2004).
Dahl et al., *Circ. Res.*, 102 :1307-1318 (2008).
Dechat et al., *Genes Dev.*, 22:832-853 (2008).
Dillon, *Dev. Cell*, 15:182-186 (2008).
Discher et al., *Science*, 310:1139-1143 (2005).
Ehrbar et al., *Biomacromolecules*, 8:3000-3007 (2007).
Eliceiri et al., *J. Cell Biol.*, 140(5):1255-1263 (1998).
Engler et al., *Cell*, 126:677-689 (2006).
Even-Ram et al., *Nat. Cell Bio.*, 9 (3):299-309 (2007).
Finlan et al., *PLoS Genet*, 4, e1000039 (2008).
Folkman et al., *Nature*, 273, 345-349 (1978).

(Continued)

*Primary Examiner* — Maher Haddad
(74) *Attorney, Agent, or Firm* — Marshall, Gerstein & Borun LLP

(57) ABSTRACT

The invention provides a method of inhibiting neovascularization in a subject. The method comprises administering to the subject an agent that interferes with fibronectin (Fn) matrix assembly in an amount effective to inhibit neovascularization. The invention also provides a method of identifying an agent that inhibits neovascularization. The method comprises detecting fibronectin (Fn) matrix assembly by stimulated endothelial cells cultured in three-dimensional culture gel in the presence and absence of an agent. A decrease in Fn matrix assembly in the presence of the agent compared to Fn matrix assembly in the absence of the agent is indicative of an agent that inhibits neovascularization. Alternatively, the method of identifying an agent that inhibits neovascularization comprises detecting changes in nuclear architecture in stimulated endothelial cells cultured in three-dimensional culture gel in the presence and absence of an agent. A reduction in nuclear architecture organization identifies an agent that inhibits neovascularization.

3 Claims, No Drawings

(56) References Cited

OTHER PUBLICATIONS

Fotsis et al., *J. Nutr.*, 125:790S-797S (1995).
Frank et al., *Microsurgery*, 15(6):399-404 (1994).
Geiger et al., *Nat. Rev. Mol. Cell Biol.*, 2(11):793-805 (2001).
Gerace et al., *J. Cell Sci. Suppl.*, 1:137-60 (1984).
Glynn et al., *Hum. Mol. Genet.*, 14, 2959-2969 (2005).
Goldman et al., *Proc. Nat. Acad. Sci. USA*, 101, 8963-8968 (2004).
Haas et al., *Arthritis Rheum.*, 56(8):2535-48 (2007).
Haberland et al., *Nat. Rev. Genet.*, 10, 32-42 (2009).
Hathout et al., *Transpl. Int.*, 20(12):1059-1065 (2007).
Hawryluk-Gara et al., *Mol. Biol. Cell*, 16:2382-2394 (2005).
Hiraoka et al., *Cell*, 95:365-377 (1998).
Holaska et al., *Circ. Res.*, 103:16-23 (2008).
Holmbeck et al., *Cell*, 99: 81-92 (1999).
Hotary et al., *Cell*, 114(1):33-45 (2003).
Hoang et al., *Proc. Natl. Acad. Sci. USA*, 101(7):1874-1879 (2004).
Huang et al., *Mol. Biol. Cell.*, 9, 3179-3193 (1998).
Ingber, *FASEB J.*, 20(7):811-827 (2006).
Ingber, *Proc. Natl. Acad. Sci. USA*, 87:3579-3583 (1990).
Iruela-Arispe et al., *Dev. Cell*, 16:222-231 (2009).
Ishimura et al., *Development*, 133:3919-3928 (2006).
Jönsson et al., *Eur. J. Biochem.*, 2002:1041-1048 (1991).
Joh et al., *Matrix Biol.*, 18:211-23 (1999).
Korff et al., *J. Cell Biol.*, 143(5):1341-1352 (1998).
Lamond et al., *Nat. Rev. Mol. Cell Biol.*, 4:605-612 (2003).
Larsen et al., *Curr. Opin. Cell Biol.*, 18(5):463-471 (2006).
Lee et al., *Cancer Chemother. Pharmacol.*, 57(6):761-71 (2006).
Lindgren et al., *Eur. J. Biochem.*, 214:819-827 (1993).
Liu et al., *J. Cell Biol.*, 178:785-798 (2007).
Luke et al., *J. Cell Sci.*, 121 :1887-1898 (2008).
Malhas et al., *J. Cell Biol.*, 176:593-603 (2007).
Mao et al., *Matrix. Biol.*, 24(6):389-399 (2005).
McBeath et al., *Dev. Cell*, 6:483-495 (2004).
McKeown-Longo et al., *J. Cell Biol.*, 100(2):364-74 (1985).
Meaburn et al., *Aging Cell*, 6:139-153 (2007).
Mendjan et al., *Mol. Cell*, 21:811-823 (2006).
Miles et al., *Brit. J. Radiol.*, 71:276-281 (1998).
Mohammed et al., *Mol. Cancer Ther.*, 2(2):183-188 (2003).
Mounkes et al., *Nature*, 423:298-301 (2003).
Munter et al., *BMC Cell Biol.*, 7:23 (2006).
Nelson et al., *Annu. Rev. Cell Dev. Biol.*, 22 :287-309 (2006).
Nelson et al., *Mol. Biol. Cell*, 15 :2943-2953 (2004).
Neri et al., *Nat. Rev. Cancer*, 5(6):436-446 (2005).
Ohtake et al., *J. Cell Sci.*, 119:3822-3832 (2006).
Orr et al., *Dev. Cell.*, 10 :11-20 (2006).
Paszek et al., *Cancer Cell*, 8 :241-254 (2005).
Puckelwartz et al., *Hum. Mol. Genet.*, 18:607-620 (2009).
Raeber et al., *Acta Biomater*, 3:615-629 (2007).
Richert et al., *Biomacromolecules*, 5:1908-1916 (2004).
Roca-Cusachs et al., *Biophys. J.*, 94:4984-4995 (2008).
Salpingidou et al., *J. Cell Biol.*, 178:897-904 (2007).
Sarria et al., *J. Cell Sci.*, 107(6) :1593-1607 (1994).
Saunders et al., *J. Cell Biol.*, 175:179-191 (2006).
Schafer et al., *Nat. Rev. Mol. Cell Bio.*,19 :628-638 (2008).
Sela et al., *Mol. Microbiol*, 10:1049-1055 (1993).
Signäs et al., *PNAS USA*, 86: 699-703 (1989).
Singhvi et al., *Science*, 264: 696-698 (1994).
Shah et al., *Biophys. J.*, 86:2993-3008 (2004).
Shimi et al., *Genes Dev.*, 22:3409-3421 (2008).
Shumaker et al., *Proc. Natl. Acad. Sci. USA*, 103:8703-8708 (2006).
Singhvi et al., *Science*, 264:696-698 (1994).
Somech et al., *J. Cell Sci.*, 118:4017-4025 (2005).
Solon et al., *Biophys. J.*, 93(12):4453-4461 (2007).
Starr, *J. Cell Sci.*, 122, 577-586 (2007).
Stewart-Hutchinson et al., *Exp. Cell Res.*, 314:1892-1905 (2008).
Stewart et al., *Science*, 318:1408-1412 (2007).
Sullivan et al., *J. Cell Biol.*, 147 :913-920 (1999).
Talay et al., *Mol. Microbiol.*, 13:531-539 (1994).
Tan et al., *Proc. Natl. Acad. Sci. USA*, 100:1484-1489 (2003).
Tang et al., *J. Cell Sci.*, 121 :1014-1024 (2008).
Taylor, *Arthritis Res.*, 4(3):S99-S107 (2002).
Taylor et al., *Int. Immun.*, 6:579-591 (1994).
Thundat et al., *Applied Physics Letters*, 64 :2894-2896 (1994).
Tomasini-Johansson et al., *Matrix Biol.*, 25(5):282-293 (2006).
Tomasini-Johansson et al., *J. Biol. Chem.*, 276 :23430-23439 (2001).
Vogel et al., *Nat. Rev. Mol. Cell Biol.*, 7(4):265-275 (2006).
Wang et al., *Nat. Rev. Mol. Cell Biol.*, 10:75-82 (2009).
Wilhelmsen et al., *J. Cell Sci.*, 119:5021-5029. (2006).
Wilhelmsen et al., *J. Cell Biol.*, 171:799-810 (2005).
Wozniak et al., *Nat. Rev. Mol. Cell Biol.*, 10:34-43 (2009).
Wu et al., *Cell*, 83(5):715-724 (1995).
Yamada et al., *Cell*, 130(4):601-610 (2007).
Zajac et al., *Curr. Opin. Cell Biol.*, 20:609-615 (2008).
Zhang et al., *Hum. Mol. Genet.*, 16:2816-2833 (2007).
Zhong et al., *J. Cell Biol.*, 141(2):539-551 (1998).
Zhou et al., *Genes Dev.*, 22 :1231-1243 (2008).
Zhou et al., *Proc. Natl. Acad. Sci. USA*, 97:4052-4057 (2000).
Akerman et al., *Proceedings of the National Academy of Sciences in the United States of America*, 102: 2040-2045 (2005).
Ambesi et al., *Cancer Research*, 65: 148-156 (2005).
Chernousov et al., *Journal of Biological Chemistry*, 266: 10851-10858 (1991).
Eijan et al., *Molecular Biotherapy*, 3: 38-40, (1991).
Kim et al., *The American Journal of Pathology*, 156: 1345-1362 (2000).
Mercurius et al., *Circulation Research*, 82: 548-556 (1998).
Nicosia et al., *Journal of Cellular Physiology*, 154: 654-661 (1993).
Tomasini-Johansson et al., *The Journal of Biological Chemistry*, 276: 23430-23439 (2001).
Yi et al., *Proceedings of the National Academy of Sciences of USA*, 98: 620-624 (2001).
Zhou et al. *Genes & Development*, 22: 1231-1242 (2008).
International Search Report, European Patent Office, International Patent Application No. PCT/US2009/039932, dated Aug. 27, 2009.
Written Opinion of International Searching Authority for PCT/US2009/039932, European Patent Office, dated Aug. 27, 2009.

\* cited by examiner

METHOD OF MODULATING NEOVASCULARIZATION

CROSS REFERENCE TO RELATED APPLICATION

This application claims priority to U.S. Provisional Patent Application No. 61/043,610, filed Apr. 9, 2008.

GRANT FUNDING DISCLOSURE

This invention was made with government support under grant number R01 CA88308, awarded by the National Institutes of Health. The government has certain rights in the invention.

FIELD OF THE INVENTION

The invention relates to materials and methods of modulating neovascularization.

BACKGROUND OF THE INVENTION

Neovascularization, or the formation of new blood vessels, is a highly complex and tightly regulated biological process. Neovascularization begins with the enzymatic breakdown of the basement membrane of a blood vessel. Endothelial cells migrate through the area of degradation, invade the surrounding extracellular matrix, and proliferate to form an elongated column of cells. A lumen forms within the solid cell column upon differentiation of endothelial cells and the basement membrane is subsequently regenerated. Eventually, the newly formed vessel structure connects with existing blood vessels (see, for example, Fotsis et al., 1995. *J. Nutr.*, 125: 790S-797S). The newly formed vessel, as well as existing vessels, can further divide to form branches and capillary networks. The division of existing vessels to form capillary networks is called non-sprouting angiogenesis or intussusception.

Neovascularization is not continuously required on a large scale in adult animals. Indeed, the process for forming blood vessels is often quiescent except in instances of injury and wound repair. Neovascularization is controlled, at least in part, by the body's requirement for a precise combination of signaling molecules, chemical messengers, and mechanical signals to coordinate the biological events necessary for functional blood vessel formation. When vascularization is not stringently controlled, serious pathologies can result. Uncontrolled vascularization is associated with, for instance, tumor growth, edema, diseases of eye (e.g., diabetic retinopathy and the exudative form of age-related macular degeneration), rheumatoid arthritis, psoriasis, and atherosclerosis.

Several strategies for controlling vascularization have been proposed, and many angiogenesis inhibitors have been identified including angiostatin, endostatin, pigment epithelium-derived factor (PEDF), and protamine. However, a major hurdle in treating or preventing angiogenesis is targeting processes uniquely associated with unwanted neovascularization to avoid side effects. For example, U.S. Pat. No. 6,833,373 proposes administering an "integrin antagonist" to, e.g., impair endothelial cell adhesion via integrins, thereby prompting cell death of proliferating endothelial cells. Bouroulous et al. (*J. Cell Biol.*, 143(1): 267-276 (1998)) reported that a 76 amino acid $III_{1-C}$ fibronectin fragment, which forms one of fibronectin's self-assembly sites, causes disassembly of fibronectin matrix and inhibited cell migration and proliferation. However, subsequent studies established that the $III_{1-C}$ fibronectin fragment (also known as "anastellin") did not act by reducing the level of fibronectin present in the extracellular matrix (see, e.g., Ambesi et al. 2005. *Cancer Res.*, 65(1): 148-156). Instead, it has been proposed that anastellin works through a different mechanism, which may include integrin binding (Ambesi, supra). However, integrins are found on many cell types other than endothelial cells, and play a role in other vital physiological processes that would be disrupted by inhibiting integrin function.

Thus, there exists a need for a means of specifically inhibiting vascularization in an animal.

SUMMARY OF THE INVENTION

The invention provides a method of inhibiting neovascularization in a subject. The method comprises administering to the subject an agent that interferes with fibronectin (Fn) matrix assembly in an amount effective to inhibit neovascularization. In some embodiments, the agent does not promote apoptosis and/or does not interfere with binding between integrins and soluble Fn. Examples of suitable agents include, but are not limited to, an antibody or fragment thereof that binds Fn, an Fn fragment, and a functional upstream domain (FUD) of *Streptococcus pyogenes* adhesion F1 protein.

The invention further provides a method of identifying an agent that inhibits neovascularization. The method comprises detecting fibronectin (Fn) matrix assembly by stimulated endothelial cells cultured in three-dimensional culture gel in the presence and absence of an agent. A decrease in Fn matrix assembly in the presence of the agent compared to Fn matrix assembly in the absence of the agent is indicative of an agent that inhibits neovascularization. The invention also provides a method of identifying an agent that inhibits neovascularization, the method comprising detecting changes in nuclear architecture in stimulated endothelial cells cultured in three-dimensional culture gel in the presence and absence of an agent. A reduction in nuclear architecture organization identifies an agent that inhibits neovascularization.

DETAILED DESCRIPTION OF THE INVENTION

The invention provides a method of inhibiting neovascularization in a subject. The method comprises administering to the subject an agent that interferes with fibronectin (Fn) matrix assembly in an amount effective to inhibit neovascularization. The invention is predicated, at least in part, on the surprising discovery that the endothelial cell-dependent unfolding and pericellular polymerization of the soluble glycoprotein, Fn, plays a required—and 3-dimensional (3-D)-specific—role in triggering neovascularization. While not being limited by any particular theory, it is believed that, during neovascularization, endothelial cells embed themselves within a 3-D extracellular matrix (ECM) consisting of crosslinked networks of the clotting protein, fibrin(ogen). Within this extrinsic matrix, endothelial cells are exposed to angiogenic growth factors that initiate neovascularization. Endothelial cells also establish integrin-mediated adhesive interactions with matrix-bound ligands, and undergo shape changes critical to the activation of actomyosin-dependent contractile responses that serve to trigger the motogenic, proliferative, and morphogenic programs underlying neovascularization. In addition, endothelial cell-dependent remodeling of the pericellular ECM controls nuclear compartment organization and architecture, as well as chromatin structure and function, in a 3-D-specific fashion. Growth factor-triggered changes in endothelial cell shape are transmitted to the nuclear envelope via a pathway dependent on F-actin, intermediate filaments, microtubules, actomyosin-generated force and the linker of nucleus and cytoskeleton (LINC) complex embedded within the nuclear membrane. Unexpectedly, the polymerized Fn matrix is necessary for endothelial cells to proliferate, migrate, assemble a functional cytoskeletal-actomyosin complex, and engage the mechanotransduction-sensitive programs that drive 3-D neovessel formation.

Fn matrix assembly involves converting soluble Fn into insoluble fibrillar matrix (Chernousov et al. 1991. *J. Biol. Chem.*, 266(17): 10851-10858). Fn is a ~450 kDa glycoprotein composed of two monomers having three types of "modules" (i.e., type I, II, and III repeats) (Tomasini-Johansson et al. 2006. *Matrix Biol.*, 25(5): 282-293). Soluble Fn binds to the endothelial cell surface by displaying a dominant cell-adhesive domain (module $III_{9-10}$), a carboxy-terminal heparin-binding domain (module $III_{12-14}$), and a 70 kDa amino-terminal domain. The soluble Fn binding sites are recognized by integrins, syndecans, and Fn matrix assembly sites located on the cell surface (Mao and Schwarzbauer. 2005. *Matrix Biol*, 24(6): 389-399; Tomasini-Johansson 2006. supra). Engagement of cell surface adhesion molecules by soluble Fn dimers triggers endothelial cell signaling cascades. The triggered signaling cascades, in turn, initiate globular Fn glycoprotein unfolding, and the consequent exposure of cryptic domains that serve to support Fn polymerization and matrix assembly (Geiger et al. 2001. *Nat Rev Mol Cell Biol*, 2(11): 793-805; Mao and Schwarzbauer, supra; Tomasini-Johansson 2006. supra). Fn molecules multimerize and, over time, organize into fibrils which accumulate in the pericellular space to form an insoluble Fn matrix (Chernousov, supra).

Agents

The inventive method comprises administering an agent that interferes with Fn matrix assembly to a subject. Any agent that inhibits Fn matrix formation is suitable for the invention; the agent is not limited by the particular means by which it impedes Fn polymerization. The agent may interfere with Fn matrix assembly at any point in the polymerization process, such as any fibrillogenesis-related processes described herein. For example, in certain embodiments the agent interrupts unfolding of Fn bound to cell surface molecules. Alternatively or in addition, the agent interferes with polymerization by binding Fn in such a way that blocks association with other Fn molecules. The agent also (or alternatively) hides cryptic binding sites exposed upon Fn unfolding. In this regard, the five N-terminal type I modules of Fn, i.e., the estimated 27 kDa N-terminal fragment or Fn modules $I_{1-5}$ (see, e.g., McKeown-Longo and Mosher. 1985. *J. Cell Bio.*, 100: 364), are required for polymerization, i.e., assembly of Fn to form an insoluble matrix. The agent may bind this region of Fn and block matrix assembly. Alternatively, the agent comprises the 27 kDa N-terminal Fn region and competes with native, soluble Fn to block polymerization. In various embodiments, the agent binds another region of Fn, e.g., type II or type III modules, to sterically block polymerization or hide cryptic binding sites to prevent further association with Fn fibrils. The agent may selectively inhibit Fn matrix formation, i.e., the agent inhibits Fn matrix formation with minimal disruption of other Fn functions. For example, in one aspect, the agent impedes Fn matrix assembly, but does not interfere with binding between integrins and soluble Fn. Alternatively, an agent may be selected which does not promote apoptosis of, e.g., endothelial cells.

Examples of agents for use in the invention include, but are not limited to, chemical moieties (e.g., small molecules), proteins, and nucleic acids. In some embodiments, the agent comprises a protein, such as an intact or full-length protein that interferes with Fn matrix formation. Alternatively, the agent is a protein fragment that inhibits Fn matrix assembly. In certain embodiments, the agent is derived from Fn or procured from another source, e.g., an animal protein, a plant protein, a bacterial protein, a viral protein, or a non-native, genetically-engineered protein or fragment thereof. In one aspect, the agent comprises an Fn fragment that blocks Fn matrix assembly. The nucleic acid sequence of human Fn is publicly available as Entrez Gene ID: 2335 (SEQ ID NO: 1). The fibronectin gene is alternatively spliced, and the amino acid sequences of several splice variants are known: Fn1 isoform 3 preproprotein is designated as Entrez Protein ID: NP_002017.1 (GI: 16933542) (SEQ ID NO: 2), the mature protein spanning residues 32-2355; Fn1 isoform 7 preproprotein is designated as Entrez Protein ID: NP_473375.2 (GI: 47132547) (SEQ ID NO: 3), the mature protein spanning residues 32-657; Fn1 isoform 6 preproprotein is designated as Entrez Protein ID: NP_997639.1 (GI: 47132549) (SEQ ID NO: 4), the mature protein spanning residues 32-2176; Fn1 isoform 2 preproprotein is designated as Entrez Protein ID: NP_997640.1 (GI: 47132551) (SEQ ID NO: 5), the mature protein spanning residues 32-2421; Fn1 isoform 5 preproprotein is designated as Entrez Protein ID: NP_997641.1 (GI: 47132553) (SEQ ID NO: 6), the mature protein spanning residues 32-2296; Fn1 isoform 4 preproprotein is designated as Entrez Protein ID: NP_997643.1 (GI: 47132555) (SEQ ID NO: 7), the mature protein spanning residues 32-2330; and Fn1 isoform 1 preproprotein is designated as Entrez Protein ID: NP_997647.1 (GI: 47132557) (SEQ ID NO: 8), the mature protein spanning residues 32-2477. The amino acid sequence of the precursor of the largest Fn splice variant is designated as Entrez Protein ID: P02751.3 (GI: 2506872) (SEQ ID NO: 9).

In some embodiments, the agent comprises (or consists of) an Fn fragment comprising a portion of the N-terminal region of Fn that interferes with assembly of Fn matrices, such as the Fn 70 kDa catheptic fragment of the mature Fn polypeptide (i.e., the N-terminal fragment produced by catheptic digestion of Fn). The 70 kDa N-terminal fragment comprises the N-terminal type I modules critical for fibrillogenesis. The binding activity of the Fn 70 kDa fragment is localized to the N-terminal 27 kDa region of Fn, and evidence also suggests that the 70 kDa catheptic Fn fragment binds cryptic assembly sites along the Fn molecule (Tomasini-Johansson et al. 2001. *J. Biol. Chem.*, 276(26): 23430-23439). While the 70 kDa fragment binds to cell monolayers, it lacks domain interactions that allow Fn polymerization to proceed and, therefore, is not incorporated into the insoluble Fn matrix (Tomasini-Johansson 2006, supra; Tomasini-Johansson 2001, supra). The invention expressly excludes the 76 amino acid $III_{1-C}$ fibronectin fragment (anastellin) as an agent contemplated. Other Fn-derived fragments that inhibit Fn matrix assembly in vivo by, for example, competing for matrix assembly sites while lacking the capacity to mediate Fn unfolding or matrix formation, also may be used. Methods for identifying Fn fragments that inhibit Fn matrix assembly and neovascularization are described below.

As noted above, the agent need not be derived from Fn; any protein is useful so long as Fn matrix assembly is impeded, resulting in an inhibition of neovascularization. For example, in one aspect, the agent is a bacterial protein that binds Fn and interferes with fibrillogenesis. A number of bacterial proteins bind Fn for adhesion to, and invasion of, host cells. Fn is a ligand for bacterial "microbial surface components recognizing adhesive matrix molecules" (MSCRAMMs) (see, e.g., Jon et al. 1999. *Matrix Biol*, 18: 211-23). The proteins are generally found on the bacterial surface and have a molecular mass of approximately 100 kDa. Typically, the Fn binding region comprises three to five repeated regions of 40-50 residues each, and is located N-terminal of the cell-wall spanning region of the molecule (Jon, supra). Several MSCRAMMs have been identified including, but not limited to, Sfb and protein F of *Streptococcus pyogenes* (Talay et al. 1994. *Mol. Microbiol.*, 13: 531-539; Sela et al. 1993. *Mol. Microbiol.*, 10: 1049-1055); FnbpA and FnbpB of *Staphylococcus aureas* (Signäs et al. 1989. *PNAS USA*, 86: 699-703; Jönsson et al. 1991. *Eur. J. Biochem.*, 2002: 1041-1048); and FnbA and FnbB of *Streptococcus dysgalactiae* (Lindgren et al. 1993. *Eur. J. Biochem.*, 214: 819-827). MSCRAMMs that bind Fn, but which do not inhibit Fn matrix assembly to the desired degree, can be modified to enhance their inhibitory activity. For instance, the Fn binding region of an MSCRAMM is, in one aspect, conjugated, connected, or fused to, e.g., PEG or an Fc region of an antibody to sterically hinder matrix assembly.

In some embodiments, the agent is all or part of a *Streptococcus pyogenes* Fn binding protein, such as an F1 adhesion protein (see, e.g., Tomasini-Johansson 2001, supra). F1 adhesion protein comprises an N-terminal 43-residue upstream non-repetitive domain (UD), followed by five, 37-amino acid tandem repeats (RD5), and a bacterial cell wall attachment region at the C-terminus. In one aspect, the agent comprises the 49-residue functional upstream domain (FUD) of an F1 adhesion protein. FUD comprises the 43-amino acid UD and the first six amino acids of the N-terminal 37-residue repeat. Accordingly, in some embodiments, the FUD comprises the amino acid sequence KDQSPLAGESGETEYITEVYGN-QQNPVDIDKKLPNETGFSGNMVETEDT (SEQ ID NO: 10). FUD recognizes Fn's N-terminal ~27 kDa fragment and adjacent gelatin binding domain (Tomasini-Johansson 2001, supra). Upon binding, FUD interferes with assembly of insoluble Fn matrix and inhibits neovascularization in a subject.

Other bacterial proteins also are suitable for the invention. The functional repeat domain (FRD) of *S. pyogenes* binds the most N-terminal ~27 kDa fragment of Fn. FRD is a 44-residue fragment encompassing the C-terminus of one RD5 repeat through the N -terminus of the next RD5 repeat, flanked at both ends by the sequence MGGQSES (SEQ ID NO: 11) present in each RD repeat. For example, the FRD protein comprises the amino acid sequence MGGQSES-VEFTKDTQTGMSGQTTPQIETEDT-KEPGVLMGGQSES (SEQ ID NO: 12). Although the FRD peptide inhibits fibrillogenesis to a lesser degree than FUD, the FRD peptide may have properties particularly suitable for some embodiments. *S. pyogenes* F1 adhesion protein and fragments thereof are further described in Tomasini-Johansson 2001, supra.

In other embodiments, the agent is an antibody or fragment thereof that binds Fn. Any type of antibody is suitable in the context of the invention, including polyclonal, monoclonal, chimeric, humanized, or human versions having full length heavy and/or light chains. Antibodies according to the invention are obtained by immunization and cell fusion procedures as described herein and known in the art. Monoclonal antibodies of the invention are generated using a variety of known techniques (see, for example, Coligan et al. (eds.), *Current Protocols in Immunology,* 1:2.5.12.6.7 (John Wiley & Sons 1991); *Monoclonal Antibodies, Hybridomas: A New Dimension in Biological Analyses*, Plenum Press, Kennett, McKeam, and Bechtol (eds.) (1980); and *Antibodies: A Laboratory Manual*, Harlow and Lane (eds.), Cold Spring Harbor Laboratory Press (1988); and Picksley et al., "Production of monoclonal antibodies against proteins expressed in *E. coli*," in *DNA Cloning* 2: *Expression Systems, 2nd Edition*, Glover et al. (eds.), page 93 (Oxford University Press 1995)).

Likewise, human antibodies are generated by any of a number of techniques including, but not limited to, Epstein Barr Virus (EBV) transformation of human peripheral blood cells (e.g., containing B lymphocytes), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein. Methods for obtaining human antibodies from transgenic animals are further described, for example, in Green et al. 1994. *Nature Genet.* 7: 13-21; Lonberg et al. 1994. *Nature,* 368: 856-859; Taylor et al. 1994. *Int. Immun.* 6: 579-591; U.S. Pat. No. 5,877,397; Bruggemann et al., 1997. *Curr. Opin. Biotechnol.* 8: 455-58; and Jakobovits et al. 1995. *Ann. N. Y. Acad. Sci.,* 764: 525-35.

Antibody fragments include antigen-binding regions and/or effector regions of the antibody, e.g., $F(ab')_2$, Fab, Fab', Fv (fragments consisting of the variable regions of the heavy and light chains), Fc, and Fd fragments. Antibody fragments are, in various aspects, incorporated into single domain antibodies, single-chain antibodies (immunological molecules wherein light and heavy variable regions are connected by a peptide linker), maxibodies, minibodies, intrabodies, diabodies, triabodies, tetrabodies, variable domains of new antigen receptors (v-NAR), and bis-single chain Fv regions (see, e.g., Hollinger and Hudson. 2005. *Nature Biotechnology,* 23(9): 1126-1136) to inhibit Fn matrix formation.

An antibody or antibody fragment is isolated from nature, synthetic, or genetically-engineered. Antibody fragments derived from an antibody are obtained, e.g., by proteolytic hydrolysis of the antibody. For example, papain or pepsin digestion of whole antibodies yields a 5S fragment termed $F(ab')_2$ or two monovalent Fab fragments and an Fc fragment, respectively. $F(ab')_2$ can be further cleaved using a thiol reducing agent to produce 3.5S Fab monovalent fragments. Methods of generating antibody fragments are further described in, for example, U.S. Pat. No. 4,331,647; Nisonoff et al. 1960. *Arch. Biochem. Biophys.,* 89: 230-244; Porter. 1959. *Biochem. J.,* 73: 119-127; Edelman et al., in *Methods in Enzymology,* 1: 422 Academic Press (1967); and by Andrews, S. M. and Titus, J. A. in *Current Protocols in Immunology* (Coligan et al., eds), John Wiley & Sons, New York (2003), pages 2.8.1-2.8.10 and 2.10A.1-2.10A.5.

An antibody or fragment thereof also can be genetically engineered such that the antibody or fragment thereof comprises, e.g., a variable region domain generated by recombinant DNA engineering techniques. For example, in one aspect, a specific antibody variable region is modified by insertions, deletions, or changes in or to the amino acid sequences of the antibody to produce an antibody of interest. In this regard, polynucleotides encoding complementarity determining regions (CDRs) of interest are prepared, for example, by using polymerase chain reaction to synthesize variable regions using mRNA of antibody-producing cells as a template (see, for example, Larrick et al. 1991. *Methods: A Companion to Methods in Enzymology,* 2: 106-110; Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)). Current antibody manipulation techniques allow construction of engineered variable region domains containing at least one CDR and, optionally, one or more framework amino acids from a first antibody and the remainder of the variable region domain from a second antibody.

The antibody or fragment thereof binds any region of Fn so long as matrix assembly, and neovascularization, is inhibited. In some embodiments, the method comprises administering Ab 9D2 or Ab L8 (Chernousov et al. 1987. *FEBS Lett.*, 217(1): 124-8; Chernousov et al. 1991. *J. Bio. Chem.*, 266 (17): 10851-10858), or antigen-binding fragments thereof, to inhibit neovascularization. Antibody 9D2 binding activity is localized to the first type III module of Fn (Chernousov, supra). The epitope for antibody L8 is found in a region spanning the type $I_9$ module and type $III_1$ module, at or near residues 526-675 (Chernousov, supra). Other antibodies which bind Fn and inhibit neovascularization also are suitable in the context of the invention. For example, in various embodiments, the method comprises administering an antibody or fragment thereof that (i) competes for binding with Ab 9D2 or Ab L8, (ii) binds the region of Fn recognized by Ab 9D2 or L8 (i.e., a region spanning the type $I_9$ module and type $III_1$ module, or a region comprising the first type III module of Fn), or (iii) binds at or near Fn type $I_9$ module and type $II_{1,2}$ modules, while inhibiting neovascularization. If desired, the agent comprises an Fn-binding peptide comprising all or part of the antigen-binding elements of an antibody, such as Ab L8 or Ab 9D2, but lacking all or part of the framework regions of an antibody. In this regard, the agent comprises an Fn -binding peptide comprising one, two, three, four, five, or six complementary determining regions (CDRs) of an Fn-binding antibody that inhibits neovascularization, e.g., Ab L8 or Ab 9D2. Methods of identifying complementary determining regions and specificity determining regions are known in the art and further described in, for example, Tamura et al. 2000. *J. Immunol.*, 164: 1432-1441.

The antibody or fragment thereof preferably specifically binds to Fn, meaning that the antibody or fragment thereof binds Fn with greater affinity than it binds to an unrelated control protein. In other words, the antibody or fragment thereof recognizes and bind Fn preferentially and substantially exclusively (i.e., is able to distinguish Fn from other known polypeptides by virtue of measurable differences in binding affinity) in various aspects of the invention. Depending on the embodiment, the antibody or fragment thereof binds to Fn with an affinity that is at least 50, 100, 250, 500, 1000, or 10,000 times greater than the affinity for an unrelated control protein. Screening assays to determine binding specificity/affinity of an antibody, as well as identify antibodies that compete for binding sites, are well known and routinely practiced in the art. For a comprehensive discussion of such assays, see Harlow et al. (Eds), *Antibodies A Laboratory Manual; Cold Spring Harbor Laboratory*; Cold Spring Harbor, N.Y. (1988), Chapter 6. For example, affinity may be determined using a variety of techniques, such as affinity ELISA assay, BIAcore assay, equilibrium/solution assay, and the like. In one aspect, an antibody or fragment thereof has a binding affinity for Fn of less than or equal to $1 \times 10^7$ M, less than or equal to $1 \times 10^8$ M, less than or equal to $1 \times 10^9$ M, less than or equal to $1 \times 10^{10}$ M, less than or equal to $1 \times 10^{11}$ M, or less than or equal to $1 \times 10^{12}$ M.

The agent alternatively comprises a variant or derivative of any of the exemplary agents described herein. By "variant" is meant a peptide or polypeptide wherein one or more amino acid residues are inserted into, deleted from, and/or substituted into the naturally occurring (or at least known) amino acid sequence for the agent. In this regard, the agent is a variant of any of the above-described inhibitors of Fn matrix assembly having, e.g., 65%, 70%, 75%, 80%, 85%, 90%, 91%, 92%, 93%, 94%, 95%, 96%, 97%, 98%, or 99% identity to the the inhibitor. The variant also must retain the ability to interfere with Fn matrix assembly and inhibit neovascularization. For example, in one aspect, the agent is a variant of Fn or a fragment thereof, such as a variant of Fn's 70 kDa catheptic fragment, having 65%, 70%, 75%, 80%, 85%, 90%, 91%, 92%, 93%, 94%, 95%, 96%, 97%, 98%, or 99% identity to the 70 kDa catheptic fragment, while retaining inhibitory activity. The terms "identical" or percent "identity," in the context of two or more polynucleotide or polypeptide sequences, refer to two or more sequences or subsequences that are the same or have a specified percentage of nucleotides or amino acid residues that are the same, when compared and aligned for maximum correspondence including necessary gaps, as measured using one of the following sequence comparison algorithms or by visual inspection.

Identity can exist over a region that is at least about 20 residues in length, such as over a region of at least about 50-100 residues or over at least about 150 residues. Regions of identity can span the active domain of the peptide. The active domains and target binding regions of many agents are known in the art and/or provided herein; a practitioner can modify an agent of interest to create a functional variant falling within the scope of the invention. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman. 1981. *Adv. Appl. Math.*, 2: 482; by the homology alignment algorithm of Needleman & Wunsch. 1970. *J. Mol. Biol.*, 48: 443; by the search for similarity method of Pearson & Lipman. 1988. *Proc. Natl. Acad. Sci. USA*, 85: 2444; by computerized implementations of these algorithms (GAP, BESTFIT, FASTA, and TFASTA in the Wisconsin Genetics Software Package, Genetics Computer Group, 575 Science Dr., Madison, Wis.), or by visual inspection. One example of a useful algorithm is PILEUP, which uses a simplification of the progressive alignment method of Feng & Doolittle. 1987. *J. Mol. Evol.*, 35: 351-360, and is similar to the method described by Higgins & Sharp. 1989. *CABIOS*, 5: 151-153. Another algorithm useful for generating multiple alignments of sequences is Clustal W (Thompson et al. 1994. *Nucleic Acids Research*, 22: 4673-4680). An example of algorithm that is suitable for determining percent sequence identity and sequence similarity is the BLAST algorithm (Altschul et al. 1990. *J. Mol. Biol.*, 215: 403-410; Henikoff & Henikoff. 1989. *Proc. Natl. Acad. Sci. USA*, 89: 10915; Karlin & Altschul. 1993. *Proc. Natl. Acad. Sci. USA*, 90: 5873-5787). Software for performing BLAST analyses is publicly available through the National Center for Biotechnology Information.

To generate functional variants, one skilled in the art can review structure-function studies identifying residues in similar peptides that are important for activity or structure. In view of such a comparison, one can predict the importance of amino acid residues in a peptide that correspond to amino acid residues that are important for activity or structure in similar peptides. One skilled in the art also can analyze three-dimensional structure and amino acid sequence in relation to that structure in similar polypeptides. A number of scientific publications have been devoted to the prediction of secondary structure (Moult. 1996. *Curr. Op. in Biotech.,* 7(4): 422-427; Chou et al. 1974. *Biochemistry,* 13(2): 222-245; Chou et al. 1974. *Biochemistry,* 113(2): 211-222; Chou et al. 1978. *Adv. Enzymol. Relat. Areas Mol. Biol.,* 47: 45-148; Chou et al. 1979. *Ann. Rev. Biochem.,* 47: 251-276; Chou et al. 1979. *Biophys. J.,* 26: 367-384; and Holm et al. 1999. *Nucl. Acid. Res.,* 27(1): 244-247). In view of structure information, one skilled in the art predicts the alignment of amino acid residues of a peptide with respect to its three-dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays, such as those known in the art and/or described herein. Such data could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

Variants also include fusion proteins wherein a portion of one peptide is fused to another polypeptide, a polypeptide fragment, or amino acids not generally recognized to be part of a protein sequence. In various aspects, a fusion or chimeric peptide comprises the entire amino acid sequences of two or more peptides or, alternatively, can be constructed to comprise portions (fragments) of two or more peptides (e.g., 10, 20, 50, 75, 100, 400, 500, or more amino acid residues). In some instances, it may be desirable to fuse the active domains of two or more factors to generate a fusion peptide having a desired biological activity. In addition to all or part of the Fn matrix inhibitors described herein, a fusion protein, in one aspect, includes all or part of any suitable peptide comprising a desired biological activity/function, such as a therapeutic peptide. Indeed, in some aspects, the fusion protein comprises, for instance, one or more of the following: an immunogenic peptide; a peptide with long circulating half life, such as an immunoglobulin constant region; a marker protein; a peptide that facilitates purification of the agent; a peptide sequence that promotes formation of multimeric proteins (such as leucine zipper motifs that are useful in dimer formation/stability); and fragments of any of the foregoing.

"Derivatives" include agents that have been chemically modified in some manner distinct from insertion, deletion, or substitution variants. In this regard, the agent is chemically bonded with polymers, lipids, other organic moieties, and/or inorganic moieties. Derivatives are prepared in some embodiments to increase solubility, absorption, circulating half-life, or targeting to particular cells, tissues, or organs. Chemical modification also may eliminate or attenuate any undesirable side effect of the agent, such as immunogenicity. In this regard, agents covalently modified to include one or more water soluble polymer attachments, such as polyethylene glycol, polyoxyethylene glycol, or polypropylene glycol are contemplated herein (U.S. Pat. Nos. 4,640,835; 4,496,689; 4,301,144; 4,670,417; 4,791,192; and 4,179,337). Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of any of the foregoing.

In addition, in one aspect, the agent competes with, or cross-blocks, one of the exemplary agents described herein to impede Fn matrix assembly. "Cross-block" is meant to refer to the ability of an agent to interfere with the binding of other fibrillogenesis inhibitors, such as those described herein, to Fn and impede (i.e., reduce or prevent) Fn matrix assembly, thereby inhibiting neovascularization. Agents that compete with or cross-block Fn matrix inhibitors and inhibit neovascularization can be determined using any suitable method, such as the binding assays, Fn matrix assembly models, and angiogenesis models described herein.

In some embodiments, a nucleic acid comprising a coding sequence for an agent of the method is administered. For example, in one aspect, a nucleic acid encoding FUD is incorporated into an expression vector and administered to a subject to inhibit neovascularization. One of ordinary skill in the art will appreciate that any of a number of expression vectors known in the art are suitable for use in the present method, such as, but not limited to, plasmids, plasmid-liposome complexes, and viral vectors. Any of these expression vectors can be prepared using standard recombinant DNA techniques described in, e.g., Sambrook et al., Molecular Cloning, a Laboratory Manual, 2d edition, Cold Spring Harbor Press, Cold Spring Harbor, N.Y. (1989), and Ausubel et al., Current Protocols in Molecular Biology, Greene Publishing Associates and John Wiley & Sons, New York, N.Y. (1994). Expression vectors, nucleic acid regulatory sequences, and administration methods, are further discussed in U.S. Patent Publication No. 20030045498.

Methods of Identifying/Characterizing an Agent

The efficacy of the agent to inhibit neovascularization is determined using any of a number of methods, such as those methods known in the art. Screening assays to determine binding specificity/affinity of an agent are well known and routinely practiced in the art. For a comprehensive discussion of such assays, see Harlow et al. (Eds), *Antibodies A Laboratory Manual; Cold Spring Harbor Laboratory*; Cold Spring Harbor, N.Y. (1988), Chapter 6. Binding affinity may be determined using a variety of techniques, such as, but not limited to, affinity ELISA assay, surface plasmon resonance (BIAcore™) assay, equilibrium/solution assay, and the like. In addition, several methods of identifying agents that interfere with Fn polymerization are described in the Examples provided herein. In this regard, the invention also provides a method for identifying an agent that interferes with Fn matrix assembly and inhibits neovascularization in vivo. The method comprises detecting fibronectin (Fn) matrix assembly by stimulated endothelial cells cultured in three-dimensional culture gel in the presence and absence of an agent. A decrease in Fn matrix assembly in the presence of the agent compared to Fn matrix assembly in the absence of the agent is indicative of an agent that inhibits neovascularization.

In one aspect, exposure of an endothelial cell to the agent inhibits changes in the nuclear architecture organization required to support angiogenesis. Accordingly, the invention provides a method for identifying an agent that inhibits neovascularization. The method comprises detecting changes in nuclear architecture in stimulated endothelial cells cultured in three-dimensional culture gel in the presence and absence of an agent, wherein a reduction in nuclear architecture reorganization identifies an agent that inhibits neovascularization. Nuclear envelope morphology is examined in several ways using any of a number of imaging techniques, such as electron microscopy. For example, in one aspect, the nuclear envelope is viewed to detect infoldings and surface irregularities (i.e., exposure to the agent impedes nuclear restructuring that generates a uniform laminar structure in stimulated cells). Alternatively or in addition, the organization of nuclear pore distribution is examined (i.e., exposure to the agent reduces the redistribution of nuclear pores observed in stimulated endothelial cells in 3-D culture). Exemplary imaging techniques are described in, for example, Aebi et al. 1986. *Nature*, 323:560-564; Gerace et al. 1984. *J. Cell Sci. Suppl.*, 1:137-60, and the Examples.

Additionally, the ability of an agent to inhibit neovascularization in vivo is determined using any suitable animal angiogenesis model, such as a mouse or rabbit ear model of neovascularization (Frank et al. 1994. *Microsurgery*, 15(6): 399-404), an animal model of rheumatoid arthritis (Haas et al. 2007. *Arthritis Rheum.*, 56(8): 2535-48), or an in vivo cancer model, such as a mouse melanoma metastasis model (Lee et al. 2006. *Cancer Chemother. Pharmacol.*, 57(6): 761-71) or a canine model of human invasive urinary bladder cancer (Mohammed et al. 2003. *Mol. Cancer Ther.*, 2(2): 183-188). Methods of monitoring neovascularization in a human patient are well known. Doppler imaging and magnetic resonance imaging detect blood flow or vascularization changes in tissue (see, e.g., Taylor. 2002. *Arthritis Res.*, 4(suppl. 3): S99-S107), and microscopic examination of tissue biopsies detects changes in vessel number or quality. Perfusion computed tomography ("perfusion CT") (Miles et al. 1998. *Brit. J. Radiol.*, 71: 276-281) and dynamic contrast enhanced magnetic resonance imaging (MRI) (Hathout et al. 2007. *Transpl. Int.*, 20(12): 1059-1065) also are effective in evaluating neovascularization. Ocular neovascularization can be detected using fluorecein angiography, color Doppler imaging, and by clinical examination.

"Inhibiting" neovascularization does not require a 100% abolition of blood vessel formation. Any decrease in unwanted neovascularization constitutes a beneficial biological effect in a subject. In this regard, the invention reduces neovascularization by, e.g., at least about 5%, at least about 10% or at least about 20% compared to levels of neovascularization observed in the absence of the inventive method (e.g., in a biologically-matched control subject or specimen that is not exposed to the agent of the inventive method). In some embodiments, neovascularization is reduced by at least about 30%, at least about 40%, at least about 50%, or at least about 60%. In some embodiments, the inventive method inhibits neovascularization by at least about 70%, at least about 80%, at least about 90%, or more (about 100%) compared new blood vessel formation in the absence of the agent of the inventive method.

Administration Considerations

The inventive method is, in one aspect, performed after it has been determined that a subject is at risk for unwanted neovascularization (e.g., cancer markers are detected) or after neovascularization is detected (e.g., following tumor resection). To this end, the agent is administered before vessel formation is detected to protect, in whole or in part, against unwanted neovascularization. In other aspects, the agent is administered after angiogenesis has begun to prevent, in whole or in part, further unwanted blood vessel formation.

A particular administration regimen for a particular subject will depend, in part, upon the agent used, the amount of agent administered, the route of administration, and the cause and extent of any side effects. The amount of agent administered to a subject (e.g., a mammal, such as a human) in accordance with the invention should be sufficient to effect the desired response over a reasonable time frame. Dosage typically depends upon a variety of factors, including the particular agent employed, the age and body weight of the subject, as well as the existence or extent of any disease or disorder in the subject. The size of the dose also will be determined by the route, timing, and frequency of administration. Accordingly, the clinician titers the dosage and modifies the route of administration to obtain the optimal therapeutic effect, and conventional range-finding techniques are known to those of ordinary skill in the art. Purely by way of illustration, the inventive method comprises administering, e.g., from about 0.1 µg/kg to up to about 100 mg/kg or more, depending on the factors mentioned above. In other embodiments, the dosage ranges from 1 µg/kg up to about 100 mg/kg; or 5 µg/kg up to about 100 mg/kg; or 10 µg/kg up to about 100 mg/kg. Some conditions or disease states require prolonged treatment, which may or may not entail administering lower doses of agent over multiple administrations.

Suitable methods of administering a physiologically-acceptable composition, such as a pharmaceutical composition comprising the agent of the invention, are well known in the art. Although more than one route can be used to administer an agent, a particular route can provide a more immediate and more effective reaction than another route. Depending on the circumstances, a pharmaceutical composition comprising the agent is applied or instilled into body cavities, absorbed through the skin or mucous membranes, ingested, inhaled, and/or introduced into circulation. For example, in certain circumstances, it will be desirable to deliver a pharmaceutical composition comprising the agent orally, through injection by intravenous, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal means, by sustained release systems, or by implantation devices. If desired, the agent is administered regionally via intraarterial or intravenous administration feeding the region of interest, e.g., via the hepatic artery for delivery to the liver. Alternatively, the composition is administered locally via implantation of a membrane, sponge, or another appropriate material on to which the desired molecule has been absorbed or encapsulated. Where an implantation device is used, the device is, one aspect, implanted into any suitable tissue or organ, and delivery of the desired molecule is, for example, via diffusion, timed-release bolus, or continuous administration. In other aspects, the agent is administered directly to exposed tissue during tumor resection or other surgical procedures. Therapeutic delivery approaches are well known to the skilled artisan, some of which are further described, for example, in U.S. Pat. No. 5,399,363.

To facilitate administration, the agent is, in various aspects, formulated into a physiologically-acceptable composition comprising a carrier (i.e., vehicle, adjuvant, or diluent). The particular carrier employed is limited only by chemico-physical considerations, such as solubility and lack of reactivity with the compound, and by the route of administration. Physiologically-acceptable carriers are well known in the art. Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). Injectable formulations are further described in, e.g., Pharmaceutics and Pharmacy Practice, J. B. Lippincott Co., Philadelphia. Pa., Banker and Chalmers. eds., pages 238-250 (1982), and ASHP Handbook on Injectable Drugs, Toissel, 4th ed., pages 622-630 (1986)). A pharmaceutical composition comprising an agent of the invention is, in one aspect, placed within containers, along with packaging material that provides instructions regarding the use of such pharmaceutical compositions. Generally, such instructions include a tangible expression describing the reagent concentration, as well as, in certain embodiments, relative amounts of excipient ingredients or diluents (e.g., water, saline or PBS) that may be necessary to reconstitute the pharmaceutical composition.

Combination Therapy

When appropriate, the agent is administered in combination with other substances (e.g., therapeutics) and/or other therapeutic modalities to achieve an additional (or augmented) biological effect. These other therapeutics/co-treatments include, for example, radiation treatment, hyperthermia, surgical resection, chemotherapy, additional agents that inhibit fibrillogenesis, other anti-angiogenic factors (for instance, soluble growth factor receptors (e.g., sflt), growth factor antagonists (e.g., angiotensin), etc.), antibiotics, hormone therapy, anti-inflammatory agents (e.g., Non-Steroidal Anti-Inflammatory Drugs (NSAIDs) or steroidal anti-inflammatory substances), pain relievers, and the like.

The invention thus includes administering to a subject an agent (or multiple agents) that interferes with Fn matrix assembly, in combination with one or more additionally suitable substances(s), each being administered according to a regimen suitable for that medicament. This aspect includes concurrent administration (i.e., substantially simultaneous administration) and non-concurrent administration (i.e., administration at different times, in any order, whether overlapping or not) of the agent and one or more additionally suitable agents(s). It will be appreciated that different components are, in certain aspects, administered in the same or in separate compositions, and by the same or different routes of administration.

Chemotherapy treatment for use in conjunction with the invention employ anti-neoplastic agents including, but not limited to, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), and hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; pipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Exemplary cytokines or hematopoietic factors for use in conjunction with the invention include, but are not limited to, Interleukin (IL)-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IFN-omega, IL-7, IL-8, IL-9, IL-10, IL-12, IL -13, IL-14, IL-15, IL-16, IL-17, IL-18, IL-19, IL-20, IL-21, IL-22, IL-23, IL-24, IL-31, IL-32 alpha, IL-33, thrombopoietin (TPO), angiopoietins, for example Ang-1, Ang-2, Ang-4, Ang-Y, the human angiopoietin-like polypeptides ANGPTL1 through 7, vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor $2\alpha$, cytokine-induced neutrophil chemotactic factor $2\beta$, $\beta$ endothelial cell growth factor, endothelin 1, epidermal growth factor, epigen, epiregulin, epithelial-derived neutrophil attractant, fibroblast growth factor (FGF) 4, FGF 5, FGF 6, FGF 7, FGF 8, FGF 8b, FGF 8c, FGF 9, FGF 10, FGF 11, FGF 12, FGF 13, FGF 16, FGF 17, FGF 19, FGF 20, FGF 21, FGF acidic, FGF basic, glial cell line -derived neutrophic factor receptor $\alpha$1, glial cell line-derived neutrophic factor receptor $\alpha$2, growth related protein, growth related protein $\alpha$, growth related protein $\beta$, growth related protein $\gamma$, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, leukemia inhibitory factor receptor $\alpha$, nerve growth factor, nerve growth factor receptor, neuropoietin, neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor $\alpha$, platelet derived growth factor receptor $\beta$, pre-B cell growth stimulating factor, stem cell factor (SCF), stem cell factor receptor, tumor necrosis factor (TNF), including TNF0, TNF1, TNF2, transforming growth factor (TGF) $\alpha$, TGF $\beta$, TGF $\beta$1, TGF $\beta$1.2, TGF $\beta$2, TGF $\beta$3, TGF $\beta$5, latent transforming growth factor $\beta$1, TGF $\beta$ binding protein I, TGF $\beta$ binding protein II, TGF $\beta$ binding protein III, thymic stromal lymphopoietin (TSLP), TNF receptor type I, TNF type II, urokinase-type plasminogen activator receptor, vascular endothelial growth factor, and chimeric proteins and biologically or immunologically active fragments thereof.

Additional combination therapies not specifically listed herein are also within the scope of the present invention.

Other Considerations

It will be appreciated that the materials and methods of the invention are used to treat a number of diseases associated with deregulated or undesired angiogenesis. Such diseases include, but are not limited to, ocular neovascularization, such as retinopathies (e.g., diabetic retinopathy, age-related macular degeneration, choroidal neovascularization, and the like); psoriasis; hemangioblastoma; hemangioma; arteriosclerosis; inflammatory disease, such as a rheumatoid or rheumatic inflammatory disease, e.g., arthritis (including rheumatoid arthritis); arterial or post-transplantational atherosclerosis; endometriosis; and neoplastic diseases, e.g., solid tumors and liquid tumors (such as leukemias).

Many neovascularization-related disease states are monitored using the methods described herein to determine the degree of neovascularization in a subject. When the invention is used to inhibit neovascularization associated with tumor growth, several additional parameters are measured to determine the efficacy of the method to, e.g., alleviate tumor progression in a subject. The proper combination of parameters for a particular situation is established by the clinician. Tumor size is figured, for instance, by measuring tumor dimensions or estimating tumor volume using available computer software, such as FreeFlight software developed at Wake Forest University that enables accurate estimation of tumor volume. Tumor size also can be determined by tumor visualization using, for example, CT, ultrasound, SPECT, spiral CT, MRI, photographs, and the like. Measurement of tumor size, detection of new tumors, tumor antigens, or markers (e.g., CEA, PSA, or CA-125), biopsy, surgical downstaging, PET scans, and the like, can point to the overall progression (or regression) of cancer in a human. Biopsy is particularly useful in detecting a reduction of neovascularization within a tissue.

EXAMPLES

The invention, thus generally described, will be understood more readily by reference to the following examples, which are provided by way of illustration and are not intended to limit the invention.

Example 1

This Example illustrates the ability of Fn polymerization inhibitors to interfere with Fn matrix formation, cell proliferation, cell migration, and tubulogenesis in three-dimensional cell culture, which simulates in vivo conditions of neovascularization.

Endothelial cells were isolated from human umbilical cord veins by collagenase digestion and cultured in Medium 199 (Gibco) containing 20% human serum, 50 µg/ml endothelial cell growth supplement (BD Biosciences), 100 U/ml penicillin, and 100 µg/ml streptomycin (Hiraoka et al. 1998. *Cell*, 95(3): 365-377). For 2-D/3-D culture, endothelial cell monolayers (no later than third passage) were suspended by mild trypsinization and dispersed within or plated atop fibrin (3 mg/ml) or collagen (2.2 mg/ml) gels (prepared as described in Hiraoka, supra, and Hotary et al. 2003. *Cell*, 114(1): 33-45) and stimulated with a cocktail of growth factors including 100 ng/ml human vascular endothelial growth factor (Genentech), 50 ng/ml human hepatocyte growth factor (Genentech), 10 ng/ml human TGFα (Biosource), 0.5 ng/ml TGFβ1 (R and D Systems), and 100 µg/ml heparin (Sigma). In selected experiments, endothelial cell spheroids were prepared and suspended in 3-D fibrin gels.

When embedded in a 3-D gel of cross-linked fibrin and stimulated with a cocktail of pro-angiogenic factors in serum-containing media, human endothelial cells assumed a spherical configuration during the first 8-12 hours of culture. No increase in cell number was detected until after 48 hours in culture, whereafter the embedded cells displayed a stretched phenotype. Endothelial cell number subsequently increased after the 2 day lag period, and a tubulogenic program was engaged which led to the formation of an anastomosing network of patent neovessels by day 6. As observed in vivo (Clark et al. 1982. *J. Exp. Med.*, 156(2): 646-651; Risau and Lemmon. 1988. *Dev. Biol.*, 125(2): 441-450; and Neri and Bicknell. 2005. *Nat. Rev. Cancer*, 5(6): 436-446), endothelial cell morphogenesis occurred in tandem with the assembly of a network of Fn fibrils that not only enmesh the stretched endothelial cells observed at 48 hours, but also ensheath the tubules formed at the end of the 6 day culture period. Thus, three-dimensional cell culture simulates in vivo conditions that allow new blood vessel formation.

The effect of Fn matrix assembly, or lack thereof, on endothelial cell function during neovascularization was assessed. Human serum was depleted of Fn by gelatin-sepharose affinity chromatography (Amersham) and supplemented with either 20 µg/ml of human plasma Fn (Sigma) or FITC-labeled Fn. Endothelial cells were incubated in 3-D cell culture with:

i) monoclonal antibodies L8 or 9D2 that are directed against Fn domains embedded within, or near, the Fn III$_{1,2}$ modules that are critical for regulating Fn-Fn interactions (final concentration of 100 µg/ml);

ii) a 70 kDa amino-terminal Fn fragment that interferes with the polymerization of intact Fn dimers by competing for matrix assembly sites on the endothelial cell surface (Sigma; 75 µg/ml);

iii) FUD, which binds directly to the N-terminal matrix assembly domain of Fn, or Del29, wherein FUD residue 29 is deleted to abrogate Fn binding (250 nM);

iv) mouse IgG (control; Pierce); Blebbistatin (Calbiochem; 50 µM); or cytochalasin D (Sigma; 10 µM)

(Chernousov et al. 1991. *J. Biol. Chem.*, 266(17): 10851-10858; Tomasini-Johansson et al. 2001. *J. Biol. Chem.*, 276 (26): 23430-23439; Mao and Schwarzbauer. 2005. *Matrix Biol.*, 24(6): 389-399; and Tomasini-Johansson et al. 2006. *Matrix Biol.*, 25(5): 282-293). The inhibitors block Fn matrix assembly without affecting the initial binding of soluble Fn binding to α5β1. Cell number in 3-D cultures was determined by hemacytometry after dissolving gels with 2 mg/ml bacterial collagenase (Worthington) while the number of patent tubules was determined in randomly selected cross-sections. Fn matrix assembly and cell morphology were monitored by confocal laser microscopy. To examine cell migration, endothelial cells were embedded in a 100 µl fibrin gel for 2 hours, then placed within a 500 µl gel for 8 days in the presence of Del29, FUD, control IgG, or L8, after which migration from the inner gel was assessed.

Fn fibrillogenesis inhibitors completely blocked the ability of fibrin-embedded endothelial cells to assemble a Fn matrix. For example, addition of FUD to incubating cells attenuated Fn polymerization, while incubation with Del29 did not negatively impact Fn matrix formation. In the absence of Fn fibrillogenesis—and despite the presence of a surrounding 3-D fibronectin matrix, serum, and exogenously provided pro-angiogenic growth factors—the endothelial cells were unable to undergo the expected shape change and retain a spherical morphology. Coincident with the block in Fn matrix deposition, the 3-D migratory and proliferative responses of embedded endothelial cells were blunted significantly, and tubulogenesis was effectively terminated. Because Fn/α5β1 interactions were left intact, no increase in apoptosis (as assessed by TUNEL staining) was detected in the absence of Fn fibrillogenesis.

The ability of Fn matrix inhibitors to block neovessel formation is not restricted to the specific use of fibrin gel suspension system. Endothelial cells spheroids were embedded in gels of 3-D fibrin or type I collagen matrix and cultured for 6 days in the absence or presence of mAb L8 (100 µg/ul). Tubulogenesis was assessed by phase contrast microscopy, and the assembly of a FITC-labeled Fn matrix was monitored by confocal laser microscopy. Similar, if not identical, results were obtained when neovessel formation was initiated with spheroids of endothelial cells embedded in 3-D fibrin gels (Korff and Augustin. 1998. *J. Cell Biol.*, 143(5): 1341-1352) or alternatively, when type I collagen was used as the supporting matrix.

This example demonstrates methods to inhibit neovascularization. Endothelial cell responses required for neovascularization were blunted, if not completely prevented, by inhibition of Fn matrix formation.

Example 2

This Example further demonstrates the effect of inhibiting Fn polymerization on cellular processes associated with angiogenesis.
Blocking Fn Polymerization Interrupts Endothelial Cell Cytoskeletal Organization Changes in cell geometry impact the signaling cascades that control cell migration, proliferation, and morphogenesis (Chen et al. 1997. *Science*, 276(5317): 1425-1428; Tan et al. 2003. *Proc. Natl. Acad. Sci. USA*, 100(4): 1484-1489; McBeath et al. 2004. *Dev. Cell*, 6(4): 483-495; and Ingber. 2006. *FASEB J.*, 20(7): 811-827). In vivo, integrins and growth factors collaborate in the activation of MAPK pathways which regulate the angiogenic response (Eliceiri et al. 1998. *J. Cell Biol.*, 140(5): 1255-1263; Geiger et al. 2001. *Nat. Rev. Mol. Cell Biol.*, 2(11): 793-805; Huang et al. 2004. *Proc. Natl. Acad. Sci. USA*, 101(7): 1874-1879; and Ingber, supra). To determine the degree to which endothelial cell responses to growth factor and integrin-ligand signals are linked to Fn matrix assembly, the phosphorylation of the MAP kinases, ERK1 and 2, JNK, and p38 were monitored in the absence or presence of fibrillogenesis inhibitors during the 48 hour period that precedes proliferative responses.

Levels of phosphorylated ERK1/2, JNK, and p38 were determined by immunoblot analysis in lysates of endothelial cells cultured in fibrin gels in the presence of either control IgG or mAb L8 for 0 hours, 2 hours, 1 day, or 2 days. Total ERK1/2 served as the loading control. In control cultures, sustained MAP kinase activation is maintained throughout the 48 hours incubation period in a fashion that recapitulates the in vivo setting (Eliceiri, supra; and Corson et al. 2003. *Development*, 130(19): 4527-4527). However, independent of the marked changes in endothelial cell morphology and cytoskeletal organization associated with the inhibition of Fn fibrillogenesis, phosphorylation patterns of ERK1/2, JNK, and p38 were largely unaffected.

Despite the comparable initiation of signal transduction cascades in endothelial cells competent or incompetent for Fn matrix assembly, cell responses to integrin and growth factor-mediated signals also are dictated by the organization of actin cytoskeletal architecture (Chen, supra; Huang, supra; Ingber, supra; and Bershadsky et al. 2006. *Curr. Opin. Cell Biol.*, 18(5): 472-481). To further study the effects of Fn matrix inhibition, additional cytological processes associated with angiogenesis were examined. Endothelial cells were cultured within 3-D or 2-D fibrin gels in the presence of the FUD or Del 29 peptides for 2 days. F-actin cytoskeletal organization was monitored following staining with Alexa 488-conjugated phalloidin. Cells also were stained with an antibody against activated β1 integrin or transfected with a GFP-tagged vinculin expression vector (pRK-vinculin-EGFP) to study distribution. Following counterstaining with Alexa 594-labeled phalloidin, fluorescence was monitored by confocal laser microscopy.

In tandem with the ability of growth factor-stimulated endothelial cells to adopt an elongated phenotype in 3-D culture, a reticulated pattern of well-organized stress fibers was resolved by F-actin phalloidin staining when cells were cultured in the presence of the Del29 control peptide. In 3-D culture, stress fibers terminate at specialized β1 integrin- and vinculin-rich sites of cell-matrix interactions termed 3-D adhesions (Geiger, supra; Larsen et al. 2006. *Curr. Opin. Cell Biol.*, 18(5): 463-471). As such, endothelial cells transduced with a GFP-tagged vinculin expression vector or alternatively immunostained with an activated β1 integrin-specific monoclonal antibody, established both vinculin and activated β1 integrins into stitch-like structures at the endothelial cell periphery. In the absence of Fn fibrillogenesis, however, stress fiber formation was suppressed completely, and actin staining was confined to the cortical envelope in a punctate network. Further, specific interactions between either activated β1 integrins or vinculin and F-actin networks could no longer be discerned. Endothelial cells alternatively cultured atop fibrin matrices in a 2-D configuration assembled a well-organized stress fiber-focal adhesion network whose organization was unaffected by inhibitors of Fn fibrillogenesis.
Matrix Inhibition Reduces Cellular Tractional Forces and Gene Expression Dependent Thereon Adhesive interactions between cells and their surrounding matrix allow for the generation of tractional forces that regulate cell fate and function (McBeath, supra; Discher et al. 2005. *Science*, 310(5751): 1139-1143; Engler et al. 2006. *Cell*, 126(4): 677-689; Larsen, supra; Vogel and Sheetz. 2006. *Nat. Rev. Mol. Cell Biol.*, 7(4): 265-275; and Yamada and Cukierman. 2007. *Cell*, 130(4): 601-610). The ability of embedded endothelial cells to generate tractional forces on the fibrin matrix was determined in the presence or absence of Fn fibrillogenesis inhibitors. In stressed ECM gels wherein cells are permitted to exert isometric tension, the degree of force exerted by cells on the surrounding fibrillar network can be assessed by monitoring gel contraction after the matrix is released from the surrounding culture dish (Corbett and Schwarzbauer. 1999. *J. Biol. Chem.*, 274 (30): 20943-20948; Even-Ram et al. 2007. *Nat. Cell Bio.*, 9 (3): 299-309). As such, 3-D fibrin gels were cast in individual wells of 24-well plates and cultured alone or in the presence of embedded endothelial cells for 2 days in the presence of control IgG, mAb L8, mAb 9D2, the 70 kDa Fn fragment, or the FUD peptide. Gels were detached from the edges of the culture wells and contraction was monitored after an additional incubation period of 10 hours at 37° C.

Growth factor-stimulated endothelial cells cultured in control gels for 48 hours were able to actively contract the released fibrin gel. By contrast, each of the Fn fibrillogenesis inhibitors markedly attenuated the ability of the embedded endothelial cells to generate tractional forces under 3-D, but not 2-D, culture conditions.

Tractional forces exerted at cell-matrix adhesion sites require the activation of an actinomyosin motor complex whose assembly is tightly linked to actin cytoskeleton organization, non-muscle myosin II isoform expression, and the rigidity of the surrounding substratum (Meshel et al. 2005. *Nat. Cell Biol.,* 7(2): 157-164; Engler, supra; and Even-Ram, supra; Yoneda et al. 2007. *Mol. Cell. Biol.,* 19(1): 66-75). β-actin, α-actinin, myosin light chain-2 (MLC2), and non-muscle myosin IIA and IIB isoform (NMMIIA and NMMIIB, respectively) protein levels were monitored in 3-D embedded endothelial cells to determine the effect of Fn matrix inhibition on the expression of gene products critical to the generation of tractional forces. Endothelial cells were cultured in 3-D fibrin gels for 2 days with either the FUD peptide or the control Del29 peptide. Levels of β-actin, α-actinin, NMMIIA, NMMIIB, and MLC2 were measured by Western blot, with ERK1/2 serving as the loading control. As assessed by semi-quantitative densitometry, the levels of β-actin, actinin and MLC2 were 58±7% (n=5; mean±1 SD), 62% (n=2), and 60±12% (n=3; mean±1 SD) of control, respectively. Significantly, whereas each cytoskeletal component is expressed in growth factor-stimulated endothelial cells actively assembling a Fn matrix, endothelial cells cultured in the presence of FUD or Ab L8 express markedly reduced levels of β-actin, α-actinin, and MLC2.

Intracellular Stiffness Decreases Upon Inhibition of Fn Fibrillogenesis

Endothelial cells cultured atop highly malleable surfaces retain a spherical configuration, fail to organize stress fibers, and are unable to exert tractional forces—a phenotype identical to that observed in 3-D-embedded, Fn matrix assembly-incompetent endothelial cells. A cell's internal stiffness is a viscoelastic property governed by cytoskeletal assembly, actin crosslinking, and the production of actomyosin-dependent stress. Internal stiffness changes as a function of the perceived stiffness of the surrounding substratum (Solon et al. 2007. *Biophys. J.,* 93(12): 4453-4461). Therefore, the micromechanical properties of 3-D-embedded endothelial cells were monitored via intracellular nanorheology.

Prior to embedding in the 3-D fibrin matrix, endothelial cells were ballistically microinjected with 100 nm polystyrene beads to circumvent the endocytic pathway and subsequent directed motion of the beads. After 3 days of incubation, the beads dispersed in the cytoplasm and their centroids were tracked with high spatial and temporal resolution using fluorescence microscopy. Relative to control endothelial cells, the mean square displacement (MSD) of the beads was significantly increased in cells treated with the FUD peptide, indicating a significant relative cytoplasmic softening compared to that of cells where Fn matrix assembly is intact. Elastic moduli, which quantify the local resistance of the cytoplasm against small random forces acting on the surface of the beads, were derived from MSD curves to quantify cellular mechanical properties. The elastic modulus of the cytoplasm of FUD-treated cells is significantly lower than that of control cells (P<0.001), indicating a pronounced defect in internal stiffness and the cell's ability to sense a sufficiently rigid substratum.

In the absence of Fn fibrillogenesis, an impaired ability of embedded endothelial cells to generate myosin-dependent forces and increase cytoplasmic stiffness was predicted to affect both Fn unfolding, as well as the ability of the cells to properly register the mechanical properties of the surrounding substratum (Wu et al. 1995. *Cell,* 83(5): 715-724; Zhong et al. 1998. *J. Cell Biol.,* 141(2): 539-551; Baneyx et al. 2002. *Proc. Natl. Acad. Sci. USA,* 99(8): 5139-5143; Discher et al. 2005. *Science,* 310(5751): 1139-1143; Engler, supra; and Yoneda, supra). As such, the rheologic and functional characteristics of endothelial cells were assessed in the presence of the specific myosin ATPase inhibitor, blebbistatin. Endothelial cells were cultured in 3-D fibrin gels for 2 days in the presence or absence of 50 μM±blebbistatin. F-actin organization and Fn matrix assembly was monitored by confocal laser microscopy and staining with Alexa 488-conjugated phalloidin.

Blebbistatin-treated endothelial cells phenocopied Fn matrix assembly-incompetent cells. In particular, endothelial cells treated with blebbistatin failed to increase cytoplasmic stiffness, failed to undergo cell shape change, failed to assemble a pericellular Fn matrix, and did not reorganize cytoskeletal architecture. Endothelial cell tubulogenesis was blocked completely. Hence, myosin ATPase activity and Fn matrix assembly each play required roles in regulating the endothelial cell's ability to match internal stiffness with that of the surrounding substratum so as to propagate the mechanotransduction-initiated signals critical to neovessel formation.

This Example illustrates the ability of agents of the inventive method to inhibit cell functions required for neovascularization.

Example 3

This Example illustrates the ability of the inventive method to inhibit neovascularization in vivo.

Inhibition of Fn matrix formation is a targeted approach to inhibiting unwanted neovascularization as Fn polymerization is relatively unique to neovessel formation. In this regard, Fn matrix assembly in the context of human tumor angiogenesis was assessed. Renal cell carcinoma (stages GI-III), breast carcinoma, and normal kidney cells were stained for UEA-1 or with mAb L8, which only recognizes unfolded Fn epitopes that are exposed during Fn fibrillogenesis (Chernousov et al. 1991. *J. Biol. Chem.,* 266(17): 10851-10858; Zhong et al. 1998. *J. Cell. Biol.,* 141(2): 539-551). Normal breast cells were stained for FVIIIRAg or with mAb L8. Immunostaining of a series of renal cell carcinomas and invasive ductal breast carcinomas demonstrated that vascular wall L8 immunoreactivity is dramatically increased in tissues undergoing active vascularization/angiogenesis. In both renal cell carcinoma and invasive ductal breast carcinoma specimens, all blood vessels and vascular channels were strongly L8-reactive with additional stromal staining seen in some cases of breast cancer. In normal tissues, immunoreactivity for the L8 Fn epitope was observed infrequently as small streaks in fewer than 10% of the vessels.

The functional role for fibrillogenesis in tissue sites undergoing active angiogenesis in vivo was assessed. To this end, 3-D composite gels of fibrin and type I collagen were placed atop the chorioallantoic membrane (CAM) of live chicks, and angiogenesis was initiated in the presence of FUD or the Del29 peptide control. In particular, 3-D matrices of type I collagen or a type I collagen/fibrin composite matrix were cast in transwell tissue culture inserts (24 well size) perforated with a 25 gauge needle. A 30 μl Matrigel (BD Biosciences) reservoir was placed atop the matrix containing 200 ng VEGF, 100 ng HGF, and either Del29 or FUD. The entire apparatus was placed atop the dropped CAM of 10-11 day old fertile chicken eggs. Following incubation in a humidified incubator at 37° for 3 days, the matrices were harvested. Vascular ingrowth was monitored by light microscopy following H&E staining. In some experiments, FITC-Fn (McKeown-Longo and Mosher. 1985. *J. Cell. Biol.,* 100(2):

364-74) was supplemented in the matrices during the culture period, and Fn fibrillogenesis within the gels was monitored by confocal laser microscopy.

Under control conditions, angiogenic vessels infiltrated the extracellular matrix (ECM) construct in tandem with the deposition of a dense network of Fn fibrils. In the presence of FUD, however, Fn matrix assembly was almost completely inhibited and neovessel formation was ablated.

This Example, as well as the preceding and foregoing Examples, demonstrates that agents that impede Fn matrix formation inhibit neovascularization.

Example 4

This Example demonstrates that modulating cell shape by, e.g., inhibiting Fn polymerization, also modulates nuclear architecture and function.
Regulation of Nuclear Morphology by 3-D Extracellular Matrix (ECM) Remodeling At sites of tissue damage, inflammation or neoplasia, fibrinogen is converted into a 3-D meshwork of fibrin fibrils that serve as a structural support for endothelial cells undergoing neovascularization (Chun et al. 2006. *Cell*, 125: 577-591; Hiraoka et al. 1998. *Cell*, 95: 365-377; Schafer and Werner. 2008. *Nat. Rev. Mol. Cell Biol.*, 9: 628-638; Zhou et al. 2008. *Genes Dev.*, 22: 1231-1243). This process can be recapitulated in vitro by embedding serum-supplemented human endothelial cells within a 3-D fibrin gel in the presence of the pro-angiogenic factors, VEGF and HGF. Human umbilical vein endothelial cells were isolated from umbilical cords by perfusion of the umbilical vein with type 3 collagenase (Worthington, Lakewood, N.J.) and cultured in Medium-199 (Invitrogen, Carlsbad, Calif.) with 20% human serum and 50 µg/ml endothelial cell growth supplement (ECGS; BD Biosciences, Franklin Lakes, N.J.). For 3-D culture, endothelial cells were suspended in a solution of thrombin and aprotinin (Sigma, St. Louis, Mo.) and mixed 1:1 with a solution of 6 mg/ml fibrinogen (Calbiochem, Gibbstown, N.J.). Vasculogenesis was triggered by treatment with 100 ng/ml VEGF, 50 ng/ml HGF (Genentech, San Francisco, Calif.). Fibronectin fibrillogenesis was tracked in 3-D by co-culture with human fibronectin (Sigma) labeled with Alexa-594 (Invitrogen).

In the presence of VEGF and HGF, endothelial cells i) underwent marked changes in cell morphology from spherical to elongated, ii) mobilized proteinases which degrade the surrounding fibrin, iii) assembled a pericellular meshwork of fibronectin fibrils, and iv) initiated proliferative and tubulogenic responses that result in the formation of an anastomosing network of neovessels over a 6 day culture period (Hiraoka, supra; Saunders et al., 2006. *J Cell Biol*. 175: 179-191; Zhou et al., 2008. *Proc. Natl. Acad. Sci. USA*, 97: 4052-4057). Growth factors, fibrinolytic membrane-type matrix metalloproteinases (MT-MMPs), and fibronectin fibril assembly are each required for the tubulogenic program; endothelial cells suspended in 3-D fibrin gels with serum-supplemented media failed to elongate, proliferate or form neovessels when i) the VEGF/HGF cocktail was omitted (hereafter termed as the baseline or unstimulated condition) or ii) VEGF/HGF-stimulated cells were cultured in the presence of GM6001 (Calbiochem), a synthetic MMP inhibitor, or FUD (Zhou, et al. supra), a fibronectin fibril assembly inhibitor (Chun et al., 2004. *Cell*, 125: 757-767; Saunders et al., supra; Tomasini-Johansson et al., 2001. *J. Biol. Chem.*, 276: 23430-23439; Zhou et al, supra). Endothelial cells cultured atop—rather than embedded within—fibrin gels (herein referred to as 2-D culture) display distinct growth requirements from those observed in 3-D culture. In 2-D culture, neither GM6001 nor FUD affect the growth of VEGF/HGF-stimulated endothelial cells.

As the 3-D-specific requirements for MT-MMPs and fibronectin matrix assembly correlate with changes in endothelial cell morphology, efforts were initiated to identify mechanistic routes whereby cell shape changes impact cell function. In particular, the impact of ECM remodeling on nuclear architecture was investigated. Nuclear architecture was tracked by either transfecting cells with a GFP-tagged form of the nuclear matrix filament, lamin A, or by immunostaining for the integral nuclear membrane protein, emerin (Dahl et al., 2008. *Circ. Res.*, 102: 1307-1318; Glynn and Glover, 2005. *Hum. Mol. Genet.*, 14: 2959-2969; Starr, 2009. *J. Cell Sci.*, 122: 577-586; Stewart et al., 2007. *Science*, 318: 1408-1412). Under 2-D conditions, endothelial cell nuclei assumed an ellipsoid shape when cultured atop fibrin gels in the absence or presence of VEGF/HGF. In marked contrast, under 3-D conditions, endothelial cells cultured within fibrin gels in the absence of VEGF/HGF unexpectedly display a distorted morphology with multiple lamin A matrix and emerin infoldings and surface irregularities. Upon addition of VEGF/HGF, however, the nuclei of fibrin-embedded endothelial cells undergo a dramatic, and 3-D-specific, remodeling to assume a more classic, ovoid morphology. Three-dimensional reconstructions of DAPI-stained nuclei confirm that nuclear architecture transitions between multi-lobed and smooth elliptical shapes in the absence or presence, respectively, of VEGF/HGF.

Nuclear matrix architecture controls the distribution of the nuclear pore complexes that regulate the trafficking of protein and RNA across the nuclear envelope (Goldman et al., 2004. *Proc. Natl. Acad. Sci. USA*, 101: 8963-8968; Hawryluk-Gara et al., 2005. *Mol. Biol. Cell*, 16: 2382-2394; Liu et al., 2007. *J. Cell. Biol.*, 178: 785-798). As such, the localization of nuclear pores was assessed in intact cells by monitoring the localization of the component protein, NUP153. In 3-D culture, unstimulated endothelial cells accumulate NUP153-containing pore complexes at nuclear membrane invaginations. In contrast, the nuclei of VEGF/HGF-stimulated endothelial cells display a uniform distribution of pore complexes in nuclear membranes. Hence, nuclear shape and nuclear pore complex distribution are regulated in tandem by VEGF/HGF signaling in 3-D culture.

To determine the roles of MMP-dependent proteolysis and fibronectin matrix assembly in mediating nuclear shape and nuclear pore complex changes, fibrin-embedded endothelial cells were stimulated with VEGF/HGF in the presence of FUD or GM6001. Blocking fibronectin fibrillogenesis or MMP activity locked endothelial cell nuclei into the multilobular conformation characteristic of unstimulated 3-D-embedded endothelial cells. Further, fibrin-embedded endothelial cells stimulated with VEGF/HGF and treated with either GM6001 or FUD completely failed to redistribute nuclear pore complexes. These findings are not confined to fibrin matrices; similar results are obtained when endothelial cells are embedded within a 3-D ECM comprised of type I collagen fibrils, the major component of interstitial tissues. While abnormalities in nuclear envelope architecture can occur in cells undergoing apoptosis, the formation of multi-lobed nuclei does not correlate with increased TUNEL staining. The observed changes in nuclear shape occur only under 3-D culture conditions; the nuclear architecture of endothelial cells cultured under 2-D conditions is unaffected by inhibiting either MMP activity or fibronectin fibrillogenesis.

3-D ECM Remodeling Regulates Chromatin Structure

Perturbations in nuclear shape and nuclear pore complexes have not previously been demonstrated in endothelial cells or any other normal cell population. Yet, multi-lobed nuclei and anomalous nuclear pore complex distributions can be observed in laminopathies, a pleiotropic series of genetic disorders wherein mutations in lamin or emerin impact chromatin organization, histone modifications, and transcriptional activity (Csoka et al., 2004. *Aging Cell,* 3: 235-243; Dechat et al., 2008. *Genes Dev,* 22: 832-853; Dillon, 2008. *Dev Cell,* 15: 182-186; Malhas et al., 2007. *J. Cell Biol.,* 176: 593-603; Mendjan et al., 2006. *Mol. Cell,* 21: 811-823; Shumaker et al., 2006. *Proc. Natl. Acad. Sci. USA,* 103: 8703-8708; Tang et al., 2008. *J. Cell Sci.,* 121: 1014-1024). To determine whether VEGF/HGF-dependent changes in nuclear shape similarly affect chromatin structure/function, chromatin packaging was tracked at the single-endothelial cell level by monitoring GFP-tagged histone H2B or pericentromeric constitutive heterochromatin localization. H2B and heterochromatin localization was visualized by immunostaining for trimethylated lysine 9 of histone H3 (H3K9me3) (Shumaker, supra; Tang, supra).

In unstimulated endothelial cells embedded within 3-D fibrin gels, GFP-H2B and H3K9me3 localization revealed chromatin condensation at discrete peripheral locations in the nucleus. By contrast, following exposure to VEGF/HGF for 48 hours, chromatin was dramatically reorganized in elongated endothelial cells, assuming a diffuse distribution with a relative collapse of the interchromatin space. VEGF/HGF-stimulated global chromatin redistribution was completely inhibited by blocking MMP activity or pericellular fibronectin matrix assembly.

Histone acetylation can be regulated by chromatin positioning within the nucleus (Finlan et al., 2008. *PLoS Genet,* 4: e1000039; Somech et al., 2005. *J. Cell Sci.,* 118: 4017-4025). Thus, the acetylation status of histones H3 and H4 was assessed as functional markers of changes in chromatin organization. Stimulation of endothelial cells in 3-D with VEGF/HGF triggered a significant increase in acetylated histone H3 and H4, changes which are attenuated significantly by blocking MMP activity or fibronectin fibrillogenesis. Under 2-D culture conditions, however, ECM remodeling played no significant role in regulating endothelial cell chromatin organization. Taken together, these data support a model wherein ECM remodeling regulates chromatin organization and structure in a 3-D-specific manner.

The morphology of nucleoli and nuclear speckles—which serve, respectively, as ribosomal RNA and pre-mRNA processing sites—was assessed by immunostaining for fibrillarin (a pre-rRNA processing protein) or SC-35 (a pre-mRNA splicing protein) (Tang et al., supra). Activating endothelial cells with VEGF/HGF in 3-D resulted in the reorganization of fibrillarin from a single, centrally-located cluster of nucleoli within the interchromatin space, to multiple foci dispersed throughout the nucleus. Likewise, nuclear speckle morphology changed from a small number of large foci to more numerous, smaller foci. In both cases, the patterns of fibrillarin and SC-35 staining observed in VEGF/HGF -stimulated endothelial cells in 3-D culture could be reversed to that resembling unstimulated endothelial cells by blocking MMP activity or fibronectin matrix assembly. By contrast, VEGF/HGF, FUD, and GM6001 did not affect fibrillarin or SC-35 distribution under 2-D culture conditions.

VEGF/HGF-induced chromatin dispersion, histone acetylation, and nuclear speckle decompaction observed in 3-D culture are consistent with global activation of transcription (Lamond and Spector, 2003. *Nat. Rev. Mil. Cell Biol.,* 4: 605-612; Tang et al., supra). As such, RNA synthesis was quantified in cultured endothelial cells. VEGF/HGF treatment resulted in a marked induction of transcriptional activity, a process attenuated significantly when ECM remodeling events are blocked by either FUD or GM6001. Using low dose actinomysin D to inhibit selectively rRNA synthesis (Ben-Ze'ev et al., 1980. *Cell,* 21: 365-372), mRNA and rRNA synthesis were observed to be inhibited by ~50% (data not shown). Under 2-D culture conditions, transcriptional activity proceeded independently of pericellular ECM remodeling and was unaffected by FUD or GM6001. Hence, 3-D ECM remodeling is a regulator of nuclear organization as well as chromatin structure and function.

This Example demonstrates that ECM-regulated cell shape changes control neovessel morphogenesis by directly impacting nuclear architecture and function. The results show that 3-D-embedded, unstimulated endothelial cells display convoluted nuclei with multiple lobulations and surface invaginations containing nuclear pore complex aggregates. It does not appear that these unusual shapes have previously been described in any normal cell population. Nevertheless, following stimulation with VEGF/HGF, MMP-dependent proteolysis and fibronectin fibrillogenesis allowed endothelial cells to re-sculpt nuclear architecture to generate elliptical nuclei marked by a uniformly distributed array of nuclear pore complexes. By contrast, under standard, 2-D culture conditions atop mechanically rigid, adhesive substrata, cell shape changes—and consequent nuclear shape changes—are not constrained by an encasing 3-D ECM.

In addition, the observed multi-lobed nuclei and distorted nuclear pore distribution bore striking resemblance to the nuclear shapes observed in cells recovered from human patients bearing mutations in the lamin A/C, emerin or nesprin genes; a family of degenerative diseases termed the laminopathies (Crisp and Burke. 2008. *FEBS Lett.,* 582: 2023-2032; Dechat et al. 2008. *Genes Dev.,* 22: 832-853; Goldman et al. 2004. *Proc. Natl. Acad. Sci. USA,* 101: 8963-8968; Holaska. 2008. *Circ. Res.,* 103: 16-23). Studies of cells isolated from laminopathy patients or mouse models of human laminopathies, as well as cells engineered to silence lamin expression have demonstrated that disrupted nuclear matrix architecture induces spatial and functional reorganization of the genome, resulting in global alterations in transcription and consequent effects on cell function (Columbaro et al. 2005. *Cell Mol. Life Sci.,* 62: 2669-2678; Csoka et al. 2004. *Aging Cell,* 3: 235-243; Dechat, supra; Malhas et al. 2007. *J. Cell Biol.,* 176: 593-603; Meaburn et al. 2007. *Aging Cell,* 6: 139-153; Shimi et al. 2008. *Genes Dev.,* 22: 3409-3421; Shumaker et al. 2006. *Proc. Natl. Acad. Sci. USA,* 103: 8703-8708; Tang et al. 2008. *J. Cell Sci.,* 121: 1014-1024). While the specific functional impact of mutations in nuclear envelope proteins on cell function have not been considered to be of necessary relevance to normal cell behavior, the structural changes we observed in endothelial cell nuclei in 3-D culture led us to hypothesize that chromatin re-organization might purposefully accompany the nuclear envelope restructuring that occurs during capillary morphogenesis. Consistent with the propsition that chromatin organization is a critical regulator of endothelial cell function (Haberland et al. 2009. *Nat. Rev. Genet.,* 10: 32-42), VEGF/HGF stimulation induces the translocation of endothelial cell chromatin from a condensed peripheral location to a dispersed, uniform distribution with coincident induction of histone acetylation. Remarkably, these changes in chromatin organization were inhibited almost completely by blocking fibronectin matrix—or MMP—dependent cell shape changes. The observed correlation of reduced histone acetylation with peripheral chromatin distributions is in accord with the observation that peripheral locations in the nuclear envelope contain histone deacetylase activity. Furthermore, changes in nuclear architecture couple with morphological alterations in nucleoli and nuclear speckles were indicative of significant reductions in ribosomal RNA synthesis and pre-mRNA metabolism, thus connecting ECM-regulated changes in nuclear structure to genome function.

Example 5

This Example demonstrates that signals generated by cell shape changes mediated by ECM remodeling are transduced to the nucleus via intracellular filaments that tether the cell-ECM interface and nuclear interior.

Cytoskeleton as a Transducer of ECM Structural Dynamics to the Nuclear Envelope

Cytoskeletal architecture and tension are closely coupled to cell geometry (Huang et al., 1998. *Mol. Biol. Cell*, 9: 3179-3193; Nelson et al., 2004. *Mol. Biol. Cell*, 15: 2943-2953; Tan et al., 2003. *Proc. Natl. Acad. Sci. USA*, 100: 1484-1489; Wozniak and Chen, 2009. *Nat. Rev. Mol. Cell Biol.*, 10: 34-43), and can influence nuclear envelope shape (Munter et al., 2006. *BMC Cell. Biol.*, 7: 23; Roca-Cusachs et al., 2008. *Biophys. J.*, 94: 4984-4995; Sarria et al., 1994. *J. Cell Sci.*, 107 (Pt 6): 1593-1607). Hence, cytoskeletal organization in 3-D culture was assessed by examining F-actin, β-tubulin, and vimentin distribution. Treatment of 3-D-embedded endothelial cells with VEGF/HGF induced marked cytoskeletal reorganization, with F-actin, β-tubulin and vimentin redistributing from a diffuse, cortical pattern to a longitudinal fibrous network in tandem with an increase in isometric tension. In contrast, VEGF/HGF-triggered cytoskeletal remodeling and force induction in 3-D culture are inhibited completely by abrogating MMP activity or fibronectin fibrillogenesis, effects that were not observed under 2-D culture conditions.

Since ECM rigidity regulates cytoskeletal remodeling and force generation, and consequently cell function (Engler et al., 2006. *Cell*, 126: 677-689; Wozniak and Chen, supra; Zajac and Discher, 2008. *Curr. Opin. Cell Biol.*, 20: 609-615), atomic force microscopy micro-indentation (AFM) was employed to quantify endothelial cell-dependent changes in ECM remodeling. AFM was performed by first washing fibrin gels with phosphate buffered saline (PBS) after removing culture medium. Samples were mechanically characterized using an Asylum MFP-3D atomic force microscope (Asylum Research, Santa Barbara, Calif.). Micro-indentation was performed using a sphere-tipped probe (Novascan, Ames, Iowa) with a sphere diameter of 5 μm and a nominal spring constant of ~60 pN/nm. The cantilever spring constant was confirmed by thermal fluctuation method (Thundat et al., 1994. *Applied Physics Letters*, 64: 2894-2896). The AFM system was calibrated by following the manufacturer's recommended procedure before each indentation measurement. AFM micro-indentation was performed in PBS solution at room temperature. Individual force-indentation profile was acquired at an indentation rate of 2 μm/s using deflection trigger mode with a trigger value of 200 nm. The AFM tip was positioned either adjacent to or away from a cell. Shear modulus at each position was calculated from fitting force-indentation data using a Hertz sphere model (Richert et al., 2004, *Biomacromolecules*, 5: 1908-1916). In the presence of FUD or GM6001, VEGF/HGF-stimulated endothelial cells exhibit significantly lower 3-D pericellular rigidity, consistent with a required role for ECM remodeling events in the regulation of intracellular tension.

Taken together, cytoskeletal reorganization and contractile tension may serve as the biomechanical effectors that transmit structural and mechanical cues from the pericellular ECM to the nuclear envelope. VEGF/HGF-stimulated endothelial cells were treated with either (a) blebbistatin to inhibit myosin ATPase function, or (b) nocodazole to prevent microtubule assembly under 3-D culture conditions (Salpingidou et al., 2007. *J. Cell Biol.*, 178: 897-904; Zhou et al., supra). Both agents completely inhibit endothelial cell 3-D tubulogenesis while impairing the contractile force exerted on the 3-D ECM. The data indicate that endothelial cell force generation is inhibited to a degree similar to that observed with GM6001 or FUD treatment. Further, compared with the ellipsoid nuclear shapes observed in VEGF/HGF-stimulated endothelial cells in 3-D culture, endothelial cells cultured in the presence of blebbistatin or nocodazole displayed i) multi-lobed nuclei with perturbations in nuclear pore distribution, ii) chromatin condensations at the nuclear periphery with increased interchromatin space and iii) decreased levels of acetylated histones H3 and H4. In toto, these results demonstrate that the ECM-dependent regulation of cytoskeletal organization is a critical determinant of nuclear as well as chromatin architecture.

Nesprins Regulate 3-D Organization of the Nuclear Compartment

Physical interactions between cytoskeletal networks and the nucleus are mediated by a family of Klarsicht, ANC-1, Syne homology (KASH) domain-containing proteins. The C-terminal domains of the proteins are embedded within the outer nuclear membrane, where they interact with the inner nuclear membrane via members of the SUN protein family (Crisp et al., 2006. *J. Cell Biol.*, 172: 41-53; Dechat et al., supra; Starr, supra; Stewart et al., supra; Wilhelmsen et al., 2006. *J. Cell Biol.*, 171: 799-810). In turn, SUN proteins span the inner nuclear membrane to establish binding interactions with a scaffold of lamin family members and nuclear pore complexes (Dechat et al., supra; Starr, supra; Stewart et al., supra). To determine whether this interaction plays a role in the nuclear morphology regulation by ECM remodeling, expression of nesprins-1 and 2 (also termed Syne-1 and 2) nesprin-3 was examined in 3-D-embedded endothelial cells. Nesprins-1 and 2 bind F-actin, while nesprin-3 indirectly interacts with intermediate filaments via binding of plectin (Crisp and Burke, 2008. *FEBS Lett.*, 582: 2023-2032; Starr, supra; Stewart et al., supra).

Endothelial cells were observed to express nesprins 1-3 at both the mRNA and protein levels. The nuclear envelope of VEGF/HGF-treated endothelial cells embedded in 3-D fibrin gels displayed uniform nesprin distribution. In contrast, unstimulated endothelial cells, as well as VEGF/HGF-stimulated endothelial cells treated with GM6001 or FUD, displayed irregular nesprin distributions, with nesprin aggregates accumulating at nuclear membrane invaginations.

Physical interactions between the cytoskeleton, nesprins, SUN proteins and lamins likely dictate nuclear structure because endothelial cells remodel their surrounding ECM as a means to organize cytoskeletal structure (Zhou et al., supra). Hence, the cytoskeleton/nesprin continuum was perturbed by expressing the dominant negative GFP-KASH. GFP-KASH acts as a truncated nesprin protein that binds to SUN proteins without interacting directly with cytoskeletal elements (Crisp and Burke, supra; Crisp et al., supra; Stewart-Hutchinson et al., 2008. *Exp. Cell Res.*, 314: 1892-1905). Endothelial cells were transduced with amphotropic retroviruses encoding GFP-KASH (provided by B. Burke, University of Florida) in the presence of 50 ng/ml VEGF and 6 μg/ml polybrene (Sigma, St. Louis, Mo.). Compared to VEGF/HGF-stimulated endothelial cells cultured in 3-D, endothelial cells expressing GFP-KASH failed to trigger nuclear remodeling and adopt the multi-lobed nuclear shape characteristic of unstimulated endothelial cells. Further, GFP-KASH expression induced peripheral chromatin condensation and perturbed the distribution of nucleoli and nuclear speckles, while inducing marked reductions in acetylated histone H3 or H4 levels. Consistent with nuclear organization regulating endothelial cell function, KASH -expressing cells were unable to participate in a normal tubulogenic response.

Coupling of Cell Geometry with Nuclear Structure/Function

If ECM-dependent changes in 3-D cell geometry regulate nuclear architecture, then direct modulation of endothelial cell shape would be predicted to impact nuclear organization and chromatin structure. To test this hypothesis, endothelial cells were cultured within 3-D, biomimetic poly(ethylene glycol) (PEG) hydrogels containing RGD peptides incorporated pendantly within a transglutaminase-crosslinked structure engineered to be either susceptible, or resistant, to MMP-mediated degradation (Ehrbar et al., 2007. *Biomacromolecules*, 8: 3000-3007; Raeber et al., 2007. *Acta Biomater.*, 3: 615-629). In this manner, endothelial cell spreading is controlled as a function of the susceptibility of the 3-D hydrogel to proteolytic remodeling.

MMP-resistant or MMP-degradable PEG hydrogels were formed by FXIIIa catalyzed reaction as described in Ehrbar et al., supra. Briefly, 8-arm PEG-Gln and PEG-Lys were blended to generate stoichiometrically balanced ([Gln]/[Lys]) PEG precursor solutions. The PEG-Lys component was either chosen to contain a linker peptide that is susceptible (GPQG/IWGQ, with/indicating the cleavage site (SEQ ID NO: 13)) or resistant (GDQGIAGF (SEQ ID NO: 14)) to MMP-mediated degradation. The PEG precursor solutions (1.5, 2.0 and 2% w/v) were cross-linked upon addition of 10 U/mL FXIIIa in presence of 50 mM TrisHCl, pH 7.6, 50 mM $CaCl_2$, 50 µM Lys-RGD (Ac -FKGGRGDSPG-NH2 (SEQ ID NO: 15), NeoMPS Strasbourg, France) and cells suspended in medium 12% (v/v) of the total volume. To form hydrogel discs, 20 µL drops of the still liquid reaction mixture were sandwiched between sterile, hydrophobic glass microscopy slides that were separated by 1 mm spacers and clamped with binder clips. Polymerization was then allowed to take place for 30 minutes at 37° C. in a humidified incubator. To visualize the matrix, 25 µM Lys-FITC (Ac-FKGGGK-FITC-NH2 (SEQ ID NO: 16), NeoMPS Strasbourg, France) was added prior to reaction, leading to a homogenous covalent tethering of FITC to the matrix.

Within MMP-sensitive gels, endothelial cells were capable of spreading in response to VEGF/HGF. In MMP-resistant gels, endothelial cells remained locked in a spherical shape. Elongated endothelial cells embedded within MMP-sensitive scaffolds displayed oval nuclei observed by GFP-lamin tracking, while spherical cells embedded in MMP-resistant scaffolds exhibit multi-lobed nuclei. Furthermore, genome packaging was regulated as a function of cell shape in 3-D culture with chromatin condensations directed to the nuclear periphery in MMP-resistant hydrogels.

Alternatively, endothelial shape was modulated independently of proteolysis by culturing cells atop micropatterned fibronectin islands printed onto polymethylsiloxane substrates to generate ECM-adhesive patches surrounded by regions blocked with non-adhesive, Pluronic F108 (Chen et al., 1997. *Science*, 276: 1425-1428; McBeath et al., 2004. *Dev. Cell*, 6: 483-495). Microcontact printing techniques were used to fabricate substrates patterned with regions that were coated with fibronectin and regions that resisted such adsorption (Singhvi et al., 1994. *Science*, 264: 696-698). 1225 $µm^2$ islands (35 µm×35 µm) were used to constrain cell spreading, while continuous surfaces of fibronectin allowed for full spreading. Briefly, PDMS stamps bearing the relevant pattern of islands were washed with ethanol, and dried. The stamps were then immersed for 1 hour in an aqueous solution of 25 mg/ml fibronectin, rinsed thoroughly in water, dried, and placed in conformal contact against the culture substrate, blocked with 0.2% Pluronic F127 (BASF), and used under standard culture conditions.

When endothelial cells are cultured atop microprinted surfaces homogeneously coated with monomeric fibronectin that fully support adhesion and spreading, actin stress fibers were formed and the nucleus assumed a spheroid shape with an ordered distribution of nuclear pore complexes. In contrast, when endothelial cells were plated atop 35×35 µm fibronectin islands permissive for cell adhesion, but not spreading, a cell shape-dependent perturbed regulation of nuclear and chromatin structure was observed (Chen et al., supra; McBeath et al., supra). Hence, ECM-regulated changes in cell geometry directly determine nuclear shape and architecture as well as chromatin structure.

This Example confirms that the cytoskeletal apparatus acts as a component of the continuous network of protein:protein interactions that link the ECM to the nucleus. The cytoskeletal apparatus tethers cell:ECM adhesion complexes at the cell surface with transmembrane receptors at the nuclear envelope (Dahl et al. 2008. *Circ. Res.*, 102: 1307-1318; Nelson and Bissell. 2006. *Annu. Rev. Cell Dev. Biol.*, 22: 287-309; Starr. 2009. *J. Cell Sci.*, 122: 577-586). Indeed, consistent with the ability of cytoskeletal filament structure to regulate nuclear envelope architecture, VEGF/HGF-induced changes in cytoskeletal organization and pericellular ECM rigidity were lost in the absence of fibronectin fibril deposition or MMP activity. Apparently, ECM remodeling, actin and microtubule assembly as well as myosin-II activity each play a required role adjusting the stiffness of the 3-D microenvironment in a fashion that supports the changes in cell shape and nuclear architecture required for neovessel formation.

When examining the status of the LINC complex in the 3-D system, nesprin-nuclear envelope distribution was observed to be regulated by the endothelial cell's ability to remodel the 3-D ECM. Furthermore, by uncoupling cytoskeleton-nuclear interactions with the dominant-negative LINC complex protein, GFP-KASH, multi-lobed nuclear shapes appeared in tandem with peripheral chromatin condensation and a reduction in histone acetylation.

The data of Examples 4 and 5 describe a novel functional mechanism wherein cell shape—modulated as a function of ECM remodeling—controls nuclear envelope organization via the regulation of cytoskeletal architecture and tension. Indeed, by controlling cell metamorphosis in 3-D PEG hydrogels or atop 2-D fibronectin islands that artificially restrain the cell shape changes critical to the generation of tractional forces (Tan et al., 2003. *Proc. Natl. Acad. Sci. USA*, 100: 1484-1489; Wozniak and Chen. 2009. *Nat. Rev. Mol. Cell Biol.*, 10: 34-43), nuclear and chromatin organization can be shown to be directly coupled to cell conformation. In vivo, 3-D cell shape is likely regulated not only by ECM remodeling, but by the porosity, mechanical rigidity and adhesive ligand density of the surrounding matrix. Similarly, even under the 2-D-like conditions that exist in the blood vessel lumen, changes in the applied forces exerted by shear flow on the endothelium likely impact nuclear architecture and function (Dahl, supra).

In addition, no major changes in protein synthesis were detected when endothelial cell shape change in 3-D is prevented by either omitting VEGF/HGF or when growth factor -stimulated cells are cultured with GM6001 or FUD. The results suggest that the coupling of ECM remodeling and shape-induced cytoskeletal tension to the LINC complex and the associated lamin-rich inner nuclear envelope plays a role in translating changes in cell shape into signals for macromolecular metabolism. The laminar network of type A and type B lamins directly or indirectly binds chromatin and DNA, as well as a variety of inner nuclear membrane proteins functionally linked to nuclear architecture and mechanical integrity, chromatin organization, gene regulation, and DNA replication (Crisp and Burke, supra; Dechat et al., supra; Starr, supra).

The findings described above suggest a new model wherein pericellular remodeling of the ECM represents a required step in transcriptional machinery activation, which is responsible for controlling growth and differentiation. While the results are focused on endothelial cell behavior, it will be appreciated that the findings have broader applications, e.g., cell populations that reside within a 3-D ECM. By linking ECM remodeling to the ordered transmission of mechanical signals to the nuclear envelope, subtle changes in pericellular proteolytic activity would be predicted to profoundly impact phenotype. Indeed, the phenotype of MT1-MMP-null mice—characterized by a markedly shortened lifespan with a profound reduction in growth associated with the onset of severe bone, muscle, vascular and adipose tissue-related defects—bear considerable similarity to mouse models of laminopathy. The overlapping phenotypes raise the possibility that modulating nuclear shape by interfering with ECM remodeling may impact cell function to a degree similar to that observed by directly targeting the nuclear envelope. In summary, the complex changes in gene expression and cell function known to accompany ECM remodeling are interconnected with matrix-derived cues transmitted to the nuclear envelope, chromatin, and transcriptional machinery by a continuum of protein:protein interactions that span from the cell-ECM interface to the nuclear interior.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A method of inhibiting neovascularization in a subject, the method comprising administering to the subject an agent that interferes with fibronectin (Fn) matrix assembly and inhibits endothelial cell proliferation in an amount effective to inhibit neovascularization, wherein the agent comprises a functional upstream domain (FUD) of *Streptococcus pyogenes* adhesion F1 protein.

2. The method of claim 1, wherein the agent does not promote apoptosis.

3. The method of claim 1, wherein the agent does not interfere with binding between integrins and soluble Fn.

* * * * *

SEQUENCE LISTING

```
<160> NUMBER OF SEQ ID NOS: 16

<210> SEQ ID NO 1
<211> LENGTH: 75615
<212> TYPE: DNA
<213> ORGANISM: Homo sapiens

<400> SEQUENCE: 1
gcccgcgccg gctgtgctgc acaggggag gagagggaac cccaggcgcg agcgggaaga      60
ggggacctgc agccacaact tctctggtcc tctgcatccc ttctgtccct ccacccgtcc    120
ccttccccac cctctggccc ccaccttctt ggaggcgaca accccggga ggcattagaa     180 gggattttc ccgcaggttg cgaagggaag caaacttggt ggcaacttgc ctcccggtgc     240
gggcgtctct cccccaccgt ctcaacatgc ttaggggtcc ggggcccggg ctgctgctgc     300
tggccgtcca gtgcctgggg acagcggtgc cctccacggg agcctcgaag agcaagaggc    360
aggctcagca aatggttcag ccccagtccc cggtggctgt cagtcaaagc aagcgtgagt    420
actgaccgcg ggctgaaaca ggctgcctca gggatgggac cctaaagccg accaaagttg    480
gggctgaagt tttgtgcgcg cgcgtgtgtg cgagtgtgtg cgcgctttac tgagagaaac    540
cagctgtgca cacaaaagga ccgagttttg agcacgctgg ttctgagggc ctgggatgat    600
aagaccgtgc attggaggac gaggactctg cgactttccc gtgttctaat aaattctgca    660
cgttcagatt gtccttctag gaattaacca aaacttgcct ttaaagagaa aaatgatgca    720
tgtctataaa ttttccgtct gggattagtg tggtccttac tgctacttat ttccttctgt    780
taaataattg gtcaaatatt ttcaacatgg gggtggaaag ggggtattga aatagctgtc    840
ttgtttctaa ctaacttgga agagatgtaa ttggttcaga cctctttagg gccgctcagg    900
atacttcacc aagaacagag gttggaattc tttccgtttt tcaaagacac accctccttt    960
tgctttgaga aagctgctta aagttgtcct ttttgactat tactccaaaa gaatatttaa   1020
gttccttgca tgttttaaaa atgtgacttc aattgtctgc cttccaaaat gtttccaact   1080
tttttatgta gacccctggc cagatggaaa tgacatcatt gtatataact tttagcaaag   1140
```

```
ttaaaaggaa aaaaatatgt acgtcaatat tcacatgaag aaaattccat aattttggga    1200
aaaggagaaa tgcaaatgta acgttttcct tcaattattt gcagccggtt gttatgacaa    1260
tggaaaacac tatcagataa atcaacagtg ggagcggacc tacctaggca atgcgttggt    1320
ttgtacttgt tatggaggaa gccgaggttt taactgcgag agtaaacctg aaggtaagtg    1380
acaacaagcc ccatagttag tatcttttaa tacatgaagt ggtaattgtt aaactttgca    1440
ttagtaagta aaaatacata caccattttt ctaatagaat tacctgtcat ttcctcttaa    1500
gtttaaaaac tgcttatatt tgcttttcac atgcttttac ctttaaaaca agaaacgaa     1560 tctttcccaa attagttcct agagtcttct ttttgcttta ctctcccaaa gttttgatg     1620 agaaaaatga agattttgt gtgtcctccg acaaaaaaaa ttgcttataa aattttaatt     1680
tattagaaag cagtctcaaa tcttaaactg ttagtttatg agccagaaaa cactttgggg    1740
acttacatcg taaaatgatt tgtcagcggc agttaacaca aaaccattag ccacttcaaa    1800
gttctcattc ctttaggacc aatgatattt ttctcataaa ttatagcaac tctgtcagag    1860
aagcactgat caggggaaaa tggaaatcat aggattaaca actgtcaagg ccttgtggga    1920 ggtgggatc ttcgaattgt ttgttgtttt ttgttttgtt ttgttttga cagagtct       1980 tgctctgtca ccaggctgga gtgcagtagc actatctcag ctcactgcaa cctctgcctc    2040
cagggttcaa gcaattctcc tgcctcagcc tcctgagtag ctgggactac aggcacatgc    2100
caccacaccc agctaatttt catatttta gtagagacgg ggtttcaccg tattggtcag    2160
ggtggtctcg aattcctgac ctcaggtgat ccacccgcct cagcctccca aagtgctggg    2220
attacaggcg tgagccactg tgcccggcca atcgtttgct ttttatgtga accttgcttt    2280
gactttctga gtcagagatt ggaatgtgaa acccttcaca aatctagctc tgtcataagt    2340
tagtacttta tatggccttt tcctaagagc ctgagatttt tctacaatat gaataattta    2400
cagaaaattt gacaatatgt caaggtcaaa aaccatggcc ttattagagc ttaggataaa    2460
aatctgtatc tctcacttca ttttattctt tgaggtgtac catgttactt gtggaataga    2520
gaagtgggtt ttcctttaga ggggattagt gaactagaaa agcttgtacc taagtgaggc    2580
tcacatggac tttccttttc ccctcagctg aagagacttg ctttgacaag tacactggga    2640
acacttaccg agtgggtgac acttatgagc gtcctaaaga ctccatgatc tgggactgta    2700
cctgcatcgg ggctgggcga gggagaataa gctgtaccat cgcaagtaag gaagagattg    2760
tgtaaaatga tgccaaaata tcaaatatga atttctctgt taccatcact gtcatttttct   2820 gttatccatg actggatatt ccgaactttg aggtttgccc ctggtgacca ggtactctta    2880
agtggtcacc caactggttc ctgtgttttct taaagacggg tatgagcaca gatggaatca    2940
gtgtttgatg tgtgtgcgtt tatgagtgtg tgtgcattta tgagtgtgtg tgtttctgta    3000
catagtagaa ccaagagacc tcttgggttc catttcagta agacatgctt agggagttg     3060 cccattttaa atcacctgga tatcttcaag ctagacaaat catgagactt ttctgcagtg    3120
actgggaagg tgttcatgaa gagtgaacca gccatgtgtt gtctggtctt catgtttgca    3180
atgcagagac ctcttgcacc tcacagaaac agtctggttt cttggtgacc agtaggttat    3240
acccaggaag cagatgtcac tattcctagg gataatacaa aattattaac ccaatagagt    3300
ttgctaagga acttgggaa ccgggctgat tctcaactct agtttagcta aggcactctt      3360
tccagtatga ttcactgggt taccaataga ttctattaag atagtattta agttttttaa    3420
tccattcttt aaatataagt cgtccttaaag acttctattc aaaagaacaa gtcccgtgtg    3480
aataggccca atcaactttc cccatatttc atgttagggt ttatccaagt tcacaggcaa    3540
```

```
atcgcaagag gcaagggtcc atagtgttta caatctagtt cagcatttga atgtgccatt      3600
gggcttaaca acttagaaaa ctaccaggat ttccacactt tatatgcata tgtctgtttg      3660 cttttccacca aaatgacatt tctatcctag ggtaaaatac aggctctcca tgctcccaaa     3720
agctggagtg ctgtgcctga tgtggccttt tcactgaatt agtctcagtc ttagcctgct      3780
gtgtatgagt gaagaccaag cctcccagcc tttcttttct gcttaggacc caatttcctg     3840
tgatctctct gggaaagcag gattcatgac ctcttccttg ccatccagat ttctctgtgg     3900
ttttccattg tgttctaagc aagacactta actgaattga ctccaagtga ccagacctgt     3960
taacgtttcc cctgtctctg atgggaaagc tgttgtctgt gtctctactt tagccaacct     4020
aagtacctac catgggtgga atatgagacc aaaaaaaaaa atctgttctg ccctctccta     4080 acatttcgt tgtatcttca acagaccgct gccatgaagg gggtcagtcc tacaagattg       4140
gtgacacctg gaggagacca catgagactg gtggttacat gttagagtgt gtgtgtcttg     4200
gtaatggaaa aggagaatgg aacctgcaagc ccataggtgt gtgagtctta gggctgagca    4260
agagctggga tgcttagttc taatgtgggg ttggaccaga atcacatcta cataggtcat     4320
agacctgaat tccagtgaaa accaataaag aaatgggaat tttgtttgaa ataatgaatt     4380
attatataat ccatagtctt cttacaggag ttagatcaaa aagtactgac tacacataga    4440
agtcttaact ttgcttcaaa agcataaggt agaattgaaa gatttagaat ggagtcattt    4500
cttttaccta atagctgatc tcagattcct ccttcgtcaa gatataattt atttaaaaga    4560
aaaaaaaatg acactttgga cacatttcta tatggaatgt cctggaccga aacatgaaat    4620
agtgtgtgct tgtcacactc tgctcatttc ttttcaaatt aaaagttgtt gagcttcttt    4680
ggatctcaat cctcagttga attttgtaag tacaagcctg aaagtttctg gctataaatt    4740
ttactctgtt tacttgtctt ctaatttaga ggttttttgtc ttgttttgta ttgttttgct    4800
ttccaatatt taaaaatagc tttctttgtc attgtattta ggccactcaa aattcataat    4860
tggtcattta taattaagat tggaattttg catatgtagt ctcccacaga ctagatacat     4920
acatagatcc ttgctactgg aaatgctgct gggaagtttg gggctcgctg aaaatatgta    4980
gtccatgtac ttattaggag aatggaattt ctgcctgcca actcagcttg agcttttctttt 5040 tgccttggct acttactgtg tgcttagatg ctgggtgtgt cattctttct gaacagagtg    5100
ccacttaaaa aaaatgtggc tgaattttttg cttacacact acactttaaa ttacagggag   5160
cttgcacaat tcaaaataac cttttttttcc tgtttttcttt ccaaatttcc ctacagctga  5220
gaagtgtttt gatcatgctg ctgggacttc ctatgtggtc ggagaaacgt gggagaagcc    5280
ctaccaaggc tggatgatgg tagattgtac ttgcctggga gaaggcagcg gacgcatcac    5340
ttgcacttct agaagtatgt tttacatctt tatgttaaag attaagccag gtattgtttt    5400
ctggattcct agagagaagg gtaatactat gttactcaga acacatccag tatatcagca    5460
tgctttggta acttctggaa gtcaagaaaa ctttcataac caacttattc cgcatcttca    5520
gagaagacta cataaataga aaacatatc actttgataa ggttcaatct cagctcactg     5580
ccactgacat agagttgaac aaaaggttta ggtttccttc tatgtttgaa atttaaatag    5640
ggcacattca caggctaaat tgataaaatt aaaaagaatt tatcccataa attaaaatga    5700
tttatctact ctggagttag ggatagtgtc tctgacctaa cgcatttgat tagtgctgta    5760
aagaagctgg cctctggtgt ctttactgct ccttctaaga ttgtcttggg gtcttaattg    5820
ttgcctttgg gtttgaaggc tccttttttg atattgtaaa ctaataacag ctagagagtt    5880
tgttgaagta aaacagccat taactactgg tgttgtaaat aagtttaaaa tcaaatccaa    5940
```

```
ataatttgaa cctgttttat ttatctagct gaacccattt aactaccttt aacatagcca    6000
tcatccaaat tcaaattctt tgctaacaaa aataggtctc tcatgaaaag tggtaaccat    6060
tttgaccaaa gctttcccag aaacttgctg gtttattaga tattttgcat ttaaaatgtt    6120
actgtgatca tcagacttcc aagatctttg tggcaatatt ttagcttaag acaaattaga    6180
tgtctgattc aaaccttatc tgttatttag aactctttaa atagcaagtt gggaaaagtt    6240
tctcaaagag aagtcattta ttccagaaaa ttttataagg acttactttg ttcaaggtat    6300
tatagggtg cagatatgaa atgaacatta gcccagcctt caaagagtac ttaggggtc      6360
agggagatga gaaagtctta tacatattta tcatctgcaa aacacagtat taaagatttc    6420
aacagaaata ctgaaagtag tgctatggag gttcagggga tgataatact tttcgctggg    6480
gatttgggaa aaagctctaa tcagtaatta taccttcatg caaacttcta ttcttgtggt    6540
agatggatgt gggtgtgtat ttgtttgaac ctacatcaac tattaatttt ttttctctaa    6600
cccaggagtt gcaacaatat ccaattcaca aagacatcag atcctctata ctcacatcgt    6660
ggcacagagc aaatttggat tataatttaa ataatctatt taccagataa atgcacgcat    6720
agactaatgg tcatttagtt acaaattatc attttatgtt gatcccactc ttccagtgga    6780
gggctaacac tgaataattt ggggctattt tgctagtgat ttttaaatac tgtagatgtt    6840
tgggtatagg ggaagggaaa ataatatttt agtcaaagaa attgtgcatc ctctacattt    6900
tttacataac aaatgaagaa agagatacta ccaccttctt atagcttctt tgtagccatt    6960
ggtgaagacc ctttgatacc tgcttgcctc cccattgtta taagcttttt tttgtttgct    7020
tgttttttt gttttgtttt gttttgtttt gttttgaga cagtctcacc ctgtcgccca     7080
ggctggagtg caatggtgtg atctcagctc attgcaacct ccacctcccg ggttcaagcg    7140
attctcttgc ctcagcttcc cgagtagctt ggattacagg cgcccgccac cacagccggc    7200
taatttttt tggtattttt agtagagacg ggggtttcac catgttgccc aggctggtct     7260
tgaactcctg actgcaggtg atccaccctc ctaaagtact aggattacag gcgtgagcca    7320
ccgcgcttag cctgttttta gttttctaaa gcaaggtccc tattgaaagg caggccataa    7380
acagtgatga ctaagaaaaa tcctggaaga gcctgagaag gaaaagatg aaatataatg     7440
ccagagaatg aagttagtca aaggaacagt gtgaaaacaa taaataaata gataaatgaa    7500
aatgttattt gacagagaga tgaaactaga ctaaaccatt cagctgcctt tccactgtaa    7560
caaatgtaat ttcatctttc agaagtgtaa taccttgcag caccagagct gaatatgaac    7620
atattaccaa aaatagatta ccaggcatag atagcattcc ttttttaagt ttgaattgac    7680
cacttgcgac tctcgacctg atgtatgtat gtgcttcctt tgtgacacag atagatgcaa    7740
cgatcaggac acaaggacat cctatagaat tggagacacc tggagcaaga aggataatcg    7800
aggaaacctg ctccagtgca tctgcacagg caacggccga ggagagtgga agtgtgagag    7860
gcacacctct gtgcagacca catcgagcgg tgaggcacag gacgagcagg ggcgggaaat    7920
gggaagcag gtcaagaaat atttccgcaa atccatcttt cctttgacat gccatttgag     7980
gataatttgc agtgtttcag ctaataacct aagataattt acacattatt ggttgttaaa    8040
acttttttta atgtcaagtt ttaaattttt cagaaaaaaa gaaaaatgac atacaaataa    8100
accttagggg gaaaaaagcc agatttatct ccaaaagata aaactgagtt ttaaagaatg    8160
ctagcatcat aaaacttacc atggatagat cacgcacaca cgcacacaca cacgtatttt    8220
gaatatccaa agttcatttg aaaggaaatg agagttataa ttaattatat gactacctgg    8280
ttcttctgct aggaaaggac aaaaaaagtg catttggatt ttttgtttgt tgttttttga    8340
```

```
atgaaatata cttccctgtc ccgacattga actcttttg tagtggaaac catcctttat     8400
atgtggtttc tatgctctgg caaactttgt tacattctat aaagtaacac acaattattt     8460
ccttcatgta ttggcattcg aaattttaga aattcagaga ggacttagag atggccatga     8520
aagacatgat atctaagcat tcttttttaaa aaacaagttt taatcatttt tggcatgaga    8580
aaaagatttt tacgtcataa atgtttcata aaaatctgaa gagagaaata tggccaacaa     8640
ggacgtgcac tcctctcatt attttttaata tgttttgatt aacttttac tatatgatgt     8700
gccaacatca ttacgtagtg tctcagccat ccttcaatta aaaatattaa ttgttctaat     8760
ttttcttctt ttgatgagtt tttgtcttgc tttgagcact tatgaaggtg aacaagatta     8820
gatttgataa tatctttgag ttatttatt atcattaata aaattgctac tggccaaaaa      8880
aaattataaa catcggccac gcgcggtggc tcacgcctgt aatcccagca ctttgggagg     8940
ccgaggcagg cggatcacga ggtcaggaga tcaagaccat cctggctaac acggtgaaac     9000
cccatctcta ctaaaaatac aaaaaattaa ccaggcgttg tggcgggcgc ctgtagtccc     9060
agctactcgg gaggctgagg caggagaatg gcatgaaccc gggaggtgga gtttgcagtg     9120
acccgagatc gcaccactgc actccagcct gggtgataca gcgagacccc atctcaaaaa     9180
aataaaataa aataaaaaat aaaaaaaatt ataaatgtca gtctaccaaa atagattaaa     9240
agtgtaggtg ggaattaaat ggggataaac actcaataaa tgttagctat atgaatat      9300
tgccaatact gaaagattc cattgttcaa aaagtttga gaagcaatgg gttaaacaaa       9360
atggaacctg ctctgcagaa tctgtgtgtt cctttacatc atactctcca tggtagagtg     9420
tagggatgg gcgccatgtc tccctagtac gtttgacctt gggattcttt gtctgtgaac      9480
atctttgggt tctagtgttc agcagcactt agggaggcac tgaattcagt gtacctttgg     9540
tctagcctca gccctgattc tgttctgcgg tgggccctgg ccttcaagag aacagatatc     9600
taaaagttga agaaaagat cggccgggcg cggtggctca cgcctgtaat cccagcactt      9660
tgggaggcca aggcgggtgg atcacaaggt caggagatcg agaccatcct ggctaacacg     9720
gtgaaacccc gtctctacta aaaatacaaa aaattagccg ggcgtggtgg cgggtgcctg     9780
tagtcccagc tactcgggag gctgaggcag gagaatggcg tgaacccggg aggcagagct     9840
tgcagtgagc cgagattgcg ccactgcact ccagcctggg tgacagagtg agactccgtc     9900
tcaaaaaaaa aaaaaaaaa aaaagaaaa aagaaaagat caacacatcc tgttgtgtta      9960
ttctgaaagg aaagctgtct taagaggatc aattggtttt agaaaaaaca caatagaatc     10020
acaaataatc cagaggagaa ataaaatgtg gaaggtggag gtgacctcca gaaaatccag     10080
gacagctgct gaaggcaccc tctgatgagc tcggttactc agaagagtga ggatgtgttg     10140
aaggtatctg ctgtatggag tggcaggatg atgtctgtga ttgagaaata taatcccggc     10200
caggcgaggt ggctcatgcc tgtaatccca gcactttggg aggccgaagc gggtggatcc     10260
cctgaggtca ggagtttgag acaggagttt gaggtcagga gtttgccaac atggcaaaac     10320
cccgtctcta ctaaaaaata caaaaaaat cagctgggca tggtggtgcg tgcctgtaat     10380
tgcagctact gggaggttg aggcaggaga atagcttgaa cccaggaggc agaggttgca      10440
gtgagccgag accgcgccac tgcactccag cctgggcaac agagtgagac cccatctcaa     10500
aaacaaccca aaaaaccaaa aaacaaacaa acaaaaagaa atataatccc agtagcccca     10560
gctgagctgg aggatggaga ccacttggta gacacttgtg gattatttcc taggctaaat     10620
gcaaaagcta ctgctgaata agggacattt ttttccagtc ccaggccagt agcgacatag     10680
atttcagagt gatctctgtg agatcctgaa gatcctgact gcagaaagta gtgaattgtc     10740
```

```
ttctctcacc cagttttgtg acattcccct ttcatgccat taggatctgg cccccttcacc   10800
gatgttcgtg cagctgttta ccaaccgcag cctcacccccc agcctcctcc ctatggccac   10860
tgtgtcacag acagtggtgt ggtctactct gtggggatgc agtggctgaa gacacaagga   10920
aataagcaaa tgctttgcac gtgcctgggc aacggagtca gctgccaaga gacaggtatg   10980
cattatcttt ttgaagaata ggactgatga ctttattatt tagttttttga aggacaatac   11040
attttcaatg tgaaacaata aaacaaacaa gaagcctgta atcttaccac cctgtgataa   11100
caattagggt tggcatttga aatagtttct tccaatcttt ttaatttatg tattttcttt   11160
ctggtcatgg atatcatggg taaaaatttt attgtattta tctgtctaaa gtgttgttac   11220
aagagagcta cttctgaat aatcatcaat gtttatatt ctaaatctca aatttcagca   11280
gctttgtgat gtaaacatct tccaataacc taatatatgt attctgcact acaaacatgg   11340
tagtcactat ggcaataaca attgctacac aattctcccc cagaatagtc tcatatatta   11400
attttatggc atagatatag tcataaatat tatcccaaca tccttaagca gcatccttaa   11460
ttgacctgta taaatatagc tttacaaata gagaaactga ggcatggcag cagaagtggt   11520
catgaaggac atcagcagaa gaactcaggt gtcgttctat ccacagtaga catggattcc   11580
tgagtaatgc atttttgactg aaattaacga gatgatcatc tatactcata gcttcttcct   11640
ttgagggcac aagctcagta tctcattgaa gccataaata agcagctgct ggtgggagat   11700
aaagcatctc tgtttactga cactcttttg attatgattg tagctgtaac ccagacttac   11760
ggtggcaact caaatggaga gccatgtgtc ttaccattca cctacaatgg caggacgttc   11820
tactcctgca ccacagaagg gcgacaggac ggacatcttt ggtgcagcac aacttcgaat   11880
tatgagcagg accagaaata ctctttctgc acagaccaca ctggtgagtg tcccaagggg   11940
gagccacaga agtgagaaaa actcactttc atgccctagt tttatttgcc agcattctag   12000
ccatttattt tgaacccgcc caagaagcat cgcttttgtt cagttggac tcaagagatc   12060
gcagcgctca cgtaacagct gaggattctt ccatcttccc cagtactgtt gggaaatgac   12120
accaagggag tagccttcca gttcatttga tttaacacat tgggattatg atgtgattaa   12180
agatacttgt attttggaat cagtagatga tcccacaggg ctgaggaata caaaggatga   12240
atgttttagt gccttagctt attttccagt taaaacaatg ttttattcaa agctatcatt   12300
taatcttttg tgggggggt gctggggaaa tgacagtgaa agtgggattt aaacctgttt   12360
tgaaggtgtg aaggtaaata tgctaagaag cttagaacta tattatcaga cattttttat   12420
tctgagatag actgtctgtg aatgagctgc agaaacctgg ctctctcaga ccagtaattc   12480
tgtgtacatt ggaaagctca gcggtaatct tttccttctt tgttgtgtat tgttcctggc   12540
agttttggtt cagactcgag gaggaaattc caatggtgcc ttgtgccact tccccttcct   12600
atacaacaac cacaattaca ctgattgcac ttctgagggc agaagagaca acatgaagtg   12660
gtgtgggacc acacagaact atgatgccga ccagaagttt gggttctgcc ccatggctgg   12720
taagatgaag cccttgtggg ttgtcttgtt tgacaacaat ttaggagta gagactaaag   12780
actagtgtcc agtttactcc catttcattc attaacacaa ttttgagaca acagaaaact   12840
tcatgtgaag tgtgtttgtg tgtgtgtgtg tgtgtgtgtg tgtgtgtgat gttacatcat   12900
atacataagg attgggaaga ataattagat aattatttat ataattttta aacctcattg   12960
acatgattta atgtcaaaaa tataattact tatttgtaag tctggaaata tgaatttgca   13020
caggtttgtc tttgtaaaga gcacacaact gagtagctta caacatttaa tatatgtatg   13080
acggctttag tcacagagct acaatattga cacatggttg tggtttgatg ggcataagct   13140
```

```
ctatcactta ttaataagtg ccaaagtgac taaaactcaa tgttttctaa caggtaggga   13200
atctcactct tttttaaag  gtccccagtt tgtatagatg gcgaacaaat ggaaacgaat   13260 acctttact  tgttttcaga tttcaagaac cccatagatt ccctttaatt ttccagttgt   13320
agaaacaaga gcctgggcgg taggcactgt caagtgtgac tatgagacaa agaaattgct   13380
tatactttta tttctttcaa caaaagaaga tgctgagttt agaagaaaaa acccactttt   13440
gcttgtaatt ctatatccaa acccatagtt tttatttgat ccagaataaa ctggaactgg   13500
gaaaagttat gaagctgtag ttaaatccag gcttctagaa cagcaagaac cctttgtgtg   13560
gatgtgtaga tattatctta gtttaacatc ccctaacct  tcctgtaact attttctatg   13620
acacgtttgg actacgtttt ctgcctccag ggctcaaaaa ttctacccct tcacctgaca   13680
gcacttagat gtctttgatg cacacaaagc ttcttcccaa gtgagaattc ttaggatgac   13740
caaactgaac tgatccttt  gcacacatac atgtttagac ctggtgatca tttatcaagt   13800
gcatttctta tccatttcca aacagcccac gaggaaatct gcacaaccaa tgaaggggtc   13860
atgtaccgca ttggagatca gtgggataag cagcatgaca tgggtcacat gatgaggtgc   13920
acgtgtgttg ggaatggtcg tggggaatgg acatgcattg cctactcgca gcttcgaggt   13980
atgctggctg attaacaaaa atatttgaga tggcaaaagg tacagaaagg gacactttt    14040 tttatgaaaa cttgcactat gccaaaagca ggggaagaaa tatggaatgc cacgtcattc   14100
attagtctac tgtgcatggt aagataagcc tgaaaggctt agcaggcagc ctgctaagac   14160
aagcggcata gcaatgctaa tgttctgaaa cactcctagc atgtaagtac ttaggctgag   14220
ccaaaaagat ggcttcaaaa gtaagaatga acatttgat  ccattcagct ttaggctatg   14280
ccactggatt catgtctaga aaagatagga taatttctgt aaagaaatga agaccttgct   14340
attctaaaat cagatcctta cagatccaga tttcaggaaa caaatacata ggggactaac   14400
tttccttgtt cagattagtt tttctccttt gcacccagct atataatatg aggaagtatt   14460
gactttttaa aagtgtttta gttttccatt tctttgatat gaaaagtaat atttcgggag   14520
aaccctgagc tattaataat ctatgtggct agtgcgtaga tattggtctg aatttgttct   14580
ccttttgtgg tgtccagtgg gtaacaccat ccgggagtaa taattacatg tggtgttgca   14640
gaactgaaag agaccttaat aacacataga gacctcactc tatatagatc aaggagctga   14700
gacccaaaaa ggaaaaagta attttctcag gatctctcaa agagtgagca acagagttgg   14760
cctaatttat tttagcgttg tgaatactgt tgacatttta tttcccaaat ctaagtatct   14820 cctcccttc  ccctattcc  agagaccaga ccaccacatc atgctgggtg ttagataaat   14880
atgtttaatc ttcttcttat ttatcctaac aagcagatat ttaaaggaaa ttatcaacta   14940
agcaagaaat tttcagaaag taagacatgt atttgttcaa atactggctt ctcacaggaa   15000
agtgtatttt accacattct ttacttgagc atactgtaac ctctgcaaaa gttacacatt   15060 tgggaagaa  aaaaatttt  ttggcaaaaa ttgtattact gaccaaactt tgaaaaaaat   15120
gttattctat gcttgtagaa aagttatttt agtggaaggt gttgataatt aagtggaagt   15180
agttgtatgc tttgagaagc atacctttt  tctttcatca atggaacttt aaaaagtttc   15240
tcactcaccc acctgtttcc taaacagatc agtgcattgt tgatgacatc acttacaatg   15300
tgaacgacac attccacaag cgtcatgaag agggcacat  gctgaactgt acatgcttcg   15360
gtcagggtcg gggcaggtgg aagtgtgatc ccgtcggtga gtagccctat ttccctagat   15420
gagtttgcac aggggaatg  gttagcaagt ttcagataag aaaagctatg tgaaatcaca   15480
tgactgaagt tggctccaga ctttgatcag ttgcttgcaa agaactttgc aaagtcttct   15540
```

```
ctctaatact ggaccaaaat atctcgatat tggtagtcgt ctggttttttg ctgaatttgg   15600 tgacaaattt aggcttattt taattgaatg gaatttattc ttgggtttag aatcataaag   15660
ataatccatg ctattaaaag tattctttcc tttttttttt gtttgttttt gtttttgttt   15720
ttgttttttt gagagagagt ttcgctcttg ttgcccaggc tggagtgtat ggcacaatct   15780
cggctcactg caacctctgc ttcctgggtt caagcaattc tgctgcctca gcctcctgag   15840
tagctgggat tacaggcatg cgccaccagg cccagctaat tttgtatctt tagtagagat   15900
ggggtttctc catgtgggtc aggctggtct caaactcact tccttaccag ctgtgtaaca   15960
gcatgagcaa agggtgtaaa tatcacccac caaaacactc taggtttttt tttggccgcc   16020
cttcaaaata gaactaagca aatagtgaag gctgagcctt aaaagagctg tgttaccagc   16080
actacaaagt ttaaggtgat ccattactat ttctttacca aaagagacag gttgctcact   16140
gagaaaacaa actgataaca tccgtttgtt tgacgtgaga ttaccagaac tgagagagaa   16200
gcctgagagg ttttcttaga agctgctcag caggtatact cgtaaagtct agttcattca   16260
tttaaatgtc aaacagtttc tttaaatttt gaagaagtaa ggaaaatgaa attattgcag   16320 attttttttct tgctatttaa atgttaagcc agttatatta atatgggtaa aaataataac   16380
taatatttaa aattaatgtg tagattatca atatacactg aaatctaaat ctttacattt   16440
ttatttagaa atattaccctt ttagaaaact aaatattcct cctaataggt actttggttt   16500
tttttttact acaaactgtc ctgtaaggta aagaatgtga acaaaatatt ttttttaactg  16560 catatatttg taagaacaat tgcaaatttc tatttaagct aaatgtatgc tctagcaccc   16620
tgaaattaaa ttcgtagtta taagtcttca aggctgttta tcttttcctt ccatgtattt   16680
tagaccaatg ccaggattca gagactggga cgttttatca aattggagat tcatgggaga   16740
agtatgtgca tggtgtcaga taccagtgct actgctatgg ccgtggcatt ggggagtggc   16800
attgccaacc tttacagacc tatccaagta agtagctcta ttactgcaag ttgagaactg   16860
ccaattgggt tataacaaca gggcagtgat tattaatgct ctcatgccta agttggggt   16920 ctcccctctt tcccaccctt ttctcttgtt attatctaat aatcaattga attttttgatt  16980 aaaataattt ttctctcttc ctctatcaag taaaaggtag agaaggctat gaaaatgtgc   17040
ctgtttataa ttttacttct taactctgta aaatattctg ttaggttaag acactctggc   17100
taatttcatc ttatatccat acatggaaat aaaaaccacc aagtgagtta tgctgggagt   17160
aaaggtttgg ggctttatat tatgattctt aacagagaag ctgcatagag agatggcatg   17220
aaatgcagca taaggtacgt gttcattcaa catgtcatct aagctcccctt tgcatcaaac   17280 ttttcatttg tttgatcagt tgccaccagg aacacagtat gttgggccaa gggttgagta   17340
acttggtcaa ctctctgccc acacagttca aacactctca aatgtttatt gctgggtttt   17400
tccaggtcac aaagacatca tgcctagctg taggtgtaat tagttcattt gggggaaaa   17460 ttgcatttaa atattcactg agtgattata ataaacatg ttaataaaac atgaaaggct   17520
aattaaaagg catcagttat ttgagcaact gctgaggtgc aaagtctcca aagtcttcac   17580
taacgtttga ctgaaaatat ggcctacatt cagaaacaaa agagtttcag ggtgtcagaa   17640
tctgcatgcg acagaaatta agattaactc tgtgataaaa gattcactgt gacagagaac   17700
aagctatggg aacaacttgg ccaaaggtag tgttagccaa gcctcattcc tccatttcct   17760
catctgtaat atgggaagat tgtagctgat taccttaat gttccatcct aaatactaaa   17820
cacccagatg caccttttct aggaacttgg aagattctgc ttttcccaac cctcagacac   17880
tgtcagtgct ggggaaggtg acttcacttt tgaaggctta tagcacagat tgaccaacct   17940
```

```
cctaaattgt atttcttgga ggatttaggt gtaggaatca cttaattttt tgtaacttaa   18000
tatatattta aatctgattg tggaagtact ataagtatat gaatggtttg tttgtttata   18060
tgatgcaaat gatacttaaa tggtagaaac ttctaaaaaa atgctctgtg gtttctatat   18120
ttatgattgt tattggtgtt gcaatttgct gaaaatgatt tccttctgaa tgattgagag   18180
agatcttcgt ctctctcaac ataaggctgt ccacatagct gcttgctgga agcatttagg   18240
tggacatgtt ggagataaaa tctggaaagg aaggaatcct tgagtattgg agtattacat   18300
gttgacctta ctcctactct ttaaaaagga gaacagcaag atcccactga gcatagaggt   18360
gatttcggag ggaagagatt ggaatttgac ctcagatatg ctctttggtg cttatctgta   18420
tgtctggttt gctccgtggc ctagcacgta gggctttaag agtgtggtga gaataaggga   18480
acagcagatt accaacagat tgtctctgag tcctgccttg tttgttcctc ctacagagaa   18540
cttggtagag ttgttcaaac tagcaaaaga taagaggcat ttggtttgtc aataagcaac   18600
tagaaaagca cagatctcag caaaataaat agagaaaaaa aggactgagt caaaaaatca   18660
taaatgttta acttctccaa ggacactact attggaaatt attcatttag actttatttg   18720
aaactaattt taaaagtgta gacattgtac tatctccttt ttttggtatc atctcaacta   18780
ttttattgtt agtttattca tattgaataa gagagggagt aaagatttca caatggcgat   18840
agctagtata tgccaattaa gttaatttaa aaagttatac caactaccag tagcgaaaaa   18900
ggactgtcaa aagtttaaat ctaataatg taaaagatgt cataattttt aacttttctg   18960
tctttaaagg atacatagta taagctagag taattatacg tagtataagc tagaatatag   19020
gaatttaatt gatctaagaa ataactgaca caaagtctct ttacttcctg aacaaaaaca   19080 tgctaaaattc catgctgttc agtccatttc ctttaaaggt gggctatgcc acagggctag   19140 atttttaaaac gtggaatttc acaccagtgc tcgaaatctt atgaaagcaa aagggacctc   19200
tgtagttgta ctccactttg gcttgagtaa aaaccactgc tgtacccttt ttctttcctt   19260
tccctgccca tttttatcct cctccttgtg tccttgtgga catagaaata tgattaggct   19320
tagaggtgaa cagtaaaggt catttatgtt atcttttcaa aacttaatag acatttatcc   19380
atcataagct tgtcccccct caaaatcatg attgacaaga ctaaataaag tgtatatcag   19440
gtgtctcttt atggaggaaa ttgtagtagg atttatttaa aggatcaata tttaaatagc   19500
cctatgccaa ttatcataaa taattaagga catgatattc ctagctttcc tgatttacat   19560
ggaagtacgt taaatagtca catctccaaa attttttcttg aatagttgtc tttaaaaatg   19620
tgtttacatt tgtaaggatc ttcataaaca gaaggggtaa ttcaaagata ggcatggaat   19680
tgacttatgc caattgatta aaacaaacat cctgtgtgtt ctgtgaaata catacaactt   19740
taaaatgaaa aactcataat tttatgcatg aattttggtg ttcatgtggc ttggaaatat   19800
gtgcattaaa tggaattaag attcaaagta tttgctaatc ttcaaccaac tttgaattgt   19860
tactggtgtg gaagtgagca tattgtttta gaatttctga atctacatgg atatccaagt   19920
tatatatttt ttctgctaca gaaagctttg ttttccaaga gaatttaatg gcttagataa   19980
taaagtttga aaatcaatgt atttttttttc ctagaagctt tcagaaaact taaatctgtt   20040
aataatctgg tgaagtgctt tattacacat acaaaattttt gctctgtttg acagagtgtc   20100
agttagaaat tcttgaaaag gttactataa gacacaattt ttatttctag taatttaaac   20160
attgactgac atcataaaga tagtgtttta agaaaagata gttttctgtt ctgcaagcat   20220
aaattttcta gctatttcat tattatctta aatggagtta acactactta gaaattgatg   20280
ctacttccct tattttcctt ttattttaaa caaaagaacc aaaaccatac tttaaatttt   20340
```

```
gttgataaca gtgatataca tcaaggtgta gaaatactga atttagtata cacttcataa    20400
agtcatttct gttgacaact gattttggaa aaaaaataaa tttaatcact taataatttg    20460
atggatcaat ggtgtgattt gggagtaaac ttcttgaata aaaataaaac ttgatgtttt    20520
ttccaaactg atagactgct tagactgatg agaaataaaa ctaggtcttt aattattacc    20580
tttgctattt gtctaagatt ctaccccat ttagaaatgt gtttgtttta catcatctca     20640
tatggccttt ggaatgttgt ttccttctta ggtagtagat tcattcttga tgaaaacctt    20700
ccaaaattag aatttgcttt aaaagaggct caatacaata agtaaatgaa gtctgtgttc    20760
tgtattacat tatttttgta ggatcgtttc acaattttct cacaattctt actttgatag    20820
tagagaaaat aaaagcaagc caagagactt ttttttaaaa atatatttta tttgctataa    20880
acaactatga tttgcatttc tcatgtgaag aataataatt atcggctaaa aatggatttg    20940
ctgcattgat tttcaacgta aatatttaaa agattaatgc cagataattt tattatactc    21000
acatttaacg acaagcaaag ctgtttataa tgatgactgt ccatgtacac agttttaagt    21060
tgaagtgagt gaatattcaa gataattaaa tgctacatt tcattttcag gctcaagtgg     21120
tcctgtcgaa gtatttatca ctgagactcc gagtcagccc aactcccacc ccatccagtg    21180
gaatgcacca cagccatctc acatttccaa gtacattctc aggtggagac ctgtgagtat    21240
cccacccaga aaccttggat actgagtctc ctaatcttat caattctgat ggtttctttt    21300
tttcccagct tttgagccaa caactctgat taactattcc tatagcattt actatatttg    21360
tttagtgaac aaacaatatg tggtcaatta aattgacttg tagactgagg ggattttggt    21420
tttggttttg ggtttgttt ttttgcggtg gggggctgg tatttggaag aatttagctc       21480
tttatgttac agaaatcttt tttgcaagga cttagaaatg ataatgctta agattgttct    21540
tgcccaatgt gggaagagaa tctaaggttt ttatatgtct tgcaacctca tcaaaggaaa    21600
attactggca tcattttcat aatttgaaaa aaaaagccaa attaatatat ttcttttttg    21660
attcactttt taagtgatca tttttaaaac tttacttttg acccactgaa tttatttaga    21720
tagaaggaaa agagatgatg ggagggaagt ttagataaag gatggaagtt ggttttattt    21780
aaacaatagc cctgtgattt cctaatgaga agtgactaga aattgaagaa accaaataag    21840
gaggatattg gtcaatttag ctttagtttc tcttactctc tcaagcctgc cctgtttaac    21900
tccaaagttc atggctcata atttgagaaa cactgtttta aacacaggag aaaaaaatgt    21960
ccattttaaa tcatagctat tgaattctac aattacaaag aaacaaacaa acaaaatttg    22020
accaacccag gcggttaaat ttaaactctt caggaaaaat ttaagctgtt aaaattattc    22080 ttttctaaa tttctaaagt ggagggacag aattttcag atttaaaagg gcctcctagg       22140
tgcccagaaa attagtggaa agaaccacgt ctagacgcat ctttgatgtg tcagagttcc    22200
aaggataaaa agaaactttt aaagtcttct atactcagcc aggttatcaa tcaaatatga    22260
gggcaaaata atattttcag acagatttta ggcagtttat cttccatata tcctttcctt    22320
taagggtatt tgtagataca ctccagaaaa acaagagtga aatatgaagg aagttgtggg    22380
gtccagcaaa cagtgcttcc aaatcagacc cctgatagag gtggaaaact ttgcaatgca    22440
acaactgcgt agctggctta gaggacagcc aatacagatg gaacagaaag atgaggatgg    22500
gattgaggga tcagggattg aggtctccaa gaataaaaag ggacttcatg gaaaaagtag    22560
gcttgtggat aattaatcac aggggcaaat aatgcagtta aaataacaac atgacaatca    22620 ggtgaggaa tgtataataa acccaaatgt ggctgggtag agtggctcac acctgtaatc     22680
ccagcacttt gggaggccaa gccgggcaga ttacctgagg tcaggagttc gagaccagct    22740
```

```
tggccaacat ggcgaaaccc cgtctctact aaaaatacaa aaattagcca ggcttggggg    22800
cgcacgcctg tagtcccagc tcctcaggag ctgaggtagg agaatcactt gaacccagga    22860
ggcaaaggtt gcagggagtt gagccaagat cgcgccattg caccctagcc tgggcaacag    22920
agcgagattc tgtttcaaaa aaccccccaag tgtattataa ggcaataatt cctatacgaa    22980
```

Note: line at 22980 reads: `agcgagattc tgtttcaaaa accccccaag tgtattataa ggcaataatt cctatacgaa`

```
gcaaactaaa atgcagcaat attaaggtat aaaaacaaag aggaataatt ccattgaacc    23040
ttgattctgg aaactttgat ccacccagca gtcatgatgt tagactcatt gaaaagaatg    23100
tatttctaat gcatgatgcg atcggtctat agatgtgtca tggaaacttg gttgcaactt    23160
caagacaaaa taaaaagtaa acatttacat gaaaaatggt ggatatggaa ggtggagaag    23220
agaggagata acagctttat cttcaaaat agagaattga gagatggtac caaaagctga    23280
tgaagtaaaa aaaaaaaaa aaaaaaaga tacttaatat aatactttaa attacaaata    23340
taaacacaag aagaacaaat ataatgatac aaatgtcaga cactgggaat gtccaagatt    23400
ctggaaggaa agggtggtat tattgagcta atcctcaac tttgtctggg cacagtggct    23460
aaaaattagc cgggcatggt agcatgcacc tgtagtccca gctacttggg aggctgaggc    23520
ggaaggatcg cttgagcttg agaggcgaa gttgcagtga ccaagatgg cactactgca    23580 ctccagcctg ggagacagag aaagaccctg tgtcaacata ataaatata taaataaatc    23640 atcaagtctc atattaaaga ctctgtaaat atgacttatt gttgacaaat gaaacaaata    23700
gaggtgtaag catgttgtct acatggaggc aagaccagaa taatagaaaa tggaaacaga    23760
ttcccttaaa gaggggaatc gtgtctttct cattggctca atgtagtctc cgtagagtct    23820
agaatgcttc agcacctggc acactgctta acaaatggtg aatgaaaaaa aaaaaaagaa    23880
aagtcattct ttttcttctt tcaccctatg tccataatct ggccatttgc agaacttgat    23940
gtccagtgat cgaaatcaac agcatcagtg catccaatat cttctagtct ctcatcttct    24000
tattacatca ttaattttat ttactttaaa attaaggata tccaaagtat tatgtgagac    24060
cattgcaatg ggagacttaa aagtggtata aaatgtactt tgggccaggc gcagtggctc    24120
acgcctgtaa tcccagcact tgggaggcc aaggtgggcg gatcacgagg tcaagagatc    24180
gagagcatcc tggccaacat ggtgaaaccc cgtctctatt aaaaatacaa aaaattagc    24240 tgggcatggt ggcgcatacc tgtaatccca gctactcggg aagctgaggc aggagaatcg    24300
cttgaaacca gaaggcggag gttgcagtga gccaggatca cgccactgca ctccagcctg    24360
ggcaacaaga gcgaaactcc atctcaaaaa aaaaaaaaa aaagtacatt gaattggaaa    24420
gtcttcaaaa agcagcagtg atgaattttt tgagatttt aacaattaca aaaattcagg    24480
gtttttctta atggatgcca cctgagactt tattttctgt tatttcttg taataactaa    24540 ccaaacaagc tcatgttgaa aaatgattac taaatttgag ctaattgcaa tgactggttt    24600
caaaattttc cacagtgtat ttgagttaaa atttcactgt gaagagtact acgatcactc    24660
tcgcttattc caaaaatata aatggacact tgagtatttg aattattgag gaaatggttg    24720
actgggtaat ttttaaaaat cactgggcac aaaaaatata ttttgactta tattagttta    24780
gagtatttac acttgaaaga gtctcatctt ttctgaaggg tgtttctttc atacacattt    24840
tattgcactg agttttgtga cccatggcat attaatgaag ctgaacagga tgtgaaatat    24900
aaactggaag caaagatta aataaaccaa aattgcattt tttctgtagt cttgtccaaa    24960
attgggtaac cacttctgat ggggtagctc atatccaaga atgagtcaca aaaccagact    25020
cgttgaacct ggtatatgat gagtcacaaa gcaacattct gcctttgttt tttcaggaca    25080
agaaacttga attgtatccc actgagttaa aagataaaat atatggcatt ggcatttctg    25140
```

```
tacttcagag aggaatatat ctgtttgtgg taggaataaa aaataagtga gagaggcaaa   25200
gcttaggttc atcatattat gttactgata taacacaatt aacttggtaa aagtgaaggt   25260
gtgggtgggc gtggtggctc acgcttgtaa tcccagcact ttgggagtcc gaggcgggtg   25320
gatcacctga ggtcgggagt tcgagaccag cctgaccaac atggagaaac cccatctcta   25380
ctaaaaatat aaaattagcc aggcatggtg gcacacgcct ctaatcccag ctactcggga   25440
ggctgaggca ggagaagcgc ttaaacctgg gaggtggagt ttgcagtgag ctgagattga   25500
gccactgcac tctagcctgg gcaacaagag caaaactctg tctcaaaaaa aaaaaaaaa   25560 agtgaaggtg cccagtgtct gcaactatgt caccccgggc atatcacata tcactctgtt   25620
tttccgtctg taaacgggga gcaacaatgc cattgcctta tcatcagaag atatggaga   25680 ctaaatggga gaatgtaggt aaacagcaca gagtatgggt atcagtaagt aaactgcagc   25740
agtttgttga tgttaacaat agttagcatt atatctaact atatctaacg atataaccat   25800
tgggaatcca gttttccatg atttttcctct agaatggagc tgcctaagtc ctgcttaagt   25860
cattttctct tgaagattac tgaacatcat cttcaaatgt tcatccttgt aaacacgtgt   25920
gtgtgtgtgt gtgtgtgtta atttaaattt tcagaaaaat tctgtaggcc gttggaagga   25980
agctaccata ccaggccact taaactccta caccatcaaa ggcctgaagc tggtgtggt    26040 atacgagggc cagctcatca gcatccagca gtacggccac caagaagtga ctcgctttga   26100
cttcaccacc accagcacca gcacacctgt gaccagtatg tacacaacca ccctcatgcc   26160 tcctacccc gaggttccta gagctaggct ctcctgaggc aatgctttcc ttctcaattc    26220
atattcttcc aggaggggca ccaacgtttt ttaaaatgat gttggcgacg aggacggtaa   26280 atttctaga tgactgaagg ctgacttcc ccttctgtg actctctagg caacaccgtg       26340
acaggagaga cgactccctt ttctcctctt gtggccactt ctgaatctgt gaccgaaatc   26400
acagccagta gctttgtggt ctcctgggtc tcagcttccg acaccgtgtc gggattccgg   26460
gtggaatatg agctgagtga ggagggagat gagccacagt acctgggtaa gctcaatatg   26520
tcgctcaaga caggttcagg gcagctgctg gaaaactctc cttgtggggg tgggtggcct   26580
ctaggcaggt ggtatctgtg gtttggaact ggttgacagc tcagactgaa caaaccaccc   26640
tctggcatga ggaagggaag gactgactct ttctaagaag tggccgggtt tttcccaagc   26700
cactgtcaca tgttcctggt ccctgatgcc agctgcatca tgcgcctacc tgtgcacaag   26760
ttcctacagc aaaagctgtg ttcttggtgg aagtaattac caggactgca gctgacaatg   26820
tgagcacagt acggtcactc atacttttca aattgttatg gtgagggcc tttaaaaaac    26880 ttcattggcg cactgaagtg tgtgccatcg taagcactga gttcagtgaa tttgaattct   26940
tataaagtga acacaccaca agaccagcac ccagatcaag gaaaagaata tctctctacc   27000
ctcaccccat catcttccgc caataatcac taccctgact cttactgcag agagctattt   27060
ttaaaaattt ggcattcgat tacaaaaatt atacgtcttt agaaaaaaag ttggaaaaat   27120
gaaaggaaga aggaggagga ggagaaagga gaaagacaag aagtggtgtt tccccatagt   27180
acattaataa tcacagatta ggtgggtgcg gtggctaact cctataatct cagcacttcg   27240
ggaagctgag gctggtggat cacttgaggc caggagttcg agatcagcct ggccaacatg   27300
gtgaacctcc atctctaata aaaatgcaaa aaaatagcc gggtgtggtg gtgtgcacct    27360
gtaatcccag ctactcggga ggccgaggca gaagaattgc ttgaaccgga aaggtagagg   27420
atgcagtgag ctgaaattgt gccactgcac tccagcctgg gcaacacagc aagactctgt   27480
gtaaaaataa taataataat cactgattag ctattagcac attaccttct agtcgctttt    27540
```

```
ccctatgaat atataattct taaaatatcc ttcttataag ctgtagagtc atttgaggga    27600
ctagtttgct ctgattagtt accttttctt ttcatttcaa agatcttcca agcacagcca    27660
cttctgtgaa catccctgac ctgcttcctg gccgaaaata cattgtaaat gtctatcaga    27720
tatctgagga tggggagcag agtttgatcc tgtctacttc acaaacaaca ggtacatgtg    27780
tgctacatag tgttaaaaga atcttttttct gtaaaacaca ggcctgtagt agcacttcct    27840
gactgtttgc cccactttct ttcttttctta gcgcctgatg cccctcctga cacgactgtg    27900
gaccaagttg atgacacctc aattgttgtt cgctggagca gacccaggc tcccatcaca     27960 ggtcagctaa gcgtccccct ctttggctgc tatgttaatc ttaatgacat cagcagggag    28020
ggcgcagatt ctgactgcgg acctgcatat cactttaaat ctccaatata atttatggga    28080
gaggggtttg tgtgtgtgtg tgtgtgtgtg tgtggcgggg gtgggggagt tattttctat    28140
ggcacatttc cccttgaaac catttcacca actcccttat acacacacac cacaacatac    28200
acacaacctg taaagccagc tcattggctt attaaagcaa gtgttcccag ggttgaagag    28260
gtgtaatttc ctgaaaacgt tgctctaaga tttatcctta aggagaaagc tgagctgtcg    28320
tcttagctca ttaggtgatt caactgcctc atcactgaag ttccaaaaag acacacacag    28380
tgctagacaa ctctgcttag gctggttcat taattgcttc cctcgtctgg agctcaaaga    28440
ggaaaaatca gcttaacatg aatattttca cctaatggca tctctaattg acatttatta    28500
aggatgtcag gtcttcaagg atgacattta ttattaaaaa ggttcgcatg actgttctta    28560
ttttatcttc gtgctgaata gtcattatta gaagaagtgg caatattcaa agagtcaaaa    28620
agtatcactg gctcttcact aatcaagcaa gatgctaagg gatattagaa aagggaggat    28680
ttatggtgtt tctaagcctc tgtctcaaag aaaacagtgc atcttacttt tgctcatgaa    28740
tctgcagggt acagaatagt ctattcgcca tcagtagaag gtagcagcac agaactcaac    28800
cttcctgaaa ctgcaaactc cgtcaccctc agtgacttgc aacctggtgt tcagtataac    28860
atcactatct atgctgtgga agaaaatcaa gaaagtacac ctgttgtcat tcaacaagaa    28920
accactggca ccccacgctc aggtaacttt tttaagaaga cacttcctat gttatcttat    28980
caggattgtt cctgaaggag ggttgttttg tctctgtcaa cagtcctctc attcaagaaa    29040
tcttatatat tagttttttcc ctaaacttct gatatttagc tgaaatgtca taagtaactt    29100
atcaaagctg gctactggcc tttctgatta aaaactgaca ccataacgtc catctacaaa    29160
ttttccccta gaagcttaag ggtcatttca tttttgattc ttaagtatta taaaatgatt    29220
cagtaaaaca aaaactgtta cattattttc tgcagttatt tcaaaggctt tttctaaaaa    29280
attttttagt atcttttctt ataaccctct ccccccacca ccatatgaca cttcatatgc    29340
tggtaactca cttattacct attttagata aaaggttcaa atgtcataat ttaagcacta    29400
tgactggacc atgaaaatgt gatctgatta agagacaaaa cttagcaaaa ctctcgaatg    29460
agaggctcaa tgaactgcct aacatatcca agaaactggc ttcttaaaag taatcttcag    29520
cagagaatgt gaatgaccag ttgactcttg tctgtcagat acagtgccct ctcccaggga    29580
cctgcagttt gtggaagtga cagacgtgaa ggtcaccatc atgtggacac cgcctgagag    29640
tgcagtgacc ggctaccgtg tggatgtgat ccccgtcaac ctgcctggcg agcacgggca    29700
gaggctgccc atcagcagga acacctttgc agaagtcacc gggctgtccc ctggggtcac    29760
ctattacttc aaagtcttttg cagtgagcca tgggagggag agcaagcctc tgactgctca    29820
acagacaacc agtatgtctt ctcctatctc tatctcccct ccaaattctc caccctcact    29880
tgcagcctgt gagaaagtgc agtaaaccat tcactcagag gtgtatggct tagagagagg    29940
```

```
gaaatacccca gccggcaagg gaatgcatag tgaacacaaa gcacattaaa cttgaaaaca    30000
aaactcagac aagctccatg gatgctaagt ggtaacccat ttctaaaata catgtaccag    30060
ctgaagggta ctaagagggg agaactgaag agaatctaat ttgagtgcat ttttcgtgta    30120
actaaatata tctagatcaa agttaaaatg caggatcata acacttagag tagaattcat    30180
ttaacaatag caattgtcaa gtgtctagta ttactagcca ccagcttatc tgctcagttt    30240
ttacaagcat tattctcata tttactcttt gttttgacct taggaaggaa ggtcttatta    30300
ttattatttt atttatttat tttttgaga tggagtctcg ctctgtcgcc agggctggag    30360
tacagtggca ccatctcagc tcactggaac ctctaccacc tgggttcaag caattctcct    30420
gcctcagcct cccgagtagc tgggactaca ggcgtgtgcc accatgccct gctaattttt    30480
gtgtttttag tagaaatggg tttcgctgtg ttggccaagc tggtctgaaa ctcctgacct    30540
caagtgatcc acccactttg gcctcccaaa gtgctgggat tacaggcgtg agccatcgtg    30600
cccagccgga aggtcttact agtatccgta ttgaatactt aaagaaactg aggctttaaa    30660
aaagttctgc aacttgtagg gtcacagaga taggaaggga tagagctggc tctataacct    30720
atgtccgaag cccatgctct caattattat actcgactgc ctcttaaaga tttcctctat    30780
ttgaaaggta atttaaattt cggtgggaaa actgctggtt attattctca agaataaact    30840
ccacaactta tgtgattctg atagtgcaaa ctcaccagta tcctaccatg aatctgagga    30900
tacgttatca ttactgtaat tactgtctaa tctgaaccat gtgaaaataa cttttatttc    30960
tctagcaaag ggctattcac agaatattgc ttttgaccca tagagagctt cttcttgctg    31020 tcatttagg aggcatatcc cttttttcctt aatctgtttg gctcagagct aactgtgaac    31080
ttcagaagtg ttttgttttgc cttttttaaaa ataccattgc tttaatgtaa ctataatttc    31140
tgagactgat gcgaaagtct tgctggaaaa ttagacttcc caaggatca cagtcaagca    31200 aaatggttcc acaatttctc atgactggca gagttttggc aaagttttgt gtagcactca    31260
atctcttact ggctcagttt ttccagggtt ttgacttttca catagttaca accttgagga    31320
gagaaaactt agacattcaa tcaagtttca ggacttgagt tatgatcatt actgatctaa    31380
atatttcttg gcatgtttca tcttttttcc tagaactgga tgctcccact aacctccagt    31440
ttgtcaatga aactgattct actgtcctgg tgagatggac tccacctcgg gcccagataa    31500
caggataccg actgaccgtg ggccttaccc gaagaggaca gcccaggcag tacaatgtgg    31560
gtccctctgt ctccaagtac ccactgagga atctgcagcc tgcatctgag tacaccgtat    31620
ccctcgtggc cataaagggc aaccaagaga gccccaaagc cactggagtc tttaccacac    31680
gtaagctgaa aattaagtgc ctttttcttaa ctatatttac attctctatt cttcatgctt    31740
taaaacaaaa caaacaaaa caaaaaaaac attaaaaaat tagtacataa tttaaatcag    31800
tgatactaaa aatgtgctcc atagactggc tgctggcccg ttaattgttt gctgctagtc    31860
tgcaacaaga aaaacggttg tgccagaacg taaatcacaa agcacactgc ttagtacagc    31920
tgagaatttt tctgaagcca gattttcttg atgaaggaag cagtgtgtta atttgcacac    31980
attgccaagc tcgctctttc ctctagggcc agcactttga gtaacatggg tttaaagcag    32040
tctgttatta gaaaaattaa attcgattac attaaatgaa tttaccaaac actagttaac    32100
gcaagaaaaa attagcacct atgtctcat tctattactt tgggcattga atagtaacta    32160
taaatgcaga ataaaaatat ctatggattg aatgggaacc aactaattga acatgaagcc    32220
aaggaaatga tttctttatg agtgttggct gcagaagatt aaagtacttt tgcagacgga    32280
atcgctcttt tcttaaatta ctcttgaaat tcctcagagg agaaaaatac taacaataat    32340
```

```
ttttggtcat gtctatcctt ttgctcaaca ttttaaagga agtggtctta aatctcccac   32400
atatctacat cacaataaca acctctattc acaaaccgat tcctattaaa tacatttcca   32460
tttacattac agagaattat gagactcctt atttctagct gaacatcatt tgttattttc   32520
aactcgacat tttgaattat agaagcacct aacataagta cttttcagc atatattcta    32580 accatggact agtttgcaat tttctaagag cttcaacaa atgttactct tcgactaatt    32640
taaaagtatg gatgttaaaa agcattcaaa aagtccatac aagcctagtt tgtaaataac   32700
tatggaattg atttcccaaa gaaaatacaa acttttcccc ataagaattc atactttaag   32760
aaaaacttac ttccatttaa atttactgta tgaagtttgg ctcatgaagg cttttttccta  32820 aataatagtt aatcgtaagc aagtaaaatt cacttttaat ttgcaaataa gcttacttga   32880
aaatttggct aaaattttac acggttctaa gatagtctaa gatctactct catgaaatta   32940
atgtctttat atttcttgta aatattcatt tcttataaat gtccttcagt gaattagaat   33000
ggagatttca gtgaatgcgc cctttcagta gatgtcgtct tttactaaaa tgtagaattc   33060
tatagttgtc ttgttcattc cttaacatga gacatatttt atgtagtttc ttttgttgaa   33120
cacagtgctt ataaaagaaa aagcattttt aatgatgcta acaataatta agggaaggtg   33180
gtgggccaag atatttcaag tacttctgaa gactgatata ttggatatat tattttatgc   33240
tttgcataat acattcatat aaaatataat gattttaact gaagtactga tagccaaaac   33300
taattttatt agataaaggt taacatagtg tctggaacat tgtatgcttt caaaaactat   33360
ttggtgaata gataattgag aaaggaataa taataaaaac agctaaatga agcttatatt   33420
taaataaact aatgtaagca gggtattcta caactccatt tgaactttaa gcactcccta   33480
aggctgtaaa catccacaag gcttgcatgt ttttgaaatt actaaatttc tgtagttttt   33540
tactatctta ctaagctgaa ttctgggagt aacttttctg agtttataa cttgtgctaa    33600 attcttaaga gcaaatgtga gaaaagttag gggaaaaagc tgtttctggg gaaaattcag   33660
cttagtctta tattgatagg gcaaattttta tttctttaac agctgggctg ttcttcccta  33720
acaagacctg ccagaaccca tagctcacac ttagaatcac atcctttgtt tgacatcgtt   33780
tgtgggtttg tggtttggtg attttcccat aatggccttc ccaggcagag agcatcatct   33840
taaacttggg aagactctag gtggctggct caagcaatag aaaataccta gtcttaaagc   33900
ccaggacagt tgaggcgaat ataatttgta aaaaagttg tggttttcac agatgttcag    33960
tgaaagaaac tgactgttct ctgaattgtt ttttgtgggc cattaaaaat ggtcacacag   34020
ggctggccat ggcattttgg cacagtcacc agcagtcaag tggtgtataa tttcagaggt   34080
actaaaaggc atcgggtcac ccatcccagt catgtccccc cacccccac caaacaccat    34140 caaaataata acatacatag atgaaacagc ccactaaacc agtagtacct caattcagcc   34200
attagagcta tcattatgaa gtggcccaca catatatttg gcttttctc acacaatatt    34260 tttaaaataa aaataaaaaa tggctcctta gaatccagac tgaaaaaaaa atgcgagaat   34320
tgcgatgttg attctaaatt cccacatggc aaagaaaaaa aaattgactg gagttgagtt   34380
gagactggag tctgaacact ttttaatccc tgtttgtata actctggaga ctaattcttt   34440
gtcttgccag ccattcataa tttagtataa atgcattcag aggttttttc ccaatgggaa   34500
caaaatttga ttgagatgta aagagaggaa gaattgtgga gatgtcaaac atgtgaccag   34560
agctatgaac acacttgata cccttgaact taaacttacc caactcaaaa tatctggcct   34620
tctgcgatct tacctttcta catttataat aagatttgca aggttgttgg aaatctctat   34680
cttaacttta tatatacatg cctctttctt tcttttttctt tccttcctt tccctttctt   34740
```

```
tctttctctt tccttccttc cttcctttct ctctctctct tttcttcctt tccttcctt   34800 tccttccttt ctttcttcct ttctttcttt ctttctttct ttctttcttt ctttctttct   34860
ttctttcttt tctttctttc tctctcactc tctctctctt tctttcttc ttattttgg    34920 tgctaaaacc caaaacaaat cttttattta aaataagat ttttttttt tttggccagg    34980 tgtgatggct catgcctgta attccagcac tttgggaggc cgaggtgggt agatcaccta   35040
aggtcaggag ttcgagactg gcctggccaa catagtgaaa ccccatcttt actaaaaata   35100
caaaaattag ctggatgtgg tggtgggcaa ctgtagtccc agctacttgg gagtctgagg   35160
caggagaatc acttgaaccc aggaggctga ggttacagtg agatgagatt gcgccactgc   35220
actccagcct gggtgacaga gcaagagtcc atctcaaaaa aaaaattgtt taagtaaaat   35280 tttatttct ttcttttttt ttttttttt tttttttgag atggagcctt gctctctcac    35340
cctggctgga gtgcagtggt gtgatcttgg ctcactgaaa cctccatctc ccaggttcag   35400
gtgattctcc tgcctcagct tcccaagcag ctaggattac aggcatccac catcacacct   35460
ggctaatttt tatatttta gcagagacaa ggtttcacca tgttggccag gttggtcttg   35520
aactcctggc ctcaagtgat tcacctacat cagcctccca aagtgctggg attacaggca   35580
tgagccactg cgcctggcca agtaatatt ttcaataaga aaataacag tgatgtcagg     35640 atgctagaaa atgcaaaata aatttgttat aattcctgat tctggtgata aaatactaaa   35700
tttttgcagt attattctga aagaataatc acgtatttaa agtacaaatc tttagacttc   35760
aaagtgcatc catggtggca gattttgttt aacttttata tagcatcttt tattgcaacc   35820
aaaaatagct gaccattatt gtggaataat tcagcgtaaa gcttttttt tttctttttt   35880 tgagacggag tctcattctg tcacccaggc tggagtgcaa tggcatgatc tcggctcact   35940
gcaacttcta tctccagggt tcaagcgatt cttgtgtctc agcctcccaa gaagctggga   36000
ctacaggcat gagccaccat gacagttaat ttttcatatt tttaatagag acagggtttc   36060
accatgtttg ccagcctggt ctcgaactcc tgacctcaag tgatccaccc acctcggctt   36120
cccaaagtgc tgggattaca gtcatgagcc accgatcccc gcccagcata aagctgtttt   36180
tagatcacct tctataattt accattgttc ttaaattaat ggttaagaaa caatatgata   36240
atcagtttgt ggtggccagt tttacatttt ataagggatt ttacactgac gatatagga    36300 aatttattgt catcaaagtc aaatcccaac aatcataaaa agacatgaat tagattatat   36360
aatttcaatg aaaggaccac cttagcaaac atctaacccc ttgttactca ggtatcattc   36420
acgggccagc agaattggta ttatctgtgt ttgtcagaaa tgcaaactcc ctagtttttt   36480
gttggacctc cagaaacaga atctgcattt tagccagacc ccagatgatg tgtgtggcac   36540
attaaagatt gagaagcctg atcctctccc aattctcacc caatgaaaaa atatgttaca   36600
tcctctatcc actgcttggt taaactgagg ttctccataa aaatacttgt tatctatatg   36660
ctatgcaatc atctgtgagt ttgagttttg aatatgtgca ttgattctct ctcacagtgc   36720
agcctgggag ctctattcca ccttacaaca ccgaggtgac tgagaccacc attgtgatca   36780
catggacgcc tgctccaaga attggtttta aggtaaactg cagatgttcc taatctctgt   36840
gatacagccc tgagctgtcc ttgtggttcc catgtagtgg aaacagggtg ctcaggagtc   36900
aggagacctg ggttttgtca cctgcttctg tccatacatc tttgactaca ttgtcagggc   36960
ctaacagtcc ttccctgcct acctcactga attgttggaa gggtagatgg aggctgcgaa   37020
agtgttttgc aaaggataaa acattagcac gaagctgctg cttattgtta tcttattttc   37080
tctatccttt cctgcaggga attacatttc aaaaaaacat gggaaaactt tatttgatgt   37140
```

| | |
|---|---|
| gttgttctaa atgagtgtga acaagttcac aaaagccagt ttagggagac cagttaaact | 37200 |
| cagagtcact taaaaatcgc attttcatcc aatcagtttc atctccaact gttcaaagca | 37260 |
| ctgagggtga atctcttaat agaagttaag attaaggttt ccctgtggat atctggattc | 37320 |
| atcttcttta aagtaatgat attagggaag cggtgaatac aaatgaatat gtttaaaaga | 37380 |
| attccattct ttggcattta gtgtgaagag agaaatattt gttatcgctg gaaatcatga | 37440 |
| ctcaatcccc ttgatcgttt aaaaaaatac accaaagata aagtttgtaa atggccatat | 37500 |
| ttatgattat gctactcaaa tatagaagaa ctttctgaag agtgccagta tacctttaa | 37560 |
| ttcccttaat aatgtcatgc tgactttcag aagccttatg atgtgtgaag gatctctcta | 37620 |
| gagttgaaca ctattggata acagtgttac ctaagttttt gaaatagaat cttaaaagga | 37680 |
| ttttaaatta tgggcatagt tattctaatt cttctcttgt aatgtatcat cctgcagttg | 37740 |
| aagctatgta catatctctt caaaaggtgt gtttttgcaa tacagttgct acaggggctg | 37800 |
| gtgccttaa atggcaacta aaaggttaat tgaatgtgaa taactcgtta aagggagagc | 37860 |
| tcagacattc cttctagcac acacacagaa aaatagaaat gaactaccat gtgacccaca | 37920 |
| gtccctgtat acgtctggtt tgtaacaaga gattctttat caagcaaaac agtatgtaat | 37980 |
| gacatttctc tggaaccttc cattacaagc caccttaatg cagtttggaa gatacctccc | 38040 |
| ccacctgggg gaatttccag ctaaagtata taaaagagtc cccaaatcat ttcccaataa | 38100 |
| aagtacactg tgcagtttct gaagagttta cactatttaa agcataatca tagcctcaca | 38160 |
| gcagtaacag tcctctggaa atatttgtcc ttggtgttta ctttgcattc cttcctctag | 38220 |
| ctgggtgtac gaccaagcca gggaggagag gcaccacgag aagtgacttc agactcagga | 38280 |
| agcatcgttg tgtccggctt gactccagga gtagaatacg tctacaccat ccaagtcctg | 38340 |
| agagatggac aggaaagaga tgcgccaatt gtaaacaaag tggtgacacg taagaagaat | 38400 |
| tttttccctt ttctattagt ttttaaaact gttctacttt tcgaaaaaag ctagtgtcaa | 38460 |
| tatcactttt tacttatgag aatggcacag gggagatatc ttatccttac ttatattatt | 38520 |
| aatgctattc ctgaatttgg agtagcaggt tcaattcatg ctttatattt tatggcatca | 38580 |
| gaaatgttct ttccatgtca agaatattta tgaactggca agatgaaaat aatttcaata | 38640 |
| gtattgcaaa atcattaatc ataaagaagt ctttgtcaga gaattactgc tgtccatcat | 38700 |
| atttcataa tgtaacctat attttatgg gagggaggga gggagggaag aagcatggaa | 38760 |
| gagagggagg tagggaagga ggaaagatta cacaggtcaa gagctttgtg tcagctttga | 38820 |
| cttttaaaat gttctttctg catagcattg tctccaccaa caaacttgca tctggaggca | 38880 |
| aaccctgaca ctggagtgct cacagtctcc tgggagagga gcaccacccc aggtaagttt | 38940 |
| gggatggatc agagggcaag tatacaccat accttcccaa gacaaagatt ttagaaactg | 39000 |
| tgtttctttc agagaaagaa gggattcaaa ttacaaatgc ttagctctcc ataaaaacta | 39060 |
| tagcagtaca tgatgtacat catggagcag cctgcaggat gctttaatgc acgttgactt | 39120 |
| caatcacagg aagcagaaca accttacact agtctagggg gacaagacag atcctcacac | 39180 |
| agctgtaggg ctgaagaaaa gcactgtgga aggtggcttt tgctgagtgc attaaaaatt | 39240 |
| gccaaacaaa tggttgaagt catattacgt aatttcccctt ttgtgagttg ttacagagcc | 39300 |
| taagtttatt attccctgaa gttttatgaa tgttttgtca tgggttgcac cacaaatatt | 39360 |
| taagggtgat gaaaggcaga aataccttca ttttacagaa taagaaaact gagacttaga | 39420 |
| aaaaattggc ctactcatag tcacacattt taaatgttac aaaactggga ttgtaactta | 39480 |
| agtttgtaga ctccttctca cacccaatgt cacatatttg gaatgtaatt ttttttttaat | 39540 |

```
tatattctat gcaaactgaa aattctgatt aagggtttc ctgaccattt ttagagcttt    39600
aaatgaagca tttgtctaaa ttccttgttc acatatattt gaaaattatt tataaaatgc   39660
taaaatgtat aaagatagtt gttaacaata ttcaaacagc atgacgtact atagcaataa   39720
caggaaattt tagatacccca ttacttttgc caaaaccaca tggaagtctc aacaaaccta  39780
tggagaaaaa tcttaaacaa aaataaaagt tccaattaat gttgattgca ttcttacctc   39840
atatacttgt taatttaagg gatatgttta ggttattatt tagctatttc taattttact   39900
gtaaaattct tgtgaaattt ttgtttaaaa aaaagtatta tatagttctt atctttgccg   39960
gggcacagag ctaaggctat catctctaaa tctgattaat gtatgcaaac acacagaatg   40020
aaactagctc agaatatctc ttttaatctc cctctgaagt agagtgattt tggtaaagtt   40080
ttcattatct gcggaaacat tgtttaagcc aaagctatac aatttccagc tgagttgctc   40140
tgaatttgaa actttaagtt gacaatcttc gtgcttgtta gcagcaggat cattaatatc   40200
tcgtctcaat ggcccagccc acacatatgg atgaccacta gcaagtgtaa tgatctcaat   40260
atttatttct cattcagttg ggtttccttg tatttgccac attagtgttt accctgttcc   40320
taatggcaaa atattctgtc atctccttgc cttttataaa gttaatata ctttctcatt    40380 ttaatctgtc cccacagatc tctagtcatc actgttttta tttgaatgtc tctcatccct   40440
ctcaactctt ttactgccca atttctgtga ttcctgaaga cttcaacaat caatactctc   40500 ttttttgtt tgttttgttt ttttttttg agacagagtc tcactctgtc acccaggctt    40560
ggagtgcagt ggcgccatct caactcactg caacctccgt ctcctgggct caagcgattc   40620
tcgtgcctca gcctccccaa gtagctggga ctacagacat gcgccaccaa gcccagctat   40680
tttttagatt tttagtagag acagggtttt accgtgttgg ccaggctggt ctcgaactcc   40740
caacctcagg tgatctgcct gcctcaacct cccaatcaat actcttcta gaataagtat    40800 cagcactttt gtttctcacc ttttctcctt tcttggttct cttcctataa atcccatagt   40860
ttcagacctt ttaaattagg agagctctct ggggaatgtg cttaaggtgg agagcgattc   40920
tatactaggc aggtagaaag gaatattcct cagctgtctt caaatgattc attaaggaaa   40980
agcagggtac agtgatagga ccatgagatt tggaaacaaa gaaagctttg gggaatcact   41040
cccctggttc aagatttcct ttaaagtgag gatcttggcg gaggttgaag tgagccaaga   41100
tcacaccgct gcactccagc ctgggtgata gagggagact gtctcaaaaa ataaaaataa   41160
aaaaataaag tgaggatctt agtactgcct gaaaggattg ttgcaagcat tgaataacag   41220
tgacagtgga gtcctcagta aatgccaagt cctgcattcc gccctgtgaa tccatcattg   41280
gagtctagtt aaatatgctc tggctcacag atcctctgtg caataacttc ccttttcttt   41340
tttctccaga cattactggt tatagaatta ccacaacccc tacaaacggc cagcagggaa   41400 attcttgga agaagtggtc catgctgatc agagctcctg cacttttgat aacctgagtc    41460
ccggcctgga gtacaatgtc agtgtttaca ctgtcaagga tgacaaggaa agtgtcccta   41520
tctctgatac catcatccca ggtaatagaa aaataagctg ctatcctgag agtgacactt   41580
ccaataagag tggggattag catcttaatc cccagatgct taagggtgtc aactatattt   41640
gggatttaat tccgatctcc cagctgcact ttccaaaacc aagaagtcaa agcagcgatt   41700
tggacaaatg cttgctgtta acactgcttt actgtctgtg cttcactggg atgctgtgtg   41760
ttgcagcgag tatgtaatgg agtggcagcc atggctttaa ctctgtattg tctgctcaca   41820
tggaagtatg actaaaacac tgtcacgtgt ctgtactcag tactgatagg ctcaaagtaa   41880
tatggtaaat gcatcccatc agtacatttc tgcccgattt tacaatccat atcaatttcc   41940
```

```
aacagctgcc tataaaatag ttttgtccct gtatgtgagc actgaaacag catttggttg    42000
acacatctag ttttttcatct tgcagtttca aatccttctt tttgaaaatt ggattttaaa    42060
aaaaagaagt aaaagtcaca ccttcagggt gttctttctt gtggcttgaa agacaacatt    42120
gcaaaggcct gtctaaggat aggcttgttt gtccattggg ttataacata atgaaagcat    42180
tggacagatc gtgtccccct ttggactctt cagtagaatg cttttactaa cgctaattac    42240
atgttttgat tatgaatgaa ctaaaatagt ggcaatggcc ttaaccttag gcctgtcttt    42300
cctcagcctg aatgtgcttt tgaatggcac atttcacacc atacattcat aatgcattag    42360
cgttatggcc atgatgttgt catgagtttt gtatgggaga aaaaaaatca atttatcacc    42420
catttattat tttttaacct tcttcatgca agcttatttt ctactaaaac agttttggaa    42480
ttattaaaag cattgctgat acttacttca gatattatgt ctaggctcta agaatggttt    42540
tgacatccta aacagccata tgattttttag gaatctgaac agttcaaatt gtacccttta    42600
aggatgtttt caaaatgtaa aaaatatata tatatatata ttccctaaaa gaatattcct    42660
gtttattctt ctagggaagc aaactgttca tgatgcttag gaagtctttt cagagaattt    42720
aaaacagatt gcatattacc atcattgctt taacattcca ccaattttac tactagtaac    42780
ctgatataca ctgctttatt ttttcctctt ttttttccctc tattttcctt ttgcctcccc    42840 ctcccttgc tttgtaactc aatagaggtg ccccaactca ctgacctaag ctttgttgat    42900
ataaccgatt caagcatcgg cctgaggtgg accccgctaa actcttccac cattattggg    42960
taccgcatca cagtagttgc ggcaggagaa ggtatcccta ttttttgaaga ttttgtggac    43020 tcctcagtag gatactacac agtcacaggg ctggagccgg gcattgacta tgatatcagc    43080
gttatcactc tcattaatgg cggcgagagt gcccctacta cactgacaca acaaacgggt    43140
gaattttgaa aacttctgcg tttgagacat agatggtgtt gcatgctgcc accagttact    43200
ccggttaaat atggatgttt catggggaa gtcagcaatt ggccaaagat tcagataggg    43260
tggattgggg ggataaggaa tcaaatgcat ctgctaaact gattggagaa aaacacatgc    43320
aagtattctt cagtacactc tcatttaaac cacaagtaga tataaagcta gagaaataca    43380
gatgtctgct ctgttaaata taaaatagca aatgttcatt caatttgaag acctagaatt    43440
tttcgtctta aataccaaac acgaatacca aattgcgtaa gtaccaatta attataagaa    43500
atatatcacc aaaatgtacc atcatgatct tccttctacc ctttgataaa ctctaccatg    43560
ctccttcttt gtagctaaaa acccatcaaa atttagggta gagtggatgg gcattgttt    43620 gaggtaggag aaaagtaaac ttgggagcat tctaggtttt gttgctgtca ctaggtaaag    43680
aaacacctct ttaaccacag tctggggaca agcatgcaac attttaaagg ttctctgctg    43740
tgcatgggaa aagaaacatg ctgagaacca atttgcatga acatgttcac ttgtaagtag    43800
aattcactga atgaactgt agctctagat atctcacatg gggggaagtt taggaccctc    43860
ttgtcttttt gtctgtgtgc atgtatttct ttgtaaagta ctgctatgtt tctctttgct    43920
gtgtggcaac ttaagcctct tcggcctggg ataaaataat ctgcagtggt attaataatg    43980
tacataaagt caacatattt gaaagtagat taaaattttt tttaaatata tcaatgatgg    44040
caaaaaggtt aaaggggggcc taacagtact gtgtgtagtg ttttatttt aacagtagta    44100 cactataact taaaatagac ttagattaga ctgtttgcat gattatgatt ctgtttccctt    44160 tatgcatgaa atattgattt tacctttcca gctacttcgt tagctttaat tttaaaatta    44220
cattaactga gtcttccttc ttgttcgaaa ccagctgttc ctcctcccac tgacctgcga    44280
ttcaccaaca ttggtccaga caccatgcgt gtcacctggg ctccaccccc atccattgat    44340
```

```
ttaaccaact tcctggtgcg ttactcacct gtgaaaaatg aggaagatgt tgcagagttg   44400
tcaatttctc cttcagacaa tgcagtggtc ttaacaagta agcagttgaa tgtatctgtt   44460
ccataaatat taacctagag catagcaaat gaattctaaa ttctcaagta ggaggagcta   44520
agagcaagag agctgcaacc aagctacaaa ctaaactctg aattcaatgc acagctccat   44580
taattttgaa agatgtaatg tttgttgcta tcttaatata cttttgatat ctacagcttt   44640
aaaaaaatca tagtggaaaa acacctgcag gaaagttcca tgacttcaaa caaattctgc   44700
ttctaaataa gcacgtaaaa ataagtgaat atcaagagaa attatatgac taaatctaaa   44760
tctttagaga aaaaaatgag aactgaaaat agtgtcacca tatgtgcttt attctcattt   44820
ttataaaaaa agtgtcagca gttgattgat ttaggatttg aatacttaga aaagtgactg   44880
attgtttggt ctagattaga atgttgttgt gaagagagtc agaagtttaa tttgtacttc   44940
aaaaagaatc tgttagaagg atttctcaga agactgagag cttagaaaaa aaactgacat   45000
taaataaata acaacaattt atggaaattg tctctttcta gtcccaacca ttatagaata   45060
gacatctttt gttaaagaat aaaacagtag gctgcaagat ggtgctgtgt ttcacataaa   45120
cagtgctttt tattattttc actgtaatag tcaaatatat aacaacagca aaagattcta   45180
cataagggaa aaatagctta catttaggta cattaccaag tattagtctg aaaacatcta   45240
cctttcaaac ataatttaga taatgaaaca caaagaagag cagctcagcg tgaccataat   45300 cttggttttct tactttgtgg ctgagggcaa gaatatcttt atattggcat atccaccacc   45360
ccagggctgt tgcttctgtt ctagagcacc ctggaatcac taattacagc atcacccagt   45420
atacaagccc ctgcatcaca atgtctgtcc cttagccgta gacctgtcac atgctaatca   45480
tgtgttctaa gaccttatta taatcctaat gctacagatg acctcagggt agcccctctc   45540
cctcctagca aagtcattat tatcctcttt taaagatgaa gcaaaccagt gcagtggctc   45600
tcgcctgtat aatcccagca ctttgggagg ctgaggtggg ccaattgctt gagcccagga   45660
gttcgagacc agcctgggca acacagtgag accaagtctc tacaaaaaat acaaaaatta   45720
gccgggcatg gtggtgcaca cctgtggtct cagctatgta ggaagttgag gtaggaggat   45780
cacctgagcc tggggaggtt gaggctgcag caagccatga tcgtgccact gcactccagc   45840
ctgggtgaca gagtgagacc ctgtctcaaa aaataaaca aacaaataaa catgaagccg   45900
tcgaggtccc cagcagttaa gtaaattgcc actggccagc tagtatggtg gaaatggaat   45960
ccaggcatct ggtcctccat tctggcactt ttccaaactt ttgtaggggg ctttatagaa   46020
acgctgaagg gcaaatggtg tgcaggggaa tgagggttta gtgagtagga gttccaaatt   46080
tagaaacctc actctctgta tcttttagat atacaaatat ttaccatata ttacagttgc   46140
ctctagtgtt cagtacagta acatgctgca caggctcata gcctaggagc aataggctag   46200
accacatagc ttatagctta ggtgtgtcaa aggctctacc atctaggttt tttgttttgt   46260
tttgttttgt tttgtttttg agacggagtc tccctctgtt gcccaggatg gagtgcagtg   46320
gcacgatctg ggctcactgc aacctccacc accaaggctc aagtgattct cctgcctcag   46380
cctcccgagt agctgggatt acaggcgtga gccaccacgc ccagctaatt ttttgtatt   46440 tttagtagac gagggttttc accatgttgg ccaggctggt ttcaaactcc tgacctcaag   46500
tgatccaccc tcctcggcct cccaaagtgc tgggattaca gcccatcta ggtttgtgta   46560 ggtacactct atgatgctta cacaataaaa tcaccaaatc acacacttat caaaatgtat   46620
ctccaccatt aagctatgcc tgactgtgta tcaaaatgga agaagaagct gggcacagtg   46680
gctcacgcct gtaatcccag cactttgaga ggccaaggcg ggtggatcac aaggtcagga   46740
```

```
tttccagtcc aagcctggtt aacacggtga agccccgtct ctattaaaaa tacaaaaatt   46800
agccaggcat ggtggcaggc acctgtaatc ccagctactc aggagtctga ggcaggagaa   46860
tcacttgaac ccaggaggca gaggtttcag tgagccaaga tcacaccact gcactccggc   46920
ctgggcaaca gagtaaaacc tcgtcaaaaa gaaaaaataa taaaaataaa aaaaaatgga   46980
acaagatact cagggatgta tatttaattt tttaaaaaat attctgctct cattttaata   47040
tggcagaacc gattgctttc taagtgtggc ttttttccag taaaggttaa ttattaagac   47100
cactagtcct ggcctgggtc aatcccagta tgatcctggg caagtaaatt aaagaagata   47160
acttctctgt gcctcagttt ttttttgttt tgtttttttgt ttttcatttt acaaaatgga   47220
gataattgta gtaaatcaaa ttttttagagg tgataggttt gttcatttct tgaatgcggt   47280
gatggtctcc caagtcacac atatgtaaaa acccatcact ttaaagatat gcagtacgtt   47340
gtatgacaag aaattgcttt taaaaggagc aaactacctt ccaggggttgt tgtgaggcat   47400 aaatggcaat ccacagcacc acagcaagga ttatcatgtg ccctccagag acatactctc   47460
aggtggatgc gagaaatatc cagctgttgc agcaacttca tcccactcga aatccagctg   47520
agtcacactc acaggtggaa tggagggctt cgagaggcca tggggcaagg tgacccttcc   47580
ttatcatcta attacagacc ttctcaaggt ctgttcactg aacacttcgc tgtagtgttc   47640
acttaggtgt aagtaggcta taggactgga catttggata tttcatcagt tcaaatagtc   47700
ctgggcgtgc tttagtttct catgcttttg agcagagttt taaaataagc cccatttgcc   47760
cctacagatc tcctgcctgg tacagaatat gtagtgagtg tctccagtgt ctacgaacaa   47820
catgagagca cacctcttag aggaagacag aaaacaggtg agtggtgttg gcagtatgac   47880
tatccagtag ctttttgccta tcaattctgt ataacaaatg aaatgctact tctaaaaata   47940
catctccatt ttttgttgtc atggtgtgtg tacctttgtc atcacagtat gatttatcg   48000 ctggtctcaa aaactaaaag ataccttact caacaatcac ctagactttc agtcactaac   48060
aaattaagaa atttgttgtc tgtccttta aaaaacattt tctaagaaga tctttgttat   48120
ttagatttag cagacattcc ttttcattag gcagctctgt ctaatggctg acccaacact   48180
cattgtcatc tatttgtctt cctttactaa gccagcaagt ttacatttc ttttttactta   48240 ataaaatatg catttactag aaggaagttg aattgaatct cataaatatt acatacttaa   48300
atatgaatgc ttttaatttt ttctttcaaa aggtacactt tagtgtattc attaatttat   48360
ttatagtcca cttgcttcca aaaggactt atgatatctt agtttggttt cttattgaaa   48420
agaactagta aatgctgtaa ctgaaacaga aatttgctgg aagtcccaga gactaagtga   48480
tttgaatttg caacaaactc tgaatttttg tgcatttttg aaaaatgcat ttttcaaaac   48540
tgtcaattca cgaggaatta tcagcattgt aatttgtctg ggataatgtc tttagtttca   48600
gaaagttttg tgtttggcat cattaccact ctgttgacat ataaatttcc tcttgagctt   48660
aggaggcttc tctgagagtc aaacatttac tttgagagtg ggcagatctt gctttacttg   48720
gaaggataca cttacaggat agaaacacag aatacttgaa cactgaagaa tttgaaaatg   48780
tcaattctca gaagatcttg aacacttatc tccaaatgtg acacagaaac ttactgtaat   48840
aacccctaaa atctgcttga attacttagc acaagaaaaa atgaatgct tgagctggct   48900

attttgaatt gagtcaattt aagatttaa aattcatatt tagcttagaa tcagtacatc   48960

ttactctttg gttatggca aatcatggta ttgatgagac aggaacgaaa tgttggatgt   49020
acgttaattt cccctacacc ttcctcactt cctaaactgg tggtgtcttt tctttttttt   49080

ttctcttcct cccccgggtg ggaaaaacag gtcttgattc cccaactggc attgactttt   49140
```

```
ctgatattac tgccaactct tttactgtgc actggattgc tcctcgagcc accatcactg   49200
gctacaggat ccgccatcat cccgagcact tcagtgggag acctcgagaa gatcgggtgc   49260
cccactctcg gaattccatc accctcacca acctcactcc aggcacagag tatgtggtca   49320
gcatcgttgc tcttaatggc agagaggaaa gtcccttatt gattggccaa caatcaacag   49380 gtaactttc ttgtctgcaa agaaactcag aagactttcc tacccagttg gtagattctg   49440
taaagtagct tgctgttgtc tgtcatcagc tctcaaaaaa aaaaaaaaaa aaaaaaaaa   49500 tagatcattg tcatggtaca tggagaggga agtgagaaaa tgtggagaaa catcttcctt   49560
agaatatggt aaagaagccc gggcgtggtg gcagtaaaga agataatttt tttcctctca   49620
agaaatttct cacctgattt gggtatttat gcatttctaa taacacaagt tttgttgaaa   49680
atgtagaaaa ttggccggac ggggtggctc acgtcagtaa tctcagcact ttgggaggcc   49740
gaaatgggca gatcacttga ggtcagaagt tcaagaccag cctggccaac atagtgaaac   49800
cccatctcta ctaaatatac aaaaattagc aaggtgtggt ggcatgcacc tgtaatccca   49860
gctactgggg aggctgaggc aggagaatct tgaacctgg gaggcgaagg ttgcagtgag   49920
ctgagatcag gccattgcac tccaacctgg gtgacagagc aagaccctgt ctcaaaaaaa   49980
aaaaaaaaaa aagggccagg cgcaatggct cacgcttgta atcccagcac tttgggaggc   50040
caaggcgggt ggatcacgag gtcaagagat cgagaccatc ctggccaaca tgatgaaacc   50100
tcgtctctac taaaaataca aaaattagct gggcgtggtg gcatgcacct gtagtcccag   50160
ctactcagga ggctgaggca ggagaattgc ttgaacccag gaggcggagg ttgcagtaag   50220
ccaagattgt gtcactgcac tccagcctgg tgacagaggg agactctgtc tcaaaaaaaa   50280
aaaaaaaaaa ggtggaaaac tgaacactgt ttcaaagtac ctttaaaaat ataatttag   50340 ggtaatagtg tcattgttct tagcagatag aggctgaagt acttacggga acagtagcat   50400
catgttatct gtattttagt ctcaagtcgt caagccagag acaaatacct aagggaaggg   50460
tatataggtg ttcattgtat acttttttt tttttttt tcttcctgaa atggagtctt   50520
gctctgtcgc ccaggctgga gtgcaatggt gggatcttgg ctcactgcaa cctctgcctc   50580
ccaggctcga gcaattctct tgcctcagcc tcccaagtag ctgggactac aggtgcccgc   50640
caccacgccc ggctaatttt tgtattttta gtagagatgg gattttacca tgttggccag   50700
gctggttttg aactcctgac ctcaaatgat ccacccgcct cggcctccca aagtgctggg   50760
attacaggcg tgagccacca cgcccggcct tgtatcactt ttttttttt tttttttt   50820 aacttttctg tagttttgaa attttccaa ataaaatgtt gagggaaaaa aactcttccc   50880
caaatttgaa ataatcattt tatcacaatt tgaatgggct ctgtaacccc ttatcttgaa   50940
ttcgtcataa tataaaattc tgctaattac acgtagtatt tacatgattg tatggaagaa   51000
tcattaagac aattatctgg aaaatgaaca aacagtaaat ctgaatattg tttgaaaatt   51060
acggatgtga aaagtttccc ttttttttct agtttctgat gttccgaggg acctggaagt   51120
tgttgctgcg accccacca gcctactgat cagctgggat gctcctgctg tcacagtgag   51180
atattacagg atcacttacg gagagacagg tacagcagta aaatgctatt ttacactctg   51240
attaaatcag attctgttgt ggataacctg aaagcccaac agtgaacaaa gaattaaaga   51300
aactttggca agtccattca acggagccct tgttttttcc aagaaaatac gtaagatata   51360
gatgatataa tttgttctaa aacccaaata aaaagttgtt tatatactac aactagaggg   51420
ggaacggcag agctgaggaa ataaaaggat tgtaaattca caaacatatt atcagtggtg   51480
gaaataagtg atttttattt tttcttctct ttactttct gtattttcca aatttttattt   51540
```

```
aaaaggaatg tattctgtta aaagttttaa aaaggacaca atgcatgcaa tcctgggttg   51600
agggcttacc ttctcccact tctaatgcta ctctactact cagtgacatt ttaaagctga   51660
aatgttaaaa cagcgctaac tgtaattttc tctcaatgtt tatacactta ccaaggtttg   51720
ctacatgcat aaatacccct ttctgttcaa gatagcgctc tttaaaaggg aataagcaag   51780
aagatgtgat ttacatgctg ctataaatgt ggtaattcaa ttaatcagta atacccaagt   51840
agctctaaac ccctcacact ctgaactaac ccttttttcat acaggaggaa atagccctgt   51900
ccaggagttc actgtgcctg ggagcaagtc tacagctacc atcagcggcc ttaaacctgg   51960
agttgattat accatcactg tgtatgctgt cactggccgt ggagacagcc ccgcaagcag   52020
caagccaatt tccattaatt accgaacagg tacaaacttc tactctgggg tgacaccagc   52080
ttttacttat tcagatactg ttttgcaatg ttctcccaag gtattttttct aattgtagaa   52140 tagattttcc ttttaatga gcaacaacct gcagctagca cctgcagcga acagagtttt   52200
gagccagata aagaaggaag caccccaagg gcaggaagtt cagtcagttt tgtcgatata   52260
ttccgcatgt ctgcaatacg acaggcatag agagtgttca gtaagtattt gtgggaaaag   52320
aatggatgag ttgataaagt aggaagagac acctgcttgt ggaatgtagc ttctttgtga   52380
atgaagcaac catctcaaaa ataggaaatg gtattgagat gcctgcccca tccctctaaa   52440
agctctctct gtattctttc gagaagaaat acctttctca tgtaagcgat cattcgaata   52500
tgtaccagac ctagagagga ggacttgtcc aatcttgtct ccaaggactg gggcttcact   52560
ggtttctccc tgcttttatt tgtagaaatt gacaaaccat cccagatgca agtgaccgat   52620
gttcaggaca acagcattag tgtcaagtgg ctgccttcaa gttccctgt tactggttac    52680 agagtaacca ccactcccaa aaatggacca ggaccaacaa aaactaaaac tgcaggtcca   52740
ggtaagaatc atctgcatct cggccaggtg cggtggctca ctcctataat cccagaactt   52800
tgggaggctg atgcgggcag atcacttgag gttaggagtt cgagaccagc ctggccaata   52860
tggcgaaacc ccgtctgtac taaaaaatac aaaaaaatta gctgggcatg gtggcttgtg   52920
cctgtaatcc cagctactca ggaggctgag gcaggagaat ggcttgaagt ctggaggcag   52980
aggttgcagt gagccaagat agccccactg cactccagcc tgggtgacag agtgagagac   53040
tccatctcag ggaaaaaaaa aaaaaaagag taatctgcat ctcatataca acaggataga   53100
tggggtagga ccacctaata ttcttttttta tataaatggc taccttgttg tgagtactat   53160
gtattttttt gtcctatgtc atcattgtcc ccattcatga gttcagggct caagatcatt   53220
atcaacccct ttcacagtag aagtcttaag tgcatttctg tttttacatg gatagttcta   53280
tttagtgata tggacatctt aaattactag attcacccctt ctggttttgt ttatcattca   53340
cactaagaag agataaatgg cctaactgac tttttcagct cttttttagct atgttgtctt   53400 tgttttttaaa tagaatactt gtgaaattag gatcttaagg caatttatta gagtcaagtt   53460
aattttcatt ttttctgaga gcagtatcac taattgttgg gggcatcata ttaagtttta   53520
gatcttatcc ttgagtgtga cttcactccc atatggtaat ttgtattagc aatgaacagg   53580
tttgtccaag aggaaatcaa agtctgactc tccatatttt tgttacaatt ctgcaaataa   53640
aaattctagg ccaccatatg tttactacca aactctagac gccacttgag gactttatag   53700
tggatgacgt ggatgttgca tttgcttttc actccctttg cagatcaaac agaaatgact   53760
attgaaggct tgcagcccac agtggagtat gtggttagtg tctatgctca gaatccaagc   53820
ggagagagtc agcctctggt tcagactgca gtaaccagta cgtaaccact gcttggtttc   53880
cattttcaaa gtcaaatttt gttcttgggt gtctgaatgc ccacgacatg tcttttgcaa   53940
```

```
ttacacatag ggaaagtgaa cttgttggtt agtttatgtc ttgagctgag ccctttacga   54000 acatctttt  tccttctcag tgccaagcga ggaatttaca gagaaagaag ttgtgaaacc   54060
accatagtta gttgctgtgc tttgaatttc ttttgctcaa atggcctcag cgaaatctta   54120
tttgcctata gcaaatctac aaaaaatttt cctagaccgt cttttctaca actggatggt   54180
aaagttgatt gaagtgtgcc tcatgtagct ttatgtttgg ggcatttgaa gggctatggc   54240
tggaccagag tgtaatataa atgcttaata gagagggggaa aagaagagtg taagaaccat  54300
tatagggctg ggctcacgcc tgtaatccca gcattttggg aggctgaggc aggcggatca   54360
cgaggtcagg agttcgagac cagcctgacc aacatggtga accccatct  ctactaaaaa   54420 tacaaaaatt agccagtcgc ggtggcacgt gcctgtaatc ccagctactc aggaggctga   54480
ggcagaagaa tcacttggac ccaggaggca gaagttgcag tgagccaaga tcatgcctct   54540 gcacccagc  ctaggtgata gagtgagact ccatctcaaa aaaaaacaaa acaaaacaat   54600
tataacaatt tgaatctgac attgcaaatc agctttacca cttccaaggt atagaaaatc   54660
caggtctatg agactaacat cacattgtaa aaatcaaatc gtggtagaat atctttaaat   54720
taatataaat acatccccat tgtggggaca ttttgcaggg tatctgctta tctcacatac   54780
acctatgttt taataagtga tgcaacattg catattttct aaaccaagaa aaattaagca   54840
agtgtttaag tgattttttcc ttttgatagt gggttaattg gacttcatca aagaaaatgg   54900
tatctgcaaa actgctttgc atgttataaa aatgcttatt tcacaacttg cttttcacat   54960
aacctcttac cattaatttg cctaacagac attgatcgcc ctaaaggact ggcattcact   55020
gatgtggatg tcgattccat caaaattgct tgggaaagcc cacagggca  agtttccagg   55080 tacagggtga cctactcgag ccctgaggat ggaatccatg agctattccc tgcacctgat   55140
ggtgaagaag acactgcaga gctgcaaggc ctcagaccgg gttctgagta cacagtcagt   55200
gtggttgcct tgcacgatga tatggagagc cagcccctga ttggaaccca gtccacaggt   55260
atatggttaa ttgcaccacc aggtgcccat gggagcagcg gctttatgcc ctactgaatg   55320
aattatgctt cactgggcta ttgattcccg tgtaagggtg aaaagaatt  attaggaaag   55380 atcctcttta aagaggaatg gtaagaaaca ataaaactta ggtgatattt aaggaaacaa   55440
gtctgattaa aagaaatttt ggagtatcct ggcttataca caagaccata agcaagaca   55500 tttgaagagg atactaaagt tgtggattat ttcctaagct ctgactccct gtgattaccc   55560
tcactatgta taaagaaaag aagtttggca ttacagagct tacttataaa aaggaaccca   55620
aactcgggca tttcatagca gcatgattct gagcacacgt gggtaagacc tttcttctct   55680
ggttagatat catatgctgg tgtataatta gcttaaatga ttgtgattta gacacctagg   55740
aaataatcaa tagggcaatt gctttccata atactttatc ttcttgtgct ttatttctga   55800
agcagagtag aatgctaaag atgtatccta gtgacagcat aaaccctaga ggtgacagtc   55860
tgtattattg cttttcgctt ctcttttctg cttctgttgg gagccagttt tcttcttacg   55920
ccgcattaca gagagaacgt caaatttagc agccatatct gccataggt  ccaaataaag   55980 agacaataaa aacattattc tctcttttt  ggatggaata ctgcgtgaaa tggttatcca   56040
tacaaagata ctttatgtag aatagaaaaa ggaggccggg tgcagtggct cacacatgta   56100
atcctagtgc tttgggaggc taagccggga gcactgattg aggccaggag ttcatgatca   56160
gcctgggcaa tgaagtgaga ccccgtctct acaaaaaaat atgaaaaaat tagcgaggtg   56220
tggtgacaca tgcctgtagt cccagctact caagaggctg aggtagagga tcacttgagc   56280
ctacgagttc aaggctgcag tgagctatga taactccact gcactgccgc ctggatgaca   56340
```

```
cagagagacc gtttctaaat taattaatta acaattttaa gaaagaaaaa gggccattgc    56400 ttattttttcc atacaaaagt aaaataaatc ataatggcca ataagccaat gtaactttt     56460 tttttaaggg aaagcaaaac ttgtaaaacc taaaatctct tagagttttg gcatttaccc    56520
aaatgttttc agtgattctg agaattggtg gatataaaac acatttctca gcaaacactt    56580
tcttcatttt gcatcccta ctgtacgtac tttcttgtac tgaatctttg cttgaccagg     56640
gaacccacct agcccaacaa gaacaatcca ttctacttct tggaactcac tttattttcc    56700
ttttccccca tttcctataa gataacctct aaccaatgac aatctcgaca gctattcctg    56760
caccaactga cctgaagttc actcaggtca cacccacaag cctgagcgcc cagtggacac    56820
cacccaatgt tcagctcact ggatatcgag tgcgggtgac ccccaaggag aagaccggac    56880
caatgaaaga aatcaaccct ctcctgaca gctcatccgt ggttgtatca ggacttatgg     56940
taagacatga ccgttgttca ttggaataaa gatggagatc atctctaaca cagtttctaa    57000
ggtggtgaaa atataatatc ataataaatc taactgttct tttcctctgc atcaaataat    57060
cttattgtaa ttttatatca acggaattcc tttatgttga cctaagtttt ccagatgact    57120
attgggacag aattttataa atagcttgg attttgtgca gctctttag atgtattgtg      57180 cttattttaa aaggttgtgg ggggcaattt acatatccat tggttgaatg cataaatcga    57240
cttagttatg cattttctga gctctgttac cttggtaaag aatattttac agttgtacc    57300 agtctacctt gagcctaccc tcattaaaac attttaaaat ccttccagac atacatgcag    57360
aaaactgcta ggaacctagg ggactgatgt acctcttaac ataaggccaa tttcagggga    57420
aactacagaa agagggttca gagacaaat gaacattct ctttgcctct ctatgataag     57480 gaaaaatta tgatttacac ctgtcagatc ataaaaaga aaaatacgct aatacccact      57540
tttctcattt tttttaccag cttagtttaa gtatataatc tatggcttac ttaagcttaa    57600
ccgctaagag catttaaaaa ttgataaata catttatcac ctgcactgta ggaatgaaat    57660
taatctagga atttcaagg ttgtgggttt tgctggtttg tttatttttt attttctaac     57720
cattgcattt acctaatgct gtagtgaaac tccttgggtt tcagttgagg acgttgctaa    57780
agctcaccat gcccttatt ctctaggtgg ccaccaaata tgaagtgagt gtctatgctc     57840
ttaaggacac tttgacaagc agaccagctc agggagttgt caccactctg gagagtaagt    57900
aacaaaatgt cttcatatgg acaaaccttc tgtatagaca aaaattaaag aatggtaaat    57960 cagtgggtt cagtggctca tgtctaaaat ccaagcactt tgggaagctg aggcgggagc     58020
gtcacttgag gccaggagtt tgagacctac ccgggcaaat agcaaggccc tgtctcttaa    58080
aaaaaataaa ataaataaaa taaataattt tttagattta tatgttaaca gtggaatgag    58140
tcctaatttg aaaatcaatt tgattgcctt tttgacgcat gactgtcatc ttttatactc    58200
cttcagaaag gggtctactg acccataaaa tggaatcact tcataagctt ataatgttga    58260
tattatggac tatgactgac atctagttta tgctctactt gttagaattt gttttcatag    58320
agctaagctt ggggagaccc cactggcttc tgctatatct taacaatgca tattaggcca    58380
ttcttgcatt actataaaga aataccggag actgggtaat ttctaaagaa aagaggctta    58440
attggcccac aggccagcag gctttacagg aagcatggtg ctggtatctt cttggcttct    58500
agggaggcct tgggaagctt actcatggtg gaaggccaag gggagcagg cacatcacat     58560 ggctgtggca aaagcaagac cgagagagag agagagttgg ggggggagga ccttatacat    58620
ttaaatgacc cagtctcttg agaactcact gtcataaaga gggcaccaag ccacaaggga    58680
tctgccccca tgatccaaac acctctcacc aggccccacc tccagcattg gagattacaa    58740
```

```
ctcaacagag atttggacag ggacaaatat ccaaattata tcacagcaca gtaaccattg   58800
gaccaaatca ggcttagatt ctagtcttct gttatatcaa taccttgatg tatgccttt    58860 caaaagtcag gtaaagtgtc aaagttttat catttataaa agagggatgg cattgtacct   58920
gttgagagaa aatacaaaat acttgccgta atattagaca cacacacaca cacacacaca   58980
cacacactct ctctctctct cacacacaca tacacacaca cacacacaaa attgttagct   59040
ggccatgtta ttgtaactcc taccacacat attttacat tataatacat taataatttt    59100
aatatttatt gaagtatttg tagatactat aaagccagcc ctgggaacca ctggtagtat   59160
ctataaagct tttcagctct tcaaaataaa atgtctgaga ggtagatatt ttcctatttt   59220
ctaattacag ttgaccttc tctctgaatg ccaaaggaga taatctacac attactagtt    59280
atatatttct tgaaatggat gaatttgata tataccaagg aaacgtttta aaataccaaa   59340
actttacatg gatgagccaa gcaggcacta atctctagct atgctcctgt gcagatgtca   59400
gcccaccaag aagggctcgt gtgacagatg ctactgagac caccatcacc attagctgga   59460
gaaccaagac tgagacgatc actggcttcc aagttgatgc cgttccagcc aatggccaga   59520
ctccaatcca gagaaccatc aagccagatg tcagaagcta caccatcaca ggtcagggaa   59580
ctcattgcac taaccacatt tgttaacaaa tacccacaat gtaaacgggc ttattaactg   59640
ttctacgact gacactgata aaattttattt tcagtgttat catcataacc cagttttaga   59700
acgttatttt catgctatga tcagaaatag ttttgtcctt tgaatgcctg attttgtgta   59760
atatttgtca tggaaattgc gtaagtgtca atcaacaagt ttgatcttcc atcattgtgc   59820
cctttcttat ttaaaaaatt gtaacataag gtttaaaact aaaagaaata aaaaacagtg   59880
atgtatagat cttagcatta aaaagcatag ttaatataaa agtaaacaat accacttaat   59940
aaaggccaaa attgtaaccg aagaatattc aatatctgag gtcttttta gcttttaaa     60000 attgtgattc caaggctcaa ctattgacca tctgattacg gtaaagagaa aacctcaata   60060
agtggctgac ccccattctg caagagggcc tcttccaaca tagcattttt gcattccaga   60120
atttacttta ccagtgtcct tgtctgtatc agtgattcac tttcgagata tgtttcttgt   60180
taacagttaa catccatagc atgctctact ttactgttca aatgtggacc actttggtag   60240
tctatataaa tatgggatga tagaagaacc cagaaaaatt gcaggctagc ttgagaattc   60300
tcctagtaaa aagcaagaac tgttaaaaat catctcttct caaatcccag gtttacaacc   60360
aggcactgac tacaagatct acctgtacac cttgaatgac aatgctcgga gctcccctgt   60420
ggtcatcgac gcctccactg gtaactatac cttctactga ggaaatgcca ttgacttgta   60480
tgcaatcagt ttcatgaact caaaaaacaa atgtgaggcg tatatttttg tattatagat   60540
tccagagaat cttgtttccg gtttacagta ttctcagatt cttttaagtg tgtttagaac   60600
ggctcgggag aaaagtgtgg gagtaatttt cttggttatt tgccttctta gagacttaat   60660
tttgttttct ttcagccatt gatgcaccat ccaacctgcg tttcctggcc accacaccca   60720
attccttgct ggtatcatgg cagccgccac gtgccaggat taccggctac atcatcaagt   60780
atgagaagcc tgggtctcct cccagagaag tggtccctcg gccccgccct ggtgtcacag   60840
aggctactat tactggtatt gctgcttcca tgctgtcatt ttccttctta ctacctagga   60900
cacatgaagt ccttagcaaa ctcccacagc gtctttgata ctgtgtcatg agaatgcgaa   60960
actctgttcc tgataacctc aaaaagcatt ctctgtgtag gagtggtaga gcctaataca   61020
tcccaaaagg catgagtgaa ggaaaatgca atttcaagac tgtactaatg gcatgactag   61080
actcatgttt tcctttcgct gcaagtttgc cagatacctg tcaattcagt cctggagaaa   61140
```

```
gatattttc  aaagcatact  agctgattgt  gattctgtca  ttacactcag  ctctctatag   61200
atatggcaat  cttgcaggac  ttgccagtgc  accacctgcc  attgaccttg  ttgaccacta   61260
tcacaggata  ggtcttgagg  cagagcagtc  ccaaccaccc  acattggaag  aatgcctgga   61320
atggggaata  agagttgtct  accttggtgg  gaaagactat  aagcctctag  tattattttt   61380
gcccaagaga  tgaaatattt  aaactatctg  tattagtctg  ttttcatact  gctataaaga   61440
ggtttaattg  actcacagtt  ccgcatggct  ggggaggcct  cagaaaatgt  acaatcatgg   61500
tggaaggaaa  agcaggcatg  tcttacatgg  cagcaggaga  gagaagcaca  caggaggaac   61560
ttccagatac  ttacaaaact  atcagatctt  gtgagaactc  actatcatga  aacagcctg    61620 ggggaaccac  cccatgatcc  aatcacctcc  tctcctcaat  acatggggat  tacaattcca   61680
gatgagattt  ggatgcagac  acagagccaa  accatatcag  tctgtataga  gtatcacctg   61740
gactttaaaa  ttcccacaga  acatacagac  attagaagga  gacactggct  ttttagaatt   61800 gggggaaca   ggaaaataga  agcagacatg  agaggaattg  aactagacac  ttcccacaga   61860
ggctgcacaa  acactggcca  atctctccta  cccttcactt  gcctttagtt  tcactttca    61920 ttgatctgcc  actgaggact  gcttggttat  taggcctaag  tagattcatg  tatataatct   61980
gcaggactct  ctttcaaatt  tatattccag  tggtggtata  tgatgctgat  agattttctt   62040
aaattcaaaa  aggcaaataa  gaccacgtta  aagaatacc   ctggaaaggc  caggcgcggt   62100
ggctcacgcc  tgtaatccca  gcactttggg  aggccgaggc  aggcagatca  caaggtcagg   62160
agatcgagac  catcctggct  aacacggtga  aaccccatct  ctactaaaaa  tacaaaaaca   62220
aaattagcca  ggcgtggtga  tgggtgcctg  tagtcccagc  tactcgggtg  gctgaggcag   62280
gagaatggct  gaacctggga  agcggagctt  gcagtgagcc  gagatagcac  cactgcactc   62340
cagcctgggt  gacagagcca  gactccatct  caaaaaaaaa  aaaaaaaaa   aaaaaagaa    62400 taccctggaa  aagttagcca  aaaaatgtct  attcaggcgt  cagatatgat  agtaagataa   62460
ttagtttgcg  atgcggactt  tatatgcagg  atatttgggt  gtttatggag  gaaaagtgaa   62520
gtcgatttta  ccttcaagag  gccaacagcc  agctggagag  gaagtgcctg  ctcccagtag   62580
cgtctgctgg  tgagaccgac  ttccacttga  ctagctgagc  ccattgacat  aatgtgatgg   62640
ttctattctc  ccttcaggcc  tggaaccggg  aaccgaatat  acaatttatg  tcattgccct   62700
gaagaataat  cagaagagcg  agcccctgat  tggaaggaaa  aagacaggta  agagtatctt   62760
gcaggtaaca  aggagaaaga  taggacaaaa  ctaataacaa  atgagcaatc  ttgcaatatg   62820
aaaaggttct  ccatgttttg  atgcatttct  tgtgattttt  tttatctaac  agcatagtgt   62880
atatattgta  ttctttaata  ggagaaataa  tttaacatgc  actgcagagt  ttggttttat   62940
tttttttctt  tactacagcc  actcaatata  aagccttgtt  attcacctt   taaaaattca   63000 aacaagatgt  taaatgtaa   aagaagagct  atcattgctc  ttcttttata  ccttctgttg   63060
aattttaaaa  tgtttccttt  tttaaaggag  ggagagaaac  ctctcacatt  tatctttatt   63120
tggtttctac  aacttagagc  taaataatgt  cttactttg   catccagttt  cagttaattt   63180
caagaaaatg  tgtattcctg  atataggaaa  atttcaaaaa  tgaacatgtg  tgttttatct   63240
atttttacca  tttcaaacca  tgaaaaactg  ttgagccaaa  cctctgtaat  tctcatactt   63300
atgacactga  tatgattagt  ctggattcta  cttcctacaa  cttgcttctc  aaatttaaaa   63360
aagaaagaga  gaaagagaaa  gactgcacat  ttcagttcca  ttaggtctaa  tttgagcaga   63420
ggcagcttct  acgggctca   gcggtttaaa  gctgtgtgta  tgataaattc  atactaacac   63480
tttttttctt  taaactata   aagaaaccttt  tgagaaaaat  cctaaagatt  tctttctgga   63540
```

```
aaaagtgttt tgtgatctca gaactgctca ttttctggtg gcttttatca aattgatgaa   63600
cagtcattgt tgcctgaatc gattattatc attgctgcta cttcctggag cttaatgcgc   63660 tttgctttt  tggctctaac ctctctcggc tagacgagct tccccaactg gtaacccttc   63720 cacacccaa  tcttcatgga ccagagatct tggatgttcc ttccacagtt caaaagaccc   63780
ctttcgtcac ccaccctggg tatgacactg gaaatggtat tcagcttcct ggcacttctg   63840
gtcagcaacc cagtgttggg caacaaatga tctttgagga catggttttt aggcggacca   63900
caccgcccac aacggccacc cccataaggc ataggccaag accatacccg ccgaatgtag   63960
gtgaggaaat ccaaattggt cacatcccca gggaagatgt agactatcac ctgtaccac   64020 acggtccggg actcaatcca aatgcctcta caggacaaga agctctctct cagacaacca   64080
tctcatgggc cccattccag gacacttctg agtacatcat ttcatgtcat cctgttggca   64140
ctgatgaaga acccttacag gtaattaatt gttctcttca cttctcatgg ggcagcacag   64200
aaaggaataa gttaggtaac tgaagtgacc agccctcgaa taaaagtgg  cttcatggcc   64260 gggtgtgatg gctcacgcct gtaatcccag cactttggga ggccgaggca ggtggatcat   64320
ttgaggttag gagttcaaga ccagcctggc caacatggtg aaaccctgtc tcttgaaaaa   64380 aaaaaaaaa  aaaagtggc  tccactttta gaacctctta gaagatggca catttaagcc   64440 ctgcttttt  tttttttaa atcccaatat ggctctactt tggaggacat accagagagt   64500
cactagcttt tatttcatag agaaaatgaa actatttctc ttattctcac acatttgagg   64560
ttcctttttg agtaagatag atgattctag aaaagaaaga tattctacct gaatttccat   64620
ttgtgtgcag aagtctaaaa cactaccttt acgatttgtc cttgaagaac cccactatct   64680
acaacatatc taaagaaaaa aaaaaacagg cgaagctgtg catagcagct gataagtgat   64740
tgattctcta aaacgtatat tatttaattt gtgttgacag tatccattt  ttttttttccc  64800 cgagatggag tcttgctcta tggccctggc tggagtgcag tggcgtgatc tcggctcact   64860
gcaacctctg cctcccaggt tcaagcaatt ctcctgcctc agcctcccaa atagctggga   64920
ttacaggcat gtgccaccgc acccagctaa ttttttgtatt tttagtagag acggggtttc   64980
acgatgttgg ccaggatggt ctcgatctcc tgacctcgtg atccgcccgc cttggcctcc   65040
caaagtgctg ggactacaag catgagccac ccactacacc cggcccactg acagtatcaa   65100
tttttattgt gttgttactt ttagaaagtg gcagaattta aaaactgaca acactgtagg   65160
aaatttatga gcttagaaac atgagtttga ggatttgccc aactgtttta aggactccac   65220
actggggtca gatgtcacct ggaggagcat gaccgtgtct cccatatagc gcagtgtcca   65280
ggttttatgt gaagcaaaca tggccagggc ttccagaggg cttatgcaga cctgcgactg   65340
aagcaagatc aatggcaggc cgtctctagt attgtcgagg gctcctgtta actacggagc   65400
acgtaggtag attgttggca ggaaaatctg gcaggaacga tggcccctat ccttgttcca   65460
tttctctcct cagctggtta ggaccactat accctccctc tttttttttt ttttgttttt   65520
tgttttttgt cttcctttgc tttgtttaaa cagtgagggt tattggtaag aggagagccc   65580
gtgtcattcc tcactataat gctttctctc tgctttggat gtaccgataa ttgcagttca   65640
gggttcctgg aacttctacc agtgccactc tgacaggcct caccagaggt gccacctaca   65700
acgtcatagt ggaggcactg aaagaccagc agaggcataa ggttcgggaa gaggttgtta   65760
ccgtgggcaa ctctggtatg taaacacgta ctatttagac acaggctccc ctctgctgta   65820
caccagagat gggcttttct gttgactgta cctttgttgc cattgtcttt ttatctttgg   65880
gatttaatgc aacacatcaa catgaaataa atgagcaact ttatattaaa ttaatctctc   65940
```

```
ccccacctcc tgccatatcc tgttgtcttc acaaaatgca tacgtaattg acagactctc   66000
aaatggtgat atgattatag atctggaagg gatttcaaat attatttagt acaacactct   66060
gagtccttac ttctgagtat ctgagttgat atagggcaca ggtttcctga tgtcttttcc   66120
cagaccctct ccatctcacc atgctgctgt cctcttgagt gattaaatac tgaaacgatt   66180
acctataaag aaaataccccc ttctgcagac atggggacag ttggcttttg ctcctgatat   66240
aaaatgctac caacattgtg catttctgtc tgcagagaat gttattccaa tgttatttcc   66300
atttttttcc aatgttattt ccattttttt ttctgactat acaggttaaa agcttctata   66360
gaggttaaaa gatcattaac tcttctttgt agcacctggg aaatccttttt aaatcaatag   66420 cgtgccacct ggctgctcaa tttgcagcag ctgaaaattc accaaggcac atgagatagg   66480
ggataatcaa aaccgtgaat ccccaatctt ccaacaggag agttctctac tccacaccaa   66540
cagagagtgc taagtcctgt ctatgccaag tgacagattt tattcctaag gccagttgtt   66600
taattttagc cccttccctc atctgataga agactgtgct actttacatg tataaattcc   66660
tgtgaattaa gcagttgagc atttggctgg agagaggttg ggaggagatt attttgtgtt   66720
tgttgtatta catatccaca gtaatgctta tctttgcctt ttgtggtttt actagtagaa   66780
tgccacgtga acagaatttt caagagcaaa aaggtctttg tgcttttcta agtcattttt   66840
tttttttttt tttaaagatt ccatctcttt aactttagtt aggatggaat ttgaactcct   66900
ggctcttttg agtatagaaa cccctagtaa caatttaagt tccttccatt tttcttttaa   66960
actccttatt cccagcagca gtattctaca ttctaaccag gttctcccag ctttgagacg   67020
tctcagactt accagttctc caaaacgcta ttttctttaa gggtgacacc ttttaaaaat   67080
taggcacctc aaatatctac tgcttttgag cttttgagtt ttgcactgta aaagaaaaa    67140 tacacagtgg gattttaagt caaattagtt tatctaattt ttagggaata atttgaagca   67200
tgctttgttt gcatagattt ttttaaaata agcttttcca aatcataaag agataagatc   67260
ttaggtaaca tgaagagact cccttactta ttcctaaatc atctatattc caagggcatt   67320
ttcttatttg gaacagttga cctcactgat aaagctgtct caccactata ataacaatgt   67380
ccaaaatcta ggctttctgc actattatgc aaaaattaca ataataaaag tgaaaattac   67440
attataatgg tatattaaaa tgctaagact tttgcattat aagcaaaaga cagccttttaa   67500 taattattct ttatttagtg aacattttct aagtcttgga aaagggtcaa tgttttgaat   67560
tcatggcctt atataatctt cacaagattc cccaggaggt atagatattt ttattattac   67620
gctagtattg cagatgaggg aagcaaggca gagtggtatt aaatagctgg cccaaggtca   67680
ctcaggtacc aatggagagg catcattagt ctttgcatcc cactaaagtt ctccactagc   67740
ttcaattgcc tcaagatctg ttccatgttc tatgaagtag tttcaacaga aatggcaatt   67800
atcttagaag caagggaaaa ataaaagatg ggcttcctgt cgggtgcctg tgacaggtgt   67860
cacatctaac catggttttt tagagcagtt aatgccttga tagaacagat gaatgcctct   67920
taatcctcct ggaattcttg ttttagatta agtcattgta tacagtcatt cgattttctt   67980
cttatggtcc aaatcgatta ataagatgtc tcttttttgct ttttcttcct tttcttcata   68040
gtcaacgaag gcttgaacca acctacggat gactcgtgct ttgacccta  cacagtttcc    68100 cattatgccg ttggagatga gtgggaacga atgtctgaat caggctttaa actgttgtgc   68160
cagtgcttag gctttggaag tggtcatttc agatgtgatt catctagtga gtagttgctt   68220
tgtccatcca cttccgtgtt tgtctcctca agttccatgc atgcactcat gtgccaagga   68280
agcatgtttg gaagacacag gttcttccaa acatgaagca aacaagagaa tactgtttga   68340
```

```
ctcgaagtaa tattttgcat catagaaaaa tgatgggaaa ttttacttgt tggacattgc   68400
ttcatttcaa gggttgtatg ccaatacaac tattaattac acataagatt atggtgctaa   68460
tttgattttt gaaattttct gtgaaaacaa atggataaag acttttggaa ccaggtctat   68520
ttaagagtat tagagacaca gaaaaacctc aaatctcttt taatcttcag tgttgaatga   68580
gatcagaggt gaacatttag actcaaaaac agcctccttc aacataaacc aaacatgcac   68640
atatcatagt acccatgcac acactttgc gtcacacaca tagcccaggt agcttgaacg    68700
ttgctagaaa tatgaaagaa aaaacagata atctgctttt agatcattaa aaatcaactt   68760
gaattgataa atgtttgatt tcaaattct aatacgtttt aattttcaaa ttttttaagt    68820
taaaatgtgc ctaggaaata tctattatgc tttgagatta ggattagaat ttataaacct   68880
ttcatttatt ctttgtgttt aggagatgtg atgattattg acaattggtt cattttttata  68940 ggtgttgacc gttatgccta taaataagcc tcctatagac atacagaaat catatcctgt   69000
ggaattagaa tataagactt ggtaaaagag attttcaaag tattttactt aacttgtata   69060
cttgaaatca tttaatccag actgaagttg taaaagccag ccagtgtttt caatatagac   69120
ttccatgttt gaccatctga aaatgaaaaa cactaaaaac atcacatgct gtttaggagc   69180
tggaaatttt aatatttgac ttcaagtaga tggtttttaa ctcctgaaat cgaactacgt   69240
ttaagtttgt atgtttatta cctgtttgag cacttaggtg caattgtggg agcgggatg    69300 tcaagttcat ttatgtgact ctttggctca acttacataa tctttgtttt gatatcacag   69360
ttgtctaatt attttacttt gtagcttaag gcaggctgaa ttgttgataa aatggaaaaa   69420
gtagtatatt gttatataag cttctgaggt gtgttttgtt gtataagccc tggaggttaa   69480
aaagtcatcc cttatgtata gtagttaaag gcataaaact gtgacttta gatattccac     69540 agaaccagac ttatttgatg tggataataa ccaatgattt agcattttgt ttgcttttgt   69600
tttattttat ccgggttcat ttttttactct tcccatgtac atgaaacagg tggtggcgtg   69660
tagagatcag ctgatccttg ttttatggtt aattgaacta ctttgtatcc agggtttctg   69720
caaatccaaa agtgattttt catctaggat ctattcctaa cagtctactc caatcccact   69780
ttagttttcc acaattttaa atcttaatag tgagaattca aatgaaagtc atttcatttg   69840
actattctga tgacatgatt gtggcagaat aaattgggtc ttaaaatgcc ctagaaaatg   69900
gtaaatgata aaaataata ttttaaaatt caaccaaaga aatggcccat tggccaggtg    69960
tggtggctca cacctgtaat cccagcactt tggaggctg aggcgggtgg atcacctgag    70020
ctcacgagtt tgagaccagc ctacccaaca tggtaaaacc ccatctctac aaaaaataca   70080 aaaaaaaaa aaaaaaaaa aatagcactg tggggagtgc ctgtaatccc agctactcag    70140
gaggctgagg caggataact gcatgaaccc aggagatgga ggttacagtg agccgagatt   70200
gcaccacttc actccagtct gggcgacaga gaaagacttt gtctcaaaaa aaaaaaaaa    70260 aataaaagt aaataaataa ataaaataaa tggcccatta taggggtttt tatctttaac    70320
ttgctatttt tccagatcat ggttctgaag accctgtgac acgtcccagt tcacctactg   70380
tcttgtgagt cagaatatac aaataacttt ttggtcctga cttccccac ccctacagga    70440 tggtgccatg acaatggtgt gaactacaag attggagaga agtgggaccg tcaggagaa    70500 aatggccaga tgatgagctg cacatgtctt ggaacggaa aaggagaatt caagtgtgac    70560
cctcgtatgt catcacagat cattttagt gccttattaa gcattctcac tttcattatc    70620
aggctgtaac tctcattcac agaaatgatt ggagacttta ggtctccttg aggagtgaac   70680
agtgggtttc ttaatctttt gatttgggaa agtggagaca agcttcaaaa atgagtcatg   70740
```

```
atttaatgtt attacaggac actttagcac ttgtccaacc tgagtatttt gaccattatc    70800
tgcagtaaaa tgctacaaag aagctttatt ggtctgtaga ttcaactttt aaaatatgat    70860
ttccatcttc ccgttggacc ctttccagtg tattaggtct aattttttgga agtgccaccc   70920 taagatctgt atagcagtac tgctcttagg gatgattcac ataaatatgt ggtgtttgcg    70980
ctgtgatgat acaaatttag gacagaaata gaacccaccc ctagatcaag tctgcagtat    71040
tgttctcagc ttatgcgtgc atctgtcttg tgtctatatg cagatgaggc aacgtgttat    71100
gatgatggga agacatacca cgtaggagaa cagtggcaga aggaatatct cggtgccatt    71160
tgctcctgca catgctttgg aggccagcgg gtaagactgg atgtgccagg ctccctacaa    71220
gttagataag ataaagggtg ggctcctgca aggatgtgtc gtacacacag gaggggcaga    71280
gacccttcgg aagtattaaa ataccacatt tcctgttggc atacaactgc tgacatagag    71340
ctctagagca gctctatgtc taccttacat gccattcatt cttctatta ctcttagtag     71400 aaagaatgaa tgaatggcat gtagagtacc aaaaacacaa gtcttgagtc attcttaata    71460
gcaacacctg tcatttatat gatgttagaa tcattttcct aagctcccta gcatgtcaga    71520
gatactattt acactgaaaa atagtgaagc agagatacta ttcaaattaa ttagtggtaa    71580
atagaatgtg tttcatttca gccggttctc cccatcctgg gcagcctgag accctcccct    71640
cccctactat tctcaggctg cttctatttt tcagcaaagt gttaagtgca gtgtagctct    71700
aggcctccaa ctccattctg atggacaggt gtcccatggc aacgttgtta aatattttga    71760
ataatatctc agatgtaaga aaatgccact tcttttaacc tctctcttga ttcagaacag    71820
atgcttgtta taggtctagc actgtgctaa gtagtatagg aaaaacagag gaaatgagaa    71880
atggcttggc tcttaatgat atagttgaag atgttaaatt agcatacatt tcaaagtcaa    71940
gctaattaag ttcaagtggg gtctgacaaa tacagttctg ggtaggctgg aattagcaag    72000
aaagagaagc atgaactggc tgaggtttac gatgactaag gtttagttgg gaggggagaa    72060
agcagagaga cacacccccct gggatagaaa ggagctggcc caggtgggct ttggtgagcc    72120
aaccctctgc ctgctgtctt ctggtaagaa aatagatggg aagaagtggc ttatggaggg    72180
ccttggcaac ccattattta agccagtact tctcaaccat ttctaaaata tgcccagtat    72240
aacaaaaaat aataagcctt tctctaatat gatttcaaat ttcaaaatga aattatgtgt    72300
aactcaaaag caatggaatg tgacagccct ttgttttcaa cgaagacatg ccctcccagc    72360 aactcccccaa atcctggtgg gtgagggggca tgcttcacac tcaagggtga gactcattgg   72420
ttaatgccaa atgcattaac caattacagg tatccaagat gcaaagaaac atgatggaaa    72480
atagtctttg ggaaaattaa tctggcagca ggggtgttca ggggcctgtc ttggctccac    72540
caggggcagc ccatggaaac tactatgatc ttgtttcacc cccagtgatt acatggggag    72600
ggaggtgctc ccaattctga tggaggagaa ttggagattg gaatttagat tgaattcagt    72660
atctctctct gtctctctct ctctctctct cccattaaca cttacaacga ctgtgattgt    72720
atgaccttag aactcagtca ttctggtatg aaattgtgtg atggagaatg aatttgctgg    72780
gaagttgatt ttggtctcac ttcagcatct tctcattatt tatgcacatg aaacctttca    72840
tgtgcgacac ttattctatt ctcaagtgct aaatgaaaca tttaagacag gagtggaaac    72900
tgttcacttt ctcatatgaa agcaagattc agtgattctg taaggaggta gtcactggta    72960
ttgtgttagg tattaagggg catatgtgct taaacagaga aatatgtcta aaatatttaa    73020
attctaatat aaaaaagaaa gtgactgtat tatttagggc tgcattttag ttgtaagaaa    73080
aaagtccaac tcaagcaaaa atggcccaca caatggaaca gtcccaggac ccaccggctt    73140
```

```
caggggctgc tccagcaatg gcgcccggac tccctcttgc tccgcgtgcc ttcccatgca    73200
ctggcttcgt gcttcagcgg ggtctctgct gatggtgcca ttgatgactg acctccatga    73260 gcttgctttta cccctgcca gcttaagaac agtagtgaaa gagaacatgt gtgtcctccc    73320
atttccagta aaaacttcag gcaggagcct cactggctca gcttggtccc gtttccatct    73380
cccatgccat ctccgccag gtgacaggct accatgtcac tgcctaggga agtttaggaa    73440
gagagtggca aagtggtgca ttagaaagaa catggccagg tcaccccacc tcctgggcgg    73500
caggcccaac tccaccagtg gtccactgtg tgacttccct gctccctcta agcaagtcac    73560
tcctctcctc tgggtctctg tttccttacc tataaaatga gaacgtttct tcatgtgatc    73620
tcaagtccct tttaaaatcg ctaggattct ttgaaaacct tttctatcat ctagtgcaga    73680
gaacttgttg aggaagttgg gattggaatg agcctcagca gatgggcaag gtttgaatag    73740
gaagagaaga gacatttcag gagaaagaaa caacatagag agacagatgt aggtataaga    73800
tatggtaata agccaaaatg tattaagagt tataaatgca tgaaatcatc atcaaagctt    73860
gcttagtgat taactgctta tattttgcca gtgcatatga tgtgacattt ttctttaact    73920
caaacactaa attacgatgt cctcaggtta tcataaaccc catttgactt catgcctcta    73980
ctctctcagg gctggcgctg tgacaactgc cgcagacctg ggggtgaacc cagtcccgaa    74040
ggcactactg gccagtccta caaccagtat tctcagagat accatcagag aacaaacact    74100
gtaagtgcat tagcagcaca agtgtgttcc ctcatactag acagtctctt tctacaggta    74160
tctttcttca gaatgaacca agtgttttaa ttaattaaaa aaaaaaacaa ctcataaatg    74220
acttaagtga aacactgtat tccataatat agtttaagtt ataatttatg taactcttga    74280
acatctccta ttgcccagta tgctgctagg ttccttgaaac taggaagaaa tattatccta    74340
tctataagca gctgtcatga gtccccacct ccccgcattt ttttttctgt acactttaca    74400
gtatttgcca ctaatttttt tttccttctt cctttttaac agaatgttaa ttgcccaatt    74460
gagtgcttca tgcctttaga tgtacaggct gacagagaag attcccgaga gtaaatcatc    74520
tttccaatcc agaggaacaa gcatgtctct ctgccaagat ccatctaaac tggagtgatg    74580
ttagcagacc cagcttagag ttcttctttc tttcttaagc cctttgctct ggaggaagtt    74640
ctccagcttc agctcaactc acagcttctc caagcatcac cctgggagtt tcctgagggt    74700
tttctcataa atgagggctg cacattgcct gttctgcttc gaagtattca ataccgctca    74760
gtattttaaa tgaagtgatt ctaagatttg gtttgggatc aataggaaag catatgcagc    74820
caaccaagat gcaaatgttt tgaaatgata tgaccaaaat tttaagtagg aaagtcaccc    74880
aaacacttct gctttcactt aagtgtctgg cccgcaatac tgtaggaaca agcatgatct    74940
tgttactgtg atattttaaa tatccacagt actcactttt tccaaatgat cctagtaatt    75000
gcctagaaat atcttctctc tacctgttat ttatcaattt ttcccagtat ttttatacgg    75060
aaaaaattgt attgaaaaca cttagtatgc agttgataag aggaatttgg tataattatg    75120
gtgggtgatt attttttata ctgtatgtgc caaagcttta ctactgtgga aagacaactg    75180
ttttaataaa agatttacat tccacaactt gaagttcatc tatttgatat aagacacctt    75240
cgggggaaat aattcctgtg aatattcttt ttcaattcag caaacatttg aaaatctatg    75300
atgtgcaagt ctaattgttg atttcagtac aagatttct aaatcagttg ctacaaaaac    75360
tgattggttt ttgtcacttc atctcttcac taatggagat agctttacac tttctgcttt    75420
aatagattta agtggacccc aatatttatt aaaattgcta gttaccgtt cagaagtata    75480 atagaaataa tctttagttg ctcttttcta accattgtaa ttcttcccttt cttccctcca    75540
```

```
cctttccttc attgaataaa cctctgttca aagagattgc ctgcaaggga aataaaaatg   75600
actaagatat taaaa                                                   75615
```

<210> SEQ ID NO 2
<211> LENGTH: 2355
<212> TYPE: PRT
<213> ORGANISM: Homo sapiens
<220> FEATURE:
<221> NAME/KEY: MISC_FEATURE
<223> OTHER INFORMATION: Fn1 isoform 3 preproprotein

<400> SEQUENCE: 2

```
Met Leu Arg Gly Pro Gly Pro Gly Leu Leu Leu Leu Ala Val Gln Cys
 1               5                  10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
```

```
                340                 345                 350
Gly Asn Ser Asn Gly Glu Pro Cys Val Leu Pro Phe Thr Tyr Asn Gly
            355                 360                 365

Arg Thr Phe Tyr Ser Cys Thr Thr Glu Gly Arg Gln Asp Gly His Leu
        370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
            405                 410                 415

Gly Ala Leu Cys His Phe Pro Phe Leu Tyr Asn Asn His Asn Tyr Thr
        420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
        450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
            485                 490                 495

Thr Cys Val Gly Asn Gly Arg Gly Glu Trp Thr Cys Ile Ala Tyr Ser
        500                 505                 510

Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
        530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
            565                 570                 575

Glu Lys Tyr Val His Gly Val Arg Tyr Gln Cys Tyr Cys Tyr Gly Arg
        580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
        610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
            645                 650                 655

Ala Thr Ile Pro Gly His Leu Asn Ser Tyr Thr Ile Lys Gly Leu Lys
        660                 665                 670

Pro Gly Val Val Tyr Glu Gly Gln Leu Ile Ser Ile Gln Gln Tyr Gly
            675                 680                 685

His Gln Glu Val Thr Arg Phe Asp Phe Thr Thr Thr Ser Thr Ser Thr
        690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
            725                 730                 735

Val Val Ser Trp Val Ser Ala Ser Asp Thr Val Ser Gly Phe Arg Val
        740                 745                 750

Glu Tyr Glu Leu Ser Glu Glu Gly Asp Glu Pro Gln Tyr Leu Asp Leu
            755                 760                 765
```

-continued

Pro Ser Thr Ala Thr Ser Val Asn Ile Pro Asp Leu Leu Pro Gly Arg
770             775                 780

Lys Tyr Ile Val Asn Val Tyr Gln Ile Ser Glu Asp Gly Glu Gln Ser
785             790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
                820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
                900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
                980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

```
Gly Val Leu Thr Val Ser Trp Glu Arg Ser Thr Thr Pro Asp Ile
    1190                1195                1200

Thr Gly Tyr Arg Ile Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260

Ile Pro Ala Val Pro Pro Thr Asp Leu Arg Phe Thr Asn Ile
    1265                1270                1275

Gly Pro Asp Thr Met Arg Val Thr Trp Ala Pro Pro Ser Ile
    1280                1285                1290

Asp Leu Thr Asn Phe Leu Val Arg Tyr Ser Pro Val Lys Asn Glu
    1295                1300                1305

Glu Asp Val Ala Glu Leu Ser Ile Ser Pro Ser Asp Asn Ala Val
    1310                1315                1320

Val Leu Thr Asn Leu Leu Pro Gly Thr Glu Tyr Val Val Ser Val
    1325                1330                1335

Ser Ser Val Tyr Glu Gln His Glu Ser Thr Pro Leu Arg Gly Arg
    1340                1345                1350

Gln Lys Thr Gly Leu Asp Ser Pro Thr Gly Ile Asp Phe Ser Asp
    1355                1360                1365

Ile Thr Ala Asn Ser Phe Thr Val His Trp Ile Ala Pro Arg Ala
    1370                1375                1380

Thr Ile Thr Gly Tyr Arg Ile Arg His His Pro Glu His Phe Ser
    1385                1390                1395

Gly Arg Pro Arg Glu Asp Arg Val Pro His Ser Arg Asn Ser Ile
    1400                1405                1410

Thr Leu Thr Asn Leu Thr Pro Gly Thr Glu Tyr Val Val Ser Ile
    1415                1420                1425

Val Ala Leu Asn Gly Arg Glu Glu Ser Pro Leu Leu Ile Gly Gln
    1430                1435                1440

Gln Ser Thr Val Ser Asp Val Pro Arg Asp Leu Glu Val Val Ala
    1445                1450                1455

Ala Thr Pro Thr Ser Leu Leu Ile Ser Trp Asp Ala Pro Ala Val
    1460                1465                1470

Thr Val Arg Tyr Tyr Arg Ile Thr Tyr Gly Glu Thr Gly Gly Asn
    1475                1480                1485

Ser Pro Val Gln Glu Phe Thr Val Pro Gly Ser Lys Ser Thr Ala
    1490                1495                1500

Thr Ile Ser Gly Leu Lys Pro Gly Val Asp Tyr Thr Ile Thr Val
    1505                1510                1515

Tyr Ala Val Thr Gly Arg Gly Asp Ser Pro Ala Ser Ser Lys Pro
    1520                1525                1530

Ile Ser Ile Asn Tyr Arg Thr Glu Ile Asp Lys Pro Ser Gln Met
    1535                1540                1545

Gln Val Thr Asp Val Gln Asp Asn Ser Ile Ser Val Lys Trp Leu
    1550                1555                1560

Pro Ser Ser Ser Pro Val Thr Gly Tyr Arg Val Thr Thr Thr Pro
    1565                1570                1575

Lys Asn Gly Pro Gly Pro Thr Lys Thr Lys Thr Ala Gly Pro Asp
```

-continued

```
           1580              1585              1590

Gln Thr Glu Met Thr Ile Glu Gly Leu Gln Pro Thr Val Glu Tyr
    1595              1600              1605

Val Val Ser Val Tyr Ala Gln Asn Pro Ser Gly Glu Ser Gln Pro
    1610              1615              1620

Leu Val Gln Thr Ala Val Thr Asn Ile Asp Arg Pro Lys Gly Leu
    1625              1630              1635

Ala Phe Thr Asp Val Asp Val Asp Ser Ile Lys Ile Ala Trp Glu
    1640              1645              1650

Ser Pro Gln Gly Gln Val Ser Arg Tyr Arg Val Thr Tyr Ser Ser
    1655              1660              1665

Pro Glu Asp Gly Ile His Glu Leu Phe Pro Ala Pro Asp Gly Glu
    1670              1675              1680

Glu Asp Thr Ala Glu Leu Gln Gly Leu Arg Pro Gly Ser Glu Tyr
    1685              1690              1695

Thr Val Ser Val Val Ala Leu His Asp Asp Met Glu Ser Gln Pro
    1700              1705              1710

Leu Ile Gly Thr Gln Ser Thr Ala Ile Pro Ala Pro Thr Asp Leu
    1715              1720              1725

Lys Phe Thr Gln Val Thr Pro Thr Ser Leu Ser Ala Gln Trp Thr
    1730              1735              1740

Pro Pro Asn Val Gln Leu Thr Gly Tyr Arg Val Arg Val Thr Pro
    1745              1750              1755

Lys Glu Lys Thr Gly Pro Met Lys Glu Ile Asn Leu Ala Pro Asp
    1760              1765              1770

Ser Ser Ser Val Val Val Ser Gly Leu Met Val Ala Thr Lys Tyr
    1775              1780              1785

Glu Val Ser Val Tyr Ala Leu Lys Asp Thr Leu Thr Ser Arg Pro
    1790              1795              1800

Ala Gln Gly Val Val Thr Thr Leu Glu Asn Val Ser Pro Pro Arg
    1805              1810              1815

Arg Ala Arg Val Thr Asp Ala Thr Glu Thr Thr Ile Thr Ile Ser
    1820              1825              1830

Trp Arg Thr Lys Thr Glu Thr Ile Thr Gly Phe Gln Val Asp Ala
    1835              1840              1845

Val Pro Ala Asn Gly Gln Thr Pro Ile Gln Arg Thr Ile Lys Pro
    1850              1855              1860

Asp Val Arg Ser Tyr Thr Ile Thr Gly Leu Gln Pro Gly Thr Asp
    1865              1870              1875

Tyr Lys Ile Tyr Leu Tyr Thr Leu Asn Asp Asn Ala Arg Ser Ser
    1880              1885              1890

Pro Val Val Ile Asp Ala Ser Thr Ala Ile Asp Ala Pro Ser Asn
    1895              1900              1905

Leu Arg Phe Leu Ala Thr Thr Pro Asn Ser Leu Leu Val Ser Trp
    1910              1915              1920

Gln Pro Pro Arg Ala Arg Ile Thr Gly Tyr Ile Ile Lys Tyr Glu
    1925              1930              1935

Lys Pro Gly Ser Pro Pro Arg Glu Val Val Pro Arg Pro Arg Pro
    1940              1945              1950

Gly Val Thr Glu Ala Thr Ile Thr Gly Leu Glu Pro Gly Thr Glu
    1955              1960              1965

Tyr Thr Ile Tyr Val Ile Ala Leu Lys Asn Asn Gln Lys Ser Glu
    1970              1975              1980
```

-continued

Pro Leu Ile Gly Arg Lys Lys Thr Asp Glu Leu Pro Gln Leu Val
1985            1990                1995

Thr Leu Pro His Pro Asn Leu His Gly Pro Glu Ile Leu Asp Val
2000            2005                2010

Pro Ser Thr Val Gln Lys Thr Pro Phe Val Thr His Pro Gly Tyr
2015            2020                2025

Asp Thr Gly Asn Gly Ile Gln Leu Pro Gly Thr Ser Gly Gln Gln
2030            2035                2040

Pro Ser Val Gly Gln Gln Met Ile Phe Glu Glu His Gly Phe Arg
2045            2050                2055

Arg Thr Thr Pro Pro Thr Thr Ala Thr Pro Ile Arg His Arg Pro
2060            2065                2070

Arg Pro Tyr Pro Pro Asn Val Gly Gln Glu Ala Leu Ser Gln Thr
2075            2080                2085

Thr Ile Ser Trp Ala Pro Phe Gln Asp Thr Ser Glu Tyr Ile Ile
2090            2095                2100

Ser Cys His Pro Val Gly Thr Asp Glu Glu Pro Leu Gln Phe Arg
2105            2110                2115

Val Pro Gly Thr Ser Thr Ser Ala Thr Leu Thr Gly Leu Thr Arg
2120            2125                2130

Gly Ala Thr Tyr Asn Ile Ile Val Glu Ala Leu Lys Asp Gln Gln
2135            2140                2145

Arg His Lys Val Arg Glu Glu Val Val Thr Val Gly Asn Ser Val
2150            2155                2160

Asn Glu Gly Leu Asn Gln Pro Thr Asp Asp Ser Cys Phe Asp Pro
2165            2170                2175

Tyr Thr Val Ser His Tyr Ala Val Gly Asp Glu Trp Glu Arg Met
2180            2185                2190

Ser Glu Ser Gly Phe Lys Leu Leu Cys Gln Cys Leu Gly Phe Gly
2195            2200                2205

Ser Gly His Phe Arg Cys Asp Ser Ser Arg Trp Cys His Asp Asn
2210            2215                2220

Gly Val Asn Tyr Lys Ile Gly Glu Lys Trp Asp Arg Gln Gly Glu
2225            2230                2235

Asn Gly Gln Met Met Ser Cys Thr Cys Leu Gly Asn Gly Lys Gly
2240            2245                2250

Glu Phe Lys Cys Asp Pro His Glu Ala Thr Cys Tyr Asp Asp Gly
2255            2260                2265

Lys Thr Tyr His Val Gly Glu Gln Trp Gln Lys Glu Tyr Leu Gly
2270            2275                2280

Ala Ile Cys Ser Cys Thr Cys Phe Gly Gly Gln Arg Gly Trp Arg
2285            2290                2295

Cys Asp Asn Cys Arg Arg Pro Gly Gly Glu Pro Ser Pro Glu Gly
2300            2305                2310

Thr Thr Gly Gln Ser Tyr Asn Gln Tyr Ser Gln Arg Tyr His Gln
2315            2320                2325

Arg Thr Asn Thr Asn Val Asn Cys Pro Ile Glu Cys Phe Met Pro
2330            2335                2340

Leu Asp Val Gln Ala Asp Arg Glu Asp Ser Arg Glu
2345            2350                2355

<210> SEQ ID NO 3
<211> LENGTH: 657
<212> TYPE: PRT
<213> ORGANISM: Homo sapiens -continued

```
<220> FEATURE:
<221> NAME/KEY: MISC_FEATURE
<223> OTHER INFORMATION: Fn1 isoform 7 preproprotein

<400> SEQUENCE: 3

Met Leu Arg Gly Pro Gly Pro Gly Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
                35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
                100                 105                 110

Glu Arg Pro Lys Asp Ser Met Ile Trp Asp Cys Thr Cys Ile Gly Ala
                115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
                180                 185                 190

Thr Ser Tyr Val Val Gly Glu Thr Trp Glu Lys Pro Tyr Gln Gly Trp
                195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
                260                 265                 270

His Thr Ser Val Gln Thr Thr Ser Ser Gly Ser Gly Pro Phe Thr Asp
    275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
                340                 345                 350

Gly Asn Ser Asn Gly Glu Pro Cys Val Leu Pro Phe Thr Tyr Asn Gly
                355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400
```

```
Cys Thr Asp His Thr Val Leu Val Gln Thr Arg Gly Gly Asn Ser Asn
            405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
        450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
                500                 505                 510

Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
            530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
                580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
            610                 615                 620

Ser His Pro Ile Gln Trp Asn Ala Pro Gln Pro Ser His Ile Ser Lys
625                 630                 635                 640

Tyr Ile Leu Arg Trp Arg Pro Val Ser Ile Pro Pro Arg Asn Leu Gly
                645                 650                 655

Tyr
```

<210> SEQ ID NO 4
<211> LENGTH: 2176
<212> TYPE: PRT
<213> ORGANISM: Homo sapiens
<220> FEATURE:
<221> NAME/KEY: MISC_FEATURE
<223> OTHER INFORMATION: Fn1 isoform 6 preproprotein

<400> SEQUENCE: 4

```
Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
        50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95
```

```
Cys Phe Asp Lys Tyr Thr Gly Asn Thr Tyr Arg Val Gly Asp Thr Tyr
                100                 105                 110

Glu Arg Pro Lys Asp Ser Met Ile Trp Asp Cys Thr Cys Ile Gly Ala
            115                 120                 125

Gly Arg Gly Arg Ile Ser Cys Thr Ile Ala Asn Arg Cys His Glu Gly
        130                 135                 140

Gly Gln Ser Tyr Lys Ile Gly Asp Thr Trp Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525
```

```
Asp Thr Phe His Lys Arg His Glu Glu Gly His Met Leu Asn Cys Thr
    530                 535                 540
Cys Phe Gly Gln Gly Arg Gly Arg Trp Lys Cys Asp Pro Val Asp Gln
545                 550                 555                 560
Cys Gln Asp Ser Glu Thr Gly Thr Phe Tyr Gln Ile Gly Asp Ser Trp
                565                 570                 575
Glu Lys Tyr Val His Gly Val Arg Tyr Gln Cys Tyr Cys Tyr Gly Arg
            580                 585                 590
Gly Ile Gly Glu Trp His Cys Gln Pro Leu Gln Thr Tyr Pro Ser Ser
        595                 600                 605
Ser Gly Pro Val Glu Val Phe Ile Thr Glu Thr Pro Ser Gln Pro Asn
    610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
                645                 650                 655
Ala Thr Ile Pro Gly His Leu Asn Ser Tyr Thr Ile Lys Gly Leu Lys
            660                 665                 670
Pro Gly Val Val Tyr Glu Gly Gln Leu Ile Ser Ile Gln Gln Tyr Gly
        675                 680                 685
His Gln Glu Val Thr Arg Phe Asp Phe Thr Thr Thr Ser Thr Ser Thr
    690                 695                 700
Pro Val Thr Ser Asn Thr Val Thr Gly Glu Thr Thr Pro Phe Ser Pro
705                 710                 715                 720
Leu Val Ala Thr Ser Glu Ser Val Thr Glu Ile Thr Ala Ser Ser Phe
                725                 730                 735
Val Val Ser Trp Val Ser Ala Ser Asp Thr Val Ser Gly Phe Arg Val
            740                 745                 750
Glu Tyr Glu Leu Ser Glu Glu Gly Asp Glu Pro Gln Tyr Leu Asp Leu
        755                 760                 765
Pro Ser Thr Ala Thr Ser Val Asn Ile Pro Asp Leu Leu Pro Gly Arg
    770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Pro Asp
                805                 810                 815
Pro Thr Val Asp Gln Val Asp Asp Thr Ser Ile Val Val Arg Trp Ser
            820                 825                 830
Arg Pro Gln Ala Pro Ile Thr Gly Tyr Arg Ile Val Tyr Ser Pro Ser
        835                 840                 845
Val Glu Gly Ser Ser Thr Glu Leu Asn Leu Pro Glu Thr Ala Asn Ser
    850                 855                 860
Val Thr Leu Ser Asp Leu Gln Pro Gly Val Gln Tyr Asn Ile Thr Ile
865                 870                 875                 880
Tyr Ala Val Glu Glu Asn Gln Glu Ser Thr Pro Val Val Ile Gln Gln
                885                 890                 895
Glu Thr Thr Gly Thr Pro Arg Ser Asp Thr Val Pro Ser Pro Arg Asp
            900                 905                 910
Leu Gln Phe Val Glu Val Thr Asp Val Lys Val Thr Ile Met Trp Thr
        915                 920                 925
Pro Pro Glu Ser Ala Val Thr Gly Tyr Arg Val Asp Val Ile Pro Val
    930                 935                 940
Asn Leu Pro Gly Glu His Gly Gln Arg Leu Pro Ile Ser Arg Asn Thr
```

-continued

```
            945                 950                 955                 960
        Phe Ala Glu Val Thr Gly Leu Ser Pro Gly Val Thr Tyr Tyr Phe Lys
                        965                 970                 975
        Val Phe Ala Val Ser His Gly Arg Glu Ser Lys Pro Leu Thr Ala Gln
                        980                 985                 990
        Gln Thr Thr Lys Leu Asp Ala Pro Thr Asn Leu Gln Phe Val Asn Glu
                    995                 1000                1005
        Thr Asp Ser Thr Val Leu Val Arg Trp Thr Pro Pro Arg Ala Gln
                1010                1015                1020
        Ile Thr Gly Tyr Arg Leu Thr Val Gly Leu Thr Arg Arg Gly Gln
                1025                1030                1035
        Pro Arg Gln Tyr Asn Val Gly Pro Ser Val Ser Lys Tyr Pro Leu
                1040                1045                1050
        Arg Asn Leu Gln Pro Ala Ser Glu Tyr Thr Val Ser Leu Val Ala
                1055                1060                1065
        Ile Lys Gly Asn Gln Glu Ser Pro Lys Ala Thr Gly Val Phe Thr
                1070                1075                1080
        Thr Leu Gln Pro Gly Ser Ser Ile Pro Pro Tyr Asn Thr Glu Val
                1085                1090                1095
        Thr Glu Thr Thr Ile Val Ile Thr Trp Thr Pro Ala Pro Arg Ile
                1100                1105                1110
        Gly Phe Lys Leu Gly Val Arg Pro Ser Gln Gly Gly Glu Ala Pro
                1115                1120                1125
        Arg Glu Val Thr Ser Asp Ser Gly Ser Ile Val Val Ser Gly Leu
                1130                1135                1140
        Thr Pro Gly Val Glu Tyr Val Tyr Thr Ile Gln Val Leu Arg Asp
                1145                1150                1155
        Gly Gln Glu Arg Asp Ala Pro Ile Val Asn Lys Val Val Thr Pro
                1160                1165                1170
        Leu Ser Pro Pro Thr Asn Leu His Leu Glu Ala Asn Pro Asp Thr
                1175                1180                1185
        Gly Val Leu Thr Val Ser Trp Glu Arg Ser Thr Thr Pro Asp Ile
                1190                1195                1200
        Thr Gly Tyr Arg Ile Thr Thr Thr Pro Thr Asn Gly Gln Gln Gly
                1205                1210                1215
        Asn Ser Leu Glu Glu Val Val His Ala Asp Gln Ser Ser Cys Thr
                1220                1225                1230
        Phe Asp Asn Leu Ser Pro Gly Leu Glu Tyr Asn Val Ser Val Tyr
                1235                1240                1245
        Thr Val Lys Asp Asp Lys Glu Ser Val Pro Ile Ser Asp Thr Ile
                1250                1255                1260
        Ile Pro Ala Val Pro Pro Pro Thr Asp Leu Arg Phe Thr Asn Ile
                1265                1270                1275
        Gly Pro Asp Thr Met Arg Val Thr Trp Ala Pro Pro Pro Ser Ile
                1280                1285                1290
        Asp Leu Thr Asn Phe Leu Val Arg Tyr Ser Pro Val Lys Asn Glu
                1295                1300                1305
        Glu Asp Val Ala Glu Leu Ser Ile Ser Pro Ser Asp Asn Ala Val
                1310                1315                1320
        Val Leu Thr Asn Leu Leu Pro Gly Thr Glu Tyr Val Val Ser Val
                1325                1330                1335
        Ser Ser Val Tyr Glu Gln His Glu Ser Thr Pro Leu Arg Gly Arg
                1340                1345                1350
```

-continued

```
Gln Lys Thr Gly Leu Asp Ser Pro Thr Gly Ile Asp Phe Ser Asp
1355                1360                1365

Ile Thr Ala Asn Ser Phe Thr Val His Trp Ile Ala Pro Arg Ala
1370                1375                1380

Thr Ile Thr Gly Tyr Arg Ile Arg His His Pro Glu His Phe Ser
1385                1390                1395

Gly Arg Pro Arg Glu Asp Arg Val Pro His Ser Arg Asn Ser Ile
1400                1405                1410

Thr Leu Thr Asn Leu Thr Pro Gly Thr Glu Tyr Val Val Ser Ile
1415                1420                1425

Val Ala Leu Asn Gly Arg Glu Glu Ser Pro Leu Leu Ile Gly Gln
1430                1435                1440

Gln Ser Thr Val Ser Asp Val Pro Arg Asp Leu Glu Val Val Ala
1445                1450                1455

Ala Thr Pro Thr Ser Leu Leu Ile Ser Trp Asp Ala Pro Ala Val
1460                1465                1470

Thr Val Arg Tyr Tyr Arg Ile Thr Tyr Gly Glu Thr Gly Gly Asn
1475                1480                1485

Ser Pro Val Gln Glu Phe Thr Val Pro Gly Ser Lys Ser Thr Ala
1490                1495                1500

Thr Ile Ser Gly Leu Lys Pro Gly Val Asp Tyr Thr Ile Thr Val
1505                1510                1515

Tyr Ala Val Thr Gly Arg Gly Asp Ser Pro Ala Ser Ser Lys Pro
1520                1525                1530

Ile Ser Ile Asn Tyr Arg Thr Glu Ile Asp Lys Pro Ser Gln Met
1535                1540                1545

Gln Val Thr Asp Val Gln Asp Asn Ser Ile Ser Val Lys Trp Leu
1550                1555                1560

Pro Ser Ser Ser Pro Val Thr Gly Tyr Arg Val Thr Thr Thr Pro
1565                1570                1575

Lys Asn Gly Pro Gly Pro Thr Lys Thr Lys Thr Ala Gly Pro Asp
1580                1585                1590

Gln Thr Glu Met Thr Ile Glu Gly Leu Gln Pro Thr Val Glu Tyr
1595                1600                1605

Val Val Ser Val Tyr Ala Gln Asn Pro Ser Gly Glu Ser Gln Pro
1610                1615                1620

Leu Val Gln Thr Ala Val Thr Thr Ile Pro Ala Pro Thr Asp Leu
1625                1630                1635

Lys Phe Thr Gln Val Thr Pro Thr Ser Leu Ser Ala Gln Trp Thr
1640                1645                1650

Pro Pro Asn Val Gln Leu Thr Gly Tyr Arg Val Arg Val Thr Pro
1655                1660                1665

Lys Glu Lys Thr Gly Pro Met Lys Glu Ile Asn Leu Ala Pro Asp
1670                1675                1680

Ser Ser Ser Val Val Val Ser Gly Leu Met Val Ala Thr Lys Tyr
1685                1690                1695

Glu Val Ser Val Tyr Ala Leu Lys Asp Thr Leu Thr Ser Arg Pro
1700                1705                1710

Ala Gln Gly Val Val Thr Thr Leu Glu Asn Val Ser Pro Pro Arg
1715                1720                1725

Arg Ala Arg Val Thr Asp Ala Thr Glu Thr Thr Ile Thr Ile Ser
1730                1735                1740

Trp Arg Thr Lys Thr Glu Thr Ile Thr Gly Phe Gln Val Asp Ala
1745                1750                1755
```

-continued

```
Val Pro Ala Asn Gly Gln Thr Pro Ile Gln Arg Thr Ile Lys Pro
    1760                1765                1770

Asp Val Arg Ser Tyr Thr Ile Thr Gly Leu Gln Pro Gly Thr Asp
    1775                1780                1785

Tyr Lys Ile Tyr Leu Tyr Thr Leu Asn Asp Asn Ala Arg Ser Ser
    1790                1795                1800

Pro Val Val Ile Asp Ala Ser Thr Ala Ile Asp Ala Pro Ser Asn
    1805                1810                1815

Leu Arg Phe Leu Ala Thr Thr Pro Asn Ser Leu Leu Val Ser Trp
    1820                1825                1830

Gln Pro Pro Arg Ala Arg Ile Thr Gly Tyr Ile Ile Lys Tyr Glu
    1835                1840                1845

Lys Pro Gly Ser Pro Pro Arg Glu Val Val Pro Arg Pro Arg Pro
    1850                1855                1860

Gly Val Thr Glu Ala Thr Ile Thr Gly Leu Glu Pro Gly Thr Glu
    1865                1870                1875

Tyr Thr Ile Tyr Val Ile Ala Leu Lys Asn Asn Gln Lys Ser Glu
    1880                1885                1890

Pro Leu Ile Gly Arg Lys Lys Thr Gly Gln Glu Ala Leu Ser Gln
    1895                1900                1905

Thr Thr Ile Ser Trp Ala Pro Phe Gln Asp Thr Ser Glu Tyr Ile
    1910                1915                1920

Ile Ser Cys His Pro Val Gly Thr Asp Glu Glu Pro Leu Gln Phe
    1925                1930                1935

Arg Val Pro Gly Thr Ser Thr Ser Ala Thr Leu Thr Gly Leu Thr
    1940                1945                1950

Arg Gly Ala Thr Tyr Asn Ile Ile Val Glu Ala Leu Lys Asp Gln
    1955                1960                1965

Gln Arg His Lys Val Arg Glu Glu Val Val Thr Val Gly Asn Ser
    1970                1975                1980

Val Asn Glu Gly Leu Asn Gln Pro Thr Asp Asp Ser Cys Phe Asp
    1985                1990                1995

Pro Tyr Thr Val Ser His Tyr Ala Val Gly Asp Glu Trp Glu Arg
    2000                2005                2010

Met Ser Glu Ser Gly Phe Lys Leu Leu Cys Gln Cys Leu Gly Phe
    2015                2020                2025

Gly Ser Gly His Phe Arg Cys Asp Ser Ser Arg Trp Cys His Asp
    2030                2035                2040

Asn Gly Val Asn Tyr Lys Ile Gly Glu Lys Trp Asp Arg Gln Gly
    2045                2050                2055

Glu Asn Gly Gln Met Met Ser Cys Thr Cys Leu Gly Asn Gly Lys
    2060                2065                2070

Gly Glu Phe Lys Cys Asp Pro His Glu Ala Thr Cys Tyr Asp Asp
    2075                2080                2085

Gly Lys Thr Tyr His Val Gly Glu Gln Trp Gln Lys Glu Tyr Leu
    2090                2095                2100

Gly Ala Ile Cys Ser Cys Thr Cys Phe Gly Gly Gln Arg Gly Trp
    2105                2110                2115

Arg Cys Asp Asn Cys Arg Arg Pro Gly Gly Glu Pro Ser Pro Glu
    2120                2125                2130

Gly Thr Thr Gly Gln Ser Tyr Asn Gln Tyr Ser Gln Arg Tyr His
    2135                2140                2145

Gln Arg Thr Asn Thr Asn Val Asn Cys Pro Ile Glu Cys Phe Met
```

```
                  2150                2155                2160
Pro  Leu  Asp  Val  Gln  Ala  Asp  Arg  Glu  Asp  Ser  Arg  Glu
     2165                2170                2175

<210> SEQ ID NO 5
<211> LENGTH: 2421
<212> TYPE: PRT
<213> ORGANISM: Homo sapiens
<220> FEATURE:
<221> NAME/KEY: MISC_FEATURE
<223> OTHER INFORMATION: Fn1 isoform 2 preproprotein

<400> SEQUENCE: 5

Met  Leu  Arg  Gly  Pro  Gly  Pro  Gly  Leu  Leu  Leu  Leu  Ala  Val  Gln  Cys
1                   5                   10                  15

Leu  Gly  Thr  Ala  Val  Pro  Ser  Thr  Gly  Ala  Ser  Lys  Ser  Lys  Arg  Gln
                20                  25                  30

Ala  Gln  Gln  Met  Val  Gln  Pro  Gln  Ser  Pro  Val  Ala  Val  Ser  Gln  Ser
            35                  40                  45

Lys  Pro  Gly  Cys  Tyr  Asp  Asn  Gly  Lys  His  Tyr  Gln  Ile  Asn  Gln  Gln
        50                  55                  60

Trp  Glu  Arg  Thr  Tyr  Leu  Gly  Asn  Ala  Leu  Val  Cys  Thr  Cys  Tyr  Gly
65                  70                  75                  80

Gly  Ser  Arg  Gly  Phe  Asn  Cys  Glu  Ser  Lys  Pro  Glu  Ala  Glu  Glu  Thr
                85                  90                  95

Cys  Phe  Asp  Lys  Tyr  Thr  Gly  Asn  Thr  Tyr  Arg  Val  Gly  Asp  Thr  Tyr
            100                 105                 110

Glu  Arg  Pro  Lys  Asp  Ser  Met  Ile  Trp  Asp  Cys  Thr  Cys  Ile  Gly  Ala
        115                 120                 125

Gly  Arg  Gly  Arg  Ile  Ser  Cys  Thr  Ile  Ala  Asn  Arg  Cys  His  Glu  Gly
    130                 135                 140

Gly  Gln  Ser  Tyr  Lys  Ile  Gly  Asp  Thr  Trp  Arg  Arg  Pro  His  Glu  Thr
145                 150                 155                 160

Gly  Gly  Tyr  Met  Leu  Glu  Cys  Val  Cys  Leu  Gly  Asn  Gly  Lys  Gly  Glu
                165                 170                 175

Trp  Thr  Cys  Lys  Pro  Ile  Ala  Glu  Lys  Cys  Phe  Asp  His  Ala  Ala  Gly
            180                 185                 190

Thr  Ser  Tyr  Val  Val  Gly  Glu  Thr  Trp  Glu  Lys  Pro  Tyr  Gln  Gly  Trp
        195                 200                 205

Met  Met  Val  Asp  Cys  Thr  Cys  Leu  Gly  Glu  Gly  Ser  Gly  Arg  Ile  Thr
    210                 215                 220

Cys  Thr  Ser  Arg  Asn  Arg  Cys  Asn  Asp  Gln  Asp  Thr  Arg  Thr  Ser  Tyr
225                 230                 235                 240

Arg  Ile  Gly  Asp  Thr  Trp  Ser  Lys  Lys  Asp  Asn  Arg  Gly  Asn  Leu  Leu
                245                 250                 255

Gln  Cys  Ile  Cys  Thr  Gly  Asn  Gly  Arg  Gly  Glu  Trp  Lys  Cys  Glu  Arg
            260                 265                 270

His  Thr  Ser  Val  Gln  Thr  Thr  Ser  Ser  Gly  Ser  Gly  Pro  Phe  Thr  Asp
        275                 280                 285

Val  Arg  Ala  Ala  Val  Tyr  Gln  Pro  Gln  Pro  His  Pro  Gln  Pro  Pro  Pro
    290                 295                 300

Tyr  Gly  His  Cys  Val  Thr  Asp  Ser  Gly  Val  Val  Tyr  Ser  Val  Gly  Met
305                 310                 315                 320

Gln  Trp  Leu  Lys  Thr  Gln  Gly  Asn  Lys  Gln  Met  Leu  Cys  Thr  Cys  Leu
                325                 330                 335

Gly  Asn  Gly  Val  Ser  Cys  Gln  Glu  Thr  Ala  Val  Thr  Gln  Thr  Tyr  Gly
```

```
                    340                 345                 350
Gly Asn Ser Asn Gly Glu Pro Cys Val Leu Pro Phe Thr Tyr Asn Gly
                355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
                420                 425                 430

Asp Cys Thr Ser Glu Gly Arg Arg Asp Asn Met Lys Trp Cys Gly Thr
                435                 440                 445

Thr Gln Asn Tyr Asp Ala Asp Gln Lys Phe Gly Phe Cys Pro Met Ala
            450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
                500                 505                 510

Gln Leu Arg Asp Gln Cys Ile Val Asp Asp Ile Thr Tyr Asn Val Asn
                515                 520                 525

Asp Thr Phe His Lys Arg His Glu Glu Gly His Met Leu Asn Cys Thr
                530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
                580                 585                 590

Gly Ile Gly Glu Trp His Cys Gln Pro Leu Gln Thr Tyr Pro Ser Ser
                595                 600                 605

Ser Gly Pro Val Glu Val Phe Ile Thr Glu Thr Pro Ser Gln Pro Asn
                610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
                660                 665                 670

Pro Gly Val Val Tyr Glu Gly Gln Leu Ile Ser Ile Gln Gln Tyr Gly
                675                 680                 685

His Gln Glu Val Thr Arg Phe Asp Phe Thr Thr Thr Ser Thr Ser Thr
                690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
                740                 745                 750

Glu Tyr Glu Leu Ser Glu Glu Gly Asp Glu Pro Gln Tyr Leu Asp Leu
                755                 760                 765
```

```
Pro Ser Thr Ala Thr Ser Val Asn Ile Pro Asp Leu Leu Pro Gly Arg
770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185
```

```
Gly Val Leu Thr Val Ser Trp Glu Arg Ser Thr Pro Asp Ile
    1190                1195                1200

Thr Gly Tyr Arg Ile Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260

Ile Pro Glu Val Pro Gln Leu Thr Asp Leu Ser Phe Val Asp Ile
    1265                1270                1275

Thr Asp Ser Ser Ile Gly Leu Arg Trp Thr Pro Leu Asn Ser Ser
    1280                1285                1290

Thr Ile Ile Gly Tyr Arg Ile Thr Val Val Ala Ala Gly Glu Gly
    1295                1300                1305

Ile Pro Ile Phe Glu Asp Phe Val Asp Ser Ser Val Gly Tyr Tyr
    1310                1315                1320

Thr Val Thr Gly Leu Glu Pro Gly Ile Asp Tyr Asp Ile Ser Val
    1325                1330                1335

Ile Thr Leu Ile Asn Gly Gly Glu Ser Ala Pro Thr Thr Leu Thr
    1340                1345                1350

Gln Gln Thr Ala Val Pro Pro Pro Thr Asp Leu Arg Phe Thr Asn
    1355                1360                1365

Ile Gly Pro Asp Thr Met Arg Val Thr Trp Ala Pro Pro Pro Ser
    1370                1375                1380

Ile Asp Leu Thr Asn Phe Leu Val Arg Tyr Ser Pro Val Lys Asn
    1385                1390                1395

Glu Glu Asp Val Ala Glu Leu Ser Ile Ser Pro Ser Asp Asn Ala
    1400                1405                1410

Val Val Leu Thr Asn Leu Leu Pro Gly Thr Glu Tyr Val Val Ser
    1415                1420                1425

Val Ser Ser Val Tyr Glu Gln His Glu Ser Thr Pro Leu Arg Gly
    1430                1435                1440

Arg Gln Lys Thr Gly Leu Asp Ser Pro Thr Gly Ile Asp Phe Ser
    1445                1450                1455

Asp Ile Thr Ala Asn Ser Phe Thr Val His Trp Ile Ala Pro Arg
    1460                1465                1470

Ala Thr Ile Thr Gly Tyr Arg Ile Arg His His Pro Glu His Phe
    1475                1480                1485

Ser Gly Arg Pro Arg Glu Asp Arg Val Pro His Ser Arg Asn Ser
    1490                1495                1500

Ile Thr Leu Thr Asn Leu Thr Pro Gly Thr Glu Tyr Val Val Ser
    1505                1510                1515

Ile Val Ala Leu Asn Gly Arg Glu Glu Ser Pro Leu Leu Ile Gly
    1520                1525                1530

Gln Gln Ser Thr Val Ser Asp Val Pro Arg Asp Leu Glu Val Val
    1535                1540                1545

Ala Ala Thr Pro Thr Ser Leu Leu Ile Ser Trp Asp Ala Pro Ala
    1550                1555                1560

Val Thr Val Arg Tyr Tyr Arg Ile Thr Tyr Gly Glu Thr Gly Gly
    1565                1570                1575

Asn Ser Pro Val Gln Glu Phe Thr Val Pro Gly Ser Lys Ser Thr
```

-continued

```
            1580                1585                1590
Ala Thr Ile Ser Gly Leu Lys Pro Gly Val Asp Tyr Thr Ile Thr
    1595                1600                1605
Val Tyr Ala Val Thr Gly Arg Gly Asp Ser Pro Ala Ser Ser Lys
    1610                1615                1620
Pro Ile Ser Ile Asn Tyr Arg Thr Glu Ile Asp Lys Pro Ser Gln
    1625                1630                1635
Met Gln Val Thr Asp Val Gln Asp Asn Ser Ile Ser Val Lys Trp
    1640                1645                1650
Leu Pro Ser Ser Ser Pro Val Thr Gly Tyr Arg Val Thr Thr Thr
    1655                1660                1665
Pro Lys Asn Gly Pro Gly Pro Thr Lys Thr Lys Thr Ala Gly Pro
    1670                1675                1680
Asp Gln Thr Glu Met Thr Ile Glu Gly Leu Gln Pro Thr Val Glu
    1685                1690                1695
Tyr Val Val Ser Val Tyr Ala Gln Asn Pro Ser Gly Glu Ser Gln
    1700                1705                1710
Pro Leu Val Gln Thr Ala Val Thr Asn Ile Asp Arg Pro Lys Gly
    1715                1720                1725
Leu Ala Phe Thr Asp Val Asp Val Asp Ser Ile Lys Ile Ala Trp
    1730                1735                1740
Glu Ser Pro Gln Gly Gln Val Ser Arg Tyr Arg Val Thr Tyr Ser
    1745                1750                1755
Ser Pro Glu Asp Gly Ile His Glu Leu Phe Pro Ala Pro Asp Gly
    1760                1765                1770
Glu Glu Asp Thr Ala Glu Leu Gln Gly Leu Arg Pro Gly Ser Glu
    1775                1780                1785
Tyr Thr Val Ser Val Val Ala Leu His Asp Asp Met Glu Ser Gln
    1790                1795                1800
Pro Leu Ile Gly Thr Gln Ser Thr Ala Ile Pro Ala Pro Thr Asp
    1805                1810                1815
Leu Lys Phe Thr Gln Val Thr Pro Thr Ser Leu Ser Ala Gln Trp
    1820                1825                1830
Thr Pro Pro Asn Val Gln Leu Thr Gly Tyr Arg Val Arg Val Thr
    1835                1840                1845
Pro Lys Glu Lys Thr Gly Pro Met Lys Glu Ile Asn Leu Ala Pro
    1850                1855                1860
Asp Ser Ser Ser Val Val Val Ser Gly Leu Met Val Ala Thr Lys
    1865                1870                1875
Tyr Glu Val Ser Val Tyr Ala Leu Lys Asp Thr Leu Thr Ser Arg
    1880                1885                1890
Pro Ala Gln Gly Val Val Thr Thr Leu Glu Asn Val Ser Pro Pro
    1895                1900                1905
Arg Arg Ala Arg Val Thr Asp Ala Thr Glu Thr Thr Ile Thr Ile
    1910                1915                1920
Ser Trp Arg Thr Lys Thr Glu Thr Ile Thr Gly Phe Gln Val Asp
    1925                1930                1935
Ala Val Pro Ala Asn Gly Gln Thr Pro Ile Gln Arg Thr Ile Lys
    1940                1945                1950
Pro Asp Val Arg Ser Tyr Thr Ile Thr Gly Leu Gln Pro Gly Thr
    1955                1960                1965
Asp Tyr Lys Ile Tyr Leu Tyr Thr Leu Asn Asp Asn Ala Arg Ser
    1970                1975                1980
```

-continued

Ser Pro Val Val Ile Asp Ala Ser Thr Ala Ile Asp Ala Pro Ser
1985            1990            1995

Asn Leu Arg Phe Leu Ala Thr Thr Pro Asn Ser Leu Leu Val Ser
2000            2005            2010

Trp Gln Pro Pro Arg Ala Arg Ile Thr Gly Tyr Ile Ile Lys Tyr
2015            2020            2025

Glu Lys Pro Gly Ser Pro Pro Arg Glu Val Val Pro Arg Pro Arg
2030            2035            2040

Pro Gly Val Thr Glu Ala Thr Ile Thr Gly Leu Glu Pro Gly Thr
2045            2050            2055

Glu Tyr Thr Ile Tyr Val Ile Ala Leu Lys Asn Asn Gln Lys Ser
2060            2065            2070

Glu Pro Leu Ile Gly Arg Lys Lys Thr Val Gln Lys Thr Pro Phe
2075            2080            2085

Val Thr His Pro Gly Tyr Asp Thr Gly Asn Gly Ile Gln Leu Pro
2090            2095            2100

Gly Thr Ser Gly Gln Gln Pro Ser Val Gly Gln Gln Met Ile Phe
2105            2110            2115

Glu Glu His Gly Phe Arg Arg Thr Thr Pro Pro Thr Thr Ala Thr
2120            2125            2130

Pro Ile Arg His Arg Pro Arg Pro Tyr Pro Pro Asn Val Gly Gln
2135            2140            2145

Glu Ala Leu Ser Gln Thr Thr Ile Ser Trp Ala Pro Phe Gln Asp
2150            2155            2160

Thr Ser Glu Tyr Ile Ile Ser Cys His Pro Val Gly Thr Asp Glu
2165            2170            2175

Glu Pro Leu Gln Phe Arg Val Pro Gly Thr Ser Thr Ser Ala Thr
2180            2185            2190

Leu Thr Gly Leu Thr Arg Gly Ala Thr Tyr Asn Ile Ile Val Glu
2195            2200            2205

Ala Leu Lys Asp Gln Gln Arg His Lys Val Arg Glu Glu Val Val
2210            2215            2220

Thr Val Gly Asn Ser Val Asn Glu Gly Leu Asn Gln Pro Thr Asp
2225            2230            2235

Asp Ser Cys Phe Asp Pro Tyr Thr Val Ser His Tyr Ala Val Gly
2240            2245            2250

Asp Glu Trp Glu Arg Met Ser Glu Ser Gly Phe Lys Leu Leu Cys
2255            2260            2265

Gln Cys Leu Gly Phe Gly Ser Gly His Phe Arg Cys Asp Ser Ser
2270            2275            2280

Arg Trp Cys His Asp Asn Gly Val Asn Tyr Lys Ile Gly Glu Lys
2285            2290            2295

Trp Asp Arg Gln Gly Glu Asn Gly Gln Met Met Ser Cys Thr Cys
2300            2305            2310

Leu Gly Asn Gly Lys Gly Glu Phe Lys Cys Asp Pro His Glu Ala
2315            2320            2325

Thr Cys Tyr Asp Asp Gly Lys Thr Tyr His Val Gly Glu Gln Trp
2330            2335            2340

Gln Lys Glu Tyr Leu Gly Ala Ile Cys Ser Cys Thr Cys Phe Gly
2345            2350            2355

Gly Gln Arg Gly Trp Arg Cys Asp Asn Cys Arg Arg Pro Gly Gly
2360            2365            2370

Glu Pro Ser Pro Glu Gly Thr Thr Gly Gln Ser Tyr Asn Gln Tyr
2375            2380            2385

-continued

```
Ser Gln Arg Tyr His Gln Arg Thr Asn Thr Asn Val Asn Cys Pro
    2390                2395                2400

Ile Glu Cys Phe Met Pro Leu Asp Val Gln Ala Asp Arg Glu Asp
    2405                2410                2415

Ser Arg Glu
    2420

<210> SEQ ID NO 6
<211> LENGTH: 2296
<212> TYPE: PRT
<213> ORGANISM: Homo sapiens
<220> FEATURE:
<221> NAME/KEY: MISC_FEATURE
<223> OTHER INFORMATION: Fn1 isoform 5 preproprotein

<400> SEQUENCE: 6

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320
```

```
Gln Trp Leu Lys Thr Gln Gly Asn Lys Gln Met Leu Cys Thr Cys Leu
                325                 330                 335
Gly Asn Gly Val Ser Cys Gln Glu Thr Ala Val Thr Gln Thr Tyr Gly
            340                 345                 350
Gly Asn Ser Asn Gly Glu Pro Cys Val Leu Pro Phe Thr Tyr Asn Gly
        355                 360                 365
Arg Thr Phe Tyr Ser Cys Thr Thr Glu Gly Arg Gln Asp Gly His Leu
    370                 375                 380
Trp Cys Ser Thr Thr Ser Asn Tyr Glu Gln Asp Gln Lys Tyr Ser Phe
385                 390                 395                 400
Cys Thr Asp His Thr Val Leu Val Gln Thr Arg Gly Gly Asn Ser Asn
                405                 410                 415
Gly Ala Leu Cys His Phe Pro Phe Leu Tyr Asn Asn His Asn Tyr Thr
            420                 425                 430
Asp Cys Thr Ser Glu Gly Arg Arg Asp Asn Met Lys Trp Cys Gly Thr
        435                 440                 445
Thr Gln Asn Tyr Asp Ala Asp Gln Lys Phe Gly Phe Cys Pro Met Ala
    450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
                485                 490                 495
Thr Cys Val Gly Asn Gly Arg Gly Glu Trp Thr Cys Ile Ala Tyr Ser
            500                 505                 510
Gln Leu Arg Asp Gln Cys Ile Val Asp Asp Ile Thr Tyr Asn Val Asn
        515                 520                 525
Asp Thr Phe His Lys Arg His Glu Glu Gly His Met Leu Asn Cys Thr
    530                 535                 540
Cys Phe Gly Gln Gly Arg Gly Arg Trp Lys Cys Asp Pro Val Asp Gln
545                 550                 555                 560
Cys Gln Asp Ser Glu Thr Gly Thr Phe Tyr Gln Ile Gly Asp Ser Trp
                565                 570                 575
Glu Lys Tyr Val His Gly Val Arg Tyr Gln Cys Tyr Cys Tyr Gly Arg
            580                 585                 590
Gly Ile Gly Glu Trp His Cys Gln Pro Leu Gln Thr Tyr Pro Ser Ser
        595                 600                 605
Ser Gly Pro Val Glu Val Phe Ile Thr Glu Thr Pro Ser Gln Pro Asn
    610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
                645                 650                 655
Ala Thr Ile Pro Gly His Leu Asn Ser Tyr Thr Ile Lys Gly Leu Lys
            660                 665                 670
Pro Gly Val Val Tyr Glu Gly Gln Leu Ile Ser Ile Gln Gln Tyr Gly
        675                 680                 685
His Gln Glu Val Thr Arg Phe Asp Phe Thr Thr Thr Ser Thr Ser Thr
    690                 695                 700
Pro Val Thr Ser Asn Thr Val Thr Gly Glu Thr Thr Pro Phe Ser Pro
705                 710                 715                 720
Leu Val Ala Thr Ser Glu Ser Val Thr Glu Ile Thr Ala Ser Ser Phe
                725                 730                 735
Val Val Ser Trp Val Ser Ala Ser Asp Thr Val Ser Gly Phe Arg Val
```

-continued

```
                    740                 745                 750
Glu Tyr Glu Leu Ser Glu Gly Asp Glu Pro Gln Tyr Leu Asp Leu
            755                 760                 765
Pro Ser Thr Ala Thr Ser Val Asn Ile Pro Asp Leu Leu Pro Gly Arg
770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Pro Asp
                    805                 810                 815
Pro Thr Val Asp Gln Val Asp Asp Thr Ser Ile Val Arg Trp Ser
            820                 825                 830
Arg Pro Gln Ala Pro Ile Thr Gly Tyr Arg Ile Val Tyr Ser Pro Ser
            835                 840                 845
Val Glu Gly Ser Ser Thr Glu Leu Asn Leu Pro Glu Thr Ala Asn Ser
            850                 855                 860
Val Thr Leu Ser Asp Leu Gln Pro Gly Val Gln Tyr Asn Ile Thr Ile
865                 870                 875                 880
Tyr Ala Val Glu Glu Asn Gln Glu Ser Thr Pro Val Val Ile Gln Gln
                    885                 890                 895
Glu Thr Thr Gly Thr Pro Arg Ser Asp Thr Val Pro Ser Pro Arg Asp
                    900                 905                 910
Leu Gln Phe Val Glu Val Thr Asp Val Lys Val Thr Ile Met Trp Thr
            915                 920                 925
Pro Pro Glu Ser Ala Val Thr Gly Tyr Arg Val Asp Val Ile Pro Val
            930                 935                 940
Asn Leu Pro Gly Glu His Gly Gln Arg Leu Pro Ile Ser Arg Asn Thr
945                 950                 955                 960
Phe Ala Glu Val Thr Gly Leu Ser Pro Gly Val Thr Tyr Tyr Phe Lys
                    965                 970                 975
Val Phe Ala Val Ser His Gly Arg Glu Ser Lys Pro Leu Thr Ala Gln
                    980                 985                 990
Gln Thr Thr Lys Leu Asp Ala Pro  Thr Asn Leu Gln Phe Val Asn Glu
            995                 1000                1005
Thr Asp Ser Thr Val Leu Val Arg Trp Thr Pro Pro Arg Ala Gln
    1010                1015                1020
Ile Thr Gly Tyr Arg Leu Thr Val Gly Leu Thr Arg Arg Gly Gln
    1025                1030                1035
Pro Arg Gln Tyr Asn Val Gly Pro Ser Val Ser Lys Tyr Pro Leu
    1040                1045                1050
Arg Asn Leu Gln Pro Ala Ser Glu Tyr Thr Val Ser Leu Val Ala
    1055                1060                1065
Ile Lys Gly Asn Gln Glu Ser Pro Lys Ala Thr Gly Val Phe Thr
    1070                1075                1080
Thr Leu Gln Pro Gly Ser Ser Ile Pro Pro Tyr Asn Thr Glu Val
    1085                1090                1095
Thr Glu Thr Thr Ile Val Ile Thr Trp Thr Pro Ala Pro Arg Ile
    1100                1105                1110
Gly Phe Lys Leu Gly Val Arg Pro Ser Gln Gly Gly Glu Ala Pro
    1115                1120                1125
Arg Glu Val Thr Ser Asp Ser Gly Ser Ile Val Val Ser Gly Leu
    1130                1135                1140
Thr Pro Gly Val Glu Tyr Val Tyr Thr Ile Gln Val Leu Arg Asp
    1145                1150                1155
```

```
Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200

Thr Gly Tyr Arg Ile Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260

Ile Pro Ala Val Pro Pro Thr Asp Leu Arg Phe Thr Asn Ile
    1265                1270                1275

Gly Pro Asp Thr Met Arg Val Thr Trp Ala Pro Pro Ser Ile
    1280                1285                1290

Asp Leu Thr Asn Phe Leu Val Arg Tyr Ser Pro Val Lys Asn Glu
    1295                1300                1305

Glu Asp Val Ala Glu Leu Ser Ile Ser Pro Ser Asp Asn Ala Val
    1310                1315                1320

Val Leu Thr Asn Leu Leu Pro Gly Thr Glu Tyr Val Val Ser Val
    1325                1330                1335

Ser Ser Val Tyr Glu Gln His Glu Ser Thr Pro Leu Arg Gly Arg
    1340                1345                1350

Gln Lys Thr Gly Leu Asp Ser Pro Thr Gly Ile Asp Phe Ser Asp
    1355                1360                1365

Ile Thr Ala Asn Ser Phe Thr Val His Trp Ile Ala Pro Arg Ala
    1370                1375                1380

Thr Ile Thr Gly Tyr Arg Ile Arg His His Pro Glu His Phe Ser
    1385                1390                1395

Gly Arg Pro Arg Glu Asp Arg Val Pro His Ser Arg Asn Ser Ile
    1400                1405                1410

Thr Leu Thr Asn Leu Thr Pro Gly Thr Glu Tyr Val Val Ser Ile
    1415                1420                1425

Val Ala Leu Asn Gly Arg Glu Glu Ser Pro Leu Leu Ile Gly Gln
    1430                1435                1440

Gln Ser Thr Val Ser Asp Val Pro Arg Asp Leu Glu Val Val Ala
    1445                1450                1455

Ala Thr Pro Thr Ser Leu Leu Ile Ser Trp Asp Ala Pro Ala Val
    1460                1465                1470

Thr Val Arg Tyr Tyr Arg Ile Thr Tyr Gly Glu Thr Gly Gly Asn
    1475                1480                1485

Ser Pro Val Gln Glu Phe Thr Val Pro Gly Ser Lys Ser Thr Ala
    1490                1495                1500

Thr Ile Ser Gly Leu Lys Pro Gly Val Asp Tyr Thr Ile Thr Val
    1505                1510                1515

Tyr Ala Val Thr Gly Arg Gly Asp Ser Pro Ala Ser Ser Lys Pro
    1520                1525                1530

Ile Ser Ile Asn Tyr Arg Thr Glu Ile Asp Lys Pro Ser Gln Met
    1535                1540                1545

Gln Val Thr Asp Val Gln Asp Asn Ser Ile Ser Val Lys Trp Leu
    1550                1555                1560
```

```
Pro Ser Ser Ser Pro Val Thr Gly Tyr Arg Val Thr     Thr Thr Pro
    1565            1570                1575

Lys Asn Gly Pro Gly Pro Thr Lys Thr Lys Thr Ala     Gly Pro Asp
    1580            1585                1590

Gln Thr Glu Met Thr Ile Glu Gly Leu Gln Pro Thr     Val Glu Tyr
    1595            1600                1605

Val Val Ser Val Tyr Ala Gln Asn Pro Ser Gly Glu     Ser Gln Pro
    1610            1615                1620

Leu Val Gln Thr Ala Val Thr Thr Ile Pro Ala Pro     Thr Asp Leu
    1625            1630                1635

Lys Phe Thr Gln Val Thr Pro Thr Ser Leu Ser Ala     Gln Trp Thr
    1640            1645                1650

Pro Pro Asn Val Gln Leu Thr Gly Tyr Arg Val Arg     Val Thr Pro
    1655            1660                1665

Lys Glu Lys Thr Gly Pro Met Lys Glu Ile Asn Leu     Ala Pro Asp
    1670            1675                1680

Ser Ser Ser Val Val Ser Gly Leu Met Val Ala Thr     Thr Lys Tyr
    1685            1690                1695

Glu Val Ser Val Tyr Ala Leu Lys Asp Thr Leu Thr     Ser Arg Pro
    1700            1705                1710

Ala Gln Gly Val Val Thr Thr Leu Glu Asn Val Ser     Pro Pro Arg
    1715            1720                1725

Arg Ala Arg Val Thr Asp Ala Thr Glu Thr Thr Ile     Thr Ile Ser
    1730            1735                1740

Trp Arg Thr Lys Thr Glu Thr Ile Thr Gly Phe Gln     Val Asp Ala
    1745            1750                1755

Val Pro Ala Asn Gly Gln Thr Pro Ile Gln Arg Thr     Ile Lys Pro
    1760            1765                1770

Asp Val Arg Ser Tyr Thr Ile Thr Gly Leu Gln Pro     Gly Thr Asp
    1775            1780                1785

Tyr Lys Ile Tyr Leu Tyr Thr Leu Asn Asp Asn Ala     Arg Ser Ser
    1790            1795                1800

Pro Val Val Ile Asp Ala Ser Thr Ala Ile Asp Ala     Pro Ser Asn
    1805            1810                1815

Leu Arg Phe Leu Ala Thr Thr Pro Asn Ser Leu Leu     Val Ser Trp
    1820            1825                1830

Gln Pro Pro Arg Ala Arg Ile Thr Gly Tyr Ile Ile     Lys Tyr Glu
    1835            1840                1845

Lys Pro Gly Ser Pro Pro Arg Glu Val Val Pro Arg     Pro Arg Pro
    1850            1855                1860

Gly Val Thr Glu Ala Thr Ile Thr Gly Leu Glu Pro     Gly Thr Glu
    1865            1870                1875

Tyr Thr Ile Tyr Val Ile Ala Leu Lys Asn Asn Gln     Lys Ser Glu
    1880            1885                1890

Pro Leu Ile Gly Arg Lys Lys Thr Asp Glu Leu Pro     Gln Leu Val
    1895            1900                1905

Thr Leu Pro His Pro Asn Leu His Gly Pro Glu Ile     Leu Asp Val
    1910            1915                1920

Pro Ser Thr Val Gln Lys Thr Pro Phe Val Thr His     Pro Gly Tyr
    1925            1930                1935

Asp Thr Gly Asn Gly Ile Gln Leu Pro Gly Thr Ser     Gly Gln Gln
    1940            1945                1950

Pro Ser Val Gly Gln Gln Met Ile Phe Glu Glu His     Gly Phe Arg
```

```
                1955                1960                1965

Arg Thr Thr Pro Pro Thr Thr Ala Thr Pro Ile Arg His Arg Pro
    1970            1975            1980

Arg Pro Tyr Pro Pro Asn Val Gly Glu Glu Ile Gln Ile Gly His
    1985            1990            1995

Ile Pro Arg Glu Asp Val Asp Tyr His Leu Tyr Pro His Gly Pro
    2000            2005            2010

Gly Leu Asn Pro Asn Ala Ser Thr Gly Gln Glu Ala Leu Ser Gln
    2015            2020            2025

Thr Thr Ile Ser Trp Ala Pro Phe Gln Asp Thr Ser Glu Tyr Ile
    2030            2035            2040

Ile Ser Cys His Pro Val Gly Thr Asp Glu Glu Pro Leu Gln Phe
    2045            2050            2055

Arg Val Pro Gly Thr Ser Thr Ser Ala Thr Leu Thr Gly Leu Thr
    2060            2065            2070

Arg Gly Ala Thr Tyr Asn Ile Ile Val Glu Ala Leu Lys Asp Gln
    2075            2080            2085

Gln Arg His Lys Val Arg Glu Glu Val Val Thr Val Gly Asn Ser
    2090            2095            2100

Val Asn Glu Gly Leu Asn Gln Pro Thr Asp Asp Ser Cys Phe Asp
    2105            2110            2115

Pro Tyr Thr Val Ser His Tyr Ala Val Gly Asp Glu Trp Glu Arg
    2120            2125            2130

Met Ser Glu Ser Gly Phe Lys Leu Leu Cys Gln Cys Leu Gly Phe
    2135            2140            2145

Gly Ser Gly His Phe Arg Cys Asp Ser Ser Arg Trp Cys His Asp
    2150            2155            2160

Asn Gly Val Asn Tyr Lys Ile Gly Glu Lys Trp Asp Arg Gln Gly
    2165            2170            2175

Glu Asn Gly Gln Met Met Ser Cys Thr Cys Leu Gly Asn Gly Lys
    2180            2185            2190

Gly Glu Phe Lys Cys Asp Pro His Glu Ala Thr Cys Tyr Asp Asp
    2195            2200            2205

Gly Lys Thr Tyr His Val Gly Glu Gln Trp Gln Lys Glu Tyr Leu
    2210            2215            2220

Gly Ala Ile Cys Ser Cys Thr Cys Phe Gly Gly Gln Arg Gly Trp
    2225            2230            2235

Arg Cys Asp Asn Cys Arg Arg Pro Gly Gly Glu Pro Ser Pro Glu
    2240            2245            2250

Gly Thr Thr Gly Gln Ser Tyr Asn Gln Tyr Ser Gln Arg Tyr His
    2255            2260            2265

Gln Arg Thr Asn Thr Asn Val Asn Cys Pro Ile Glu Cys Phe Met
    2270            2275            2280

Pro Leu Asp Val Gln Ala Asp Arg Glu Asp Ser Arg Glu
    2285            2290            2295

<210> SEQ ID NO 7
<211> LENGTH: 2330
<212> TYPE: PRT
<213> ORGANISM: Homo sapiens
<220> FEATURE:
<221> NAME/KEY: MISC_FEATURE
<223> OTHER INFORMATION: Fn1 isoform 4 preproprotein

<400> SEQUENCE: 7

Met Leu Arg Gly Pro Gly Pro Gly Leu Leu Leu Leu Ala Val Gln Cys
```

-continued

```
1               5               10              15
Leu Gly Thr Ala Val Pro Ser Thr Gly Ala Ser Lys Ser Lys Arg Gln
                20              25              30

Ala Gln Gln Met Val Gln Pro Gln Ser Pro Val Ala Val Ser Gln Ser
                35              40              45

Lys Pro Gly Cys Tyr Asp Asn Gly Lys His Tyr Gln Ile Asn Gln Gln
50              55              60

Trp Glu Arg Thr Tyr Leu Gly Asn Ala Leu Val Cys Thr Cys Tyr Gly
65              70              75              80

Gly Ser Arg Gly Phe Asn Cys Glu Ser Lys Pro Glu Ala Glu Glu Thr
                85              90              95

Cys Phe Asp Lys Tyr Thr Gly Asn Thr Tyr Arg Val Gly Asp Thr Tyr
                100             105             110

Glu Arg Pro Lys Asp Ser Met Ile Trp Asp Cys Thr Cys Ile Gly Ala
                115             120             125

Gly Arg Gly Arg Ile Ser Cys Thr Ile Ala Asn Arg Cys His Glu Gly
                130             135             140

Gly Gln Ser Tyr Lys Ile Gly Asp Thr Trp Arg Arg Pro His Glu Thr
145             150             155             160

Gly Gly Tyr Met Leu Glu Cys Val Cys Leu Gly Asn Gly Lys Gly Glu
                165             170             175

Trp Thr Cys Lys Pro Ile Ala Glu Lys Cys Phe Asp His Ala Ala Gly
                180             185             190

Thr Ser Tyr Val Val Gly Glu Thr Trp Glu Lys Pro Tyr Gln Gly Trp
                195             200             205

Met Met Val Asp Cys Thr Cys Leu Gly Glu Gly Ser Gly Arg Ile Thr
                210             215             220

Cys Thr Ser Arg Asn Arg Cys Asn Asp Gln Asp Thr Arg Thr Ser Tyr
225             230             235             240

Arg Ile Gly Asp Thr Trp Ser Lys Lys Asp Asn Arg Gly Asn Leu Leu
                245             250             255

Gln Cys Ile Cys Thr Gly Asn Gly Arg Gly Glu Trp Lys Cys Glu Arg
                260             265             270

His Thr Ser Val Gln Thr Thr Ser Ser Gly Ser Gly Pro Phe Thr Asp
                275             280             285

Val Arg Ala Ala Val Tyr Gln Pro Gln Pro His Pro Gln Pro Pro Pro
                290             295             300

Tyr Gly His Cys Val Thr Asp Ser Gly Val Val Tyr Ser Val Gly Met
305             310             315             320

Gln Trp Leu Lys Thr Gln Gly Asn Lys Gln Met Leu Cys Thr Cys Leu
                325             330             335

Gly Asn Gly Val Ser Cys Gln Glu Thr Ala Val Thr Gln Thr Tyr Gly
                340             345             350

Gly Asn Ser Asn Gly Glu Pro Cys Val Leu Pro Phe Thr Tyr Asn Gly
                355             360             365

Arg Thr Phe Tyr Ser Cys Thr Thr Glu Gly Arg Gln Asp Gly His Leu
370             375             380

Trp Cys Ser Thr Thr Ser Asn Tyr Glu Gln Asp Gln Lys Tyr Ser Phe
385             390             395             400

Cys Thr Asp His Thr Val Leu Val Gln Thr Arg Gly Gly Asn Ser Asn
                405             410             415

Gly Ala Leu Cys His Phe Pro Phe Leu Tyr Asn Asn His Asn Tyr Thr
                420             425             430
```

-continued

```
Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
                500                 505                 510

Gln Leu Arg Asp Gln Cys Ile Val Asp Ile Thr Tyr Asn Val Asn
            515                 520                 525

Asp Thr Phe His Lys Arg His Glu Glu Gly His Met Leu Asn Cys Thr
530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
                580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
            610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
                660                 665                 670

Pro Gly Val Val Tyr Glu Gly Gln Leu Ile Ser Ile Gln Gln Tyr Gly
            675                 680                 685

His Gln Glu Val Thr Arg Phe Asp Phe Thr Thr Thr Ser Thr Ser Thr
            690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
                740                 745                 750

Glu Tyr Glu Leu Ser Glu Glu Gly Asp Glu Pro Gln Tyr Leu Asp Leu
            755                 760                 765

Pro Ser Thr Ala Thr Ser Val Asn Ile Pro Asp Leu Leu Pro Gly Arg
770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
                820                 825                 830

Arg Pro Gln Ala Pro Ile Thr Gly Tyr Arg Ile Val Tyr Ser Pro Ser
            835                 840                 845

Val Glu Gly Ser Ser Thr Glu Leu Asn Leu Pro Glu Thr Ala Asn Ser
850                 855                 860
```

```
Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln
1010                1015                1020

Ile Thr Gly Tyr Arg Leu Thr Val Gly Leu Thr Arg Arg Gly Gln
1025                1030                1035

Pro Arg Gln Tyr Asn Val Gly Pro Ser Val Ser Lys Tyr Pro Leu
1040                1045                1050

Arg Asn Leu Gln Pro Ala Ser Glu Tyr Thr Val Ser Leu Val Ala
1055                1060                1065

Ile Lys Gly Asn Gln Glu Ser Pro Lys Ala Thr Gly Val Phe Thr
1070                1075                1080

Thr Leu Gln Pro Gly Ser Ser Ile Pro Pro Tyr Asn Thr Glu Val
1085                1090                1095

Thr Glu Thr Thr Ile Val Ile Thr Trp Thr Pro Ala Pro Arg Ile
1100                1105                1110

Gly Phe Lys Leu Gly Val Arg Pro Ser Gln Gly Gly Glu Ala Pro
1115                1120                1125

Arg Glu Val Thr Ser Asp Ser Gly Ser Ile Val Val Ser Gly Leu
1130                1135                1140

Thr Pro Gly Val Glu Tyr Val Tyr Thr Ile Gln Val Leu Arg Asp
1145                1150                1155

Gly Gln Glu Arg Asp Ala Pro Ile Val Asn Lys Val Val Thr Pro
1160                1165                1170

Leu Ser Pro Pro Thr Asn Leu His Leu Glu Ala Asn Pro Asp Thr
1175                1180                1185

Gly Val Leu Thr Val Ser Trp Glu Arg Ser Thr Thr Pro Asp Ile
1190                1195                1200

Thr Gly Tyr Arg Ile Thr Thr Thr Pro Thr Asn Gly Gln Gln Gly
1205                1210                1215

Asn Ser Leu Glu Glu Val Val His Ala Asp Gln Ser Ser Cys Thr
1220                1225                1230

Phe Asp Asn Leu Ser Pro Gly Leu Glu Tyr Asn Val Ser Val Tyr
1235                1240                1245

Thr Val Lys Asp Asp Lys Glu Ser Val Pro Ile Ser Asp Thr Ile
1250                1255                1260

Ile Pro Ala Val Pro Pro Pro Thr Asp Leu Arg Phe Thr Asn Ile
```

-continued

```
            1265                1270                1275
Gly Pro Asp Thr Met Arg Val Thr Trp Ala Pro Pro Ser Ile
    1280                1285                1290
Asp Leu Thr Asn Phe Leu Val Arg Tyr Ser Pro Val Lys Asn Glu
    1295                1300                1305
Glu Asp Val Ala Glu Leu Ser Ile Ser Pro Ser Asp Asn Ala Val
    1310                1315                1320
Val Leu Thr Asn Leu Leu Pro Gly Thr Glu Tyr Val Val Ser Val
    1325                1330                1335
Ser Ser Val Tyr Glu Gln His Glu Ser Thr Pro Leu Arg Gly Arg
    1340                1345                1350
Gln Lys Thr Gly Leu Asp Ser Pro Thr Gly Ile Asp Phe Ser Asp
    1355                1360                1365
Ile Thr Ala Asn Ser Phe Thr Val His Trp Ile Ala Pro Arg Ala
    1370                1375                1380
Thr Ile Thr Gly Tyr Arg Ile Arg His His Pro Glu His Phe Ser
    1385                1390                1395
Gly Arg Pro Arg Glu Asp Arg Val Pro His Ser Arg Asn Ser Ile
    1400                1405                1410
Thr Leu Thr Asn Leu Thr Pro Gly Thr Glu Tyr Val Val Ser Ile
    1415                1420                1425
Val Ala Leu Asn Gly Arg Glu Glu Ser Pro Leu Leu Ile Gly Gln
    1430                1435                1440
Gln Ser Thr Val Ser Asp Val Pro Arg Asp Leu Glu Val Val Ala
    1445                1450                1455
Ala Thr Pro Thr Ser Leu Leu Ile Ser Trp Asp Ala Pro Ala Val
    1460                1465                1470
Thr Val Arg Tyr Tyr Arg Ile Thr Tyr Gly Glu Thr Gly Gly Asn
    1475                1480                1485
Ser Pro Val Gln Glu Phe Thr Val Pro Gly Ser Lys Ser Thr Ala
    1490                1495                1500
Thr Ile Ser Gly Leu Lys Pro Gly Val Asp Tyr Thr Ile Thr Val
    1505                1510                1515
Tyr Ala Val Thr Gly Arg Gly Asp Ser Pro Ala Ser Ser Lys Pro
    1520                1525                1530
Ile Ser Ile Asn Tyr Arg Thr Glu Ile Asp Lys Pro Ser Gln Met
    1535                1540                1545
Gln Val Thr Asp Val Gln Asp Asn Ser Ile Ser Val Lys Trp Leu
    1550                1555                1560
Pro Ser Ser Ser Pro Val Thr Gly Tyr Arg Val Thr Thr Thr Pro
    1565                1570                1575
Lys Asn Gly Pro Gly Pro Thr Lys Thr Lys Thr Ala Gly Pro Asp
    1580                1585                1590
Gln Thr Glu Met Thr Ile Glu Gly Leu Gln Pro Thr Val Glu Tyr
    1595                1600                1605
Val Val Ser Val Tyr Ala Gln Asn Pro Ser Gly Glu Ser Gln Pro
    1610                1615                1620
Leu Val Gln Thr Ala Val Thr Asn Ile Asp Arg Pro Lys Gly Leu
    1625                1630                1635
Ala Phe Thr Asp Val Asp Val Asp Ser Ile Lys Ile Ala Trp Glu
    1640                1645                1650
Ser Pro Gln Gly Gln Val Ser Arg Tyr Arg Val Thr Tyr Ser Ser
    1655                1660                1665
```

Pro Glu Asp Gly Ile His Glu Leu Phe Pro Ala Pro Asp Gly Glu
1670                    1675                1680

Glu Asp Thr Ala Glu Leu Gln Gly Leu Arg Pro Gly Ser Glu Tyr
1685                    1690                1695

Thr Val Ser Val Val Ala Leu His Asp Asp Met Glu Ser Gln Pro
1700                    1705                1710

Leu Ile Gly Thr Gln Ser Thr Ala Ile Pro Ala Pro Thr Asp Leu
1715                    1720                1725

Lys Phe Thr Gln Val Thr Pro Thr Ser Leu Ser Ala Gln Trp Thr
1730                    1735                1740

Pro Pro Asn Val Gln Leu Thr Gly Tyr Arg Val Arg Val Thr Pro
1745                    1750                1755

Lys Glu Lys Thr Gly Pro Met Lys Glu Ile Asn Leu Ala Pro Asp
1760                    1765                1770

Ser Ser Ser Val Val Val Ser Gly Leu Met Val Ala Thr Lys Tyr
1775                    1780                1785

Glu Val Ser Val Tyr Ala Leu Lys Asp Thr Leu Thr Ser Arg Pro
1790                    1795                1800

Ala Gln Gly Val Val Thr Thr Leu Glu Asn Val Ser Pro Pro Arg
1805                    1810                1815

Arg Ala Arg Val Thr Asp Ala Thr Glu Thr Thr Ile Thr Ile Ser
1820                    1825                1830

Trp Arg Thr Lys Thr Glu Thr Ile Thr Gly Phe Gln Val Asp Ala
1835                    1840                1845

Val Pro Ala Asn Gly Gln Thr Pro Ile Gln Arg Thr Ile Lys Pro
1850                    1855                1860

Asp Val Arg Ser Tyr Thr Ile Thr Gly Leu Gln Pro Gly Thr Asp
1865                    1870                1875

Tyr Lys Ile Tyr Leu Tyr Thr Leu Asn Asp Asn Ala Arg Ser Ser
1880                    1885                1890

Pro Val Val Ile Asp Ala Ser Thr Ala Ile Asp Ala Pro Ser Asn
1895                    1900                1905

Leu Arg Phe Leu Ala Thr Thr Pro Asn Ser Leu Leu Val Ser Trp
1910                    1915                1920

Gln Pro Pro Arg Ala Arg Ile Thr Gly Tyr Ile Ile Lys Tyr Glu
1925                    1930                1935

Lys Pro Gly Ser Pro Pro Arg Glu Val Val Pro Arg Pro Arg Pro
1940                    1945                1950

Gly Val Thr Glu Ala Thr Ile Thr Gly Leu Glu Pro Gly Thr Glu
1955                    1960                1965

Tyr Thr Ile Tyr Val Ile Ala Leu Lys Asn Asn Gln Lys Ser Glu
1970                    1975                1980

Pro Leu Ile Gly Arg Lys Lys Thr Val Gln Lys Thr Pro Phe Val
1985                    1990                1995

Thr His Pro Gly Tyr Asp Thr Gly Asn Gly Ile Gln Leu Pro Gly
2000                    2005                2010

Thr Ser Gly Gln Gln Pro Ser Val Gly Gln Gln Met Ile Phe Glu
2015                    2020                2025

Glu His Gly Phe Arg Arg Thr Thr Pro Pro Thr Thr Ala Thr Pro
2030                    2035                2040

Ile Arg His Arg Pro Arg Pro Tyr Pro Pro Asn Val Gly Gln Glu
2045                    2050                2055

Ala Leu Ser Gln Thr Thr Ile Ser Trp Ala Pro Phe Gln Asp Thr
2060                    2065                2070

```
Ser Glu Tyr Ile Ile Ser Cys His Pro Val Gly Thr Asp Glu Glu
    2075                2080                2085

Pro Leu Gln Phe Arg Val Pro Gly Thr Ser Thr Ser Ala Thr Leu
    2090                2095                2100

Thr Gly Leu Thr Arg Gly Ala Thr Tyr Asn Ile Ile Val Glu Ala
    2105                2110                2115

Leu Lys Asp Gln Gln Arg His Lys Val Arg Glu Glu Val Val Thr
    2120                2125                2130

Val Gly Asn Ser Val Asn Glu Gly Leu Asn Gln Pro Thr Asp Asp
    2135                2140                2145

Ser Cys Phe Asp Pro Tyr Thr Val Ser His Tyr Ala Val Gly Asp
    2150                2155                2160

Glu Trp Glu Arg Met Ser Glu Ser Gly Phe Lys Leu Leu Cys Gln
    2165                2170                2175

Cys Leu Gly Phe Gly Ser Gly His Phe Arg Cys Asp Ser Ser Arg
    2180                2185                2190

Trp Cys His Asp Asn Gly Val Asn Tyr Lys Ile Gly Glu Lys Trp
    2195                2200                2205

Asp Arg Gln Gly Glu Asn Gly Gln Met Met Ser Cys Thr Cys Leu
    2210                2215                2220

Gly Asn Gly Lys Gly Glu Phe Lys Cys Asp Pro His Glu Ala Thr
    2225                2230                2235

Cys Tyr Asp Asp Gly Lys Thr Tyr His Val Gly Glu Gln Trp Gln
    2240                2245                2250

Lys Glu Tyr Leu Gly Ala Ile Cys Ser Cys Thr Cys Phe Gly Gly
    2255                2260                2265

Gln Arg Gly Trp Arg Cys Asp Asn Cys Arg Arg Pro Gly Gly Glu
    2270                2275                2280

Pro Ser Pro Glu Gly Thr Thr Gly Gln Ser Tyr Asn Gln Tyr Ser
    2285                2290                2295

Gln Arg Tyr His Gln Arg Thr Asn Thr Asn Val Asn Cys Pro Ile
    2300                2305                2310

Glu Cys Phe Met Pro Leu Asp Val Gln Ala Asp Arg Glu Asp Ser
    2315                2320                2325

Arg Glu
    2330

<210> SEQ ID NO 8
<211> LENGTH: 2477
<212> TYPE: PRT
<213> ORGANISM: Homo sapiens
<220> FEATURE:
<221> NAME/KEY: MISC_FEATURE
<223> OTHER INFORMATION: Fn1 isoform 1 preproprotein

<400> SEQUENCE: 8

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
        50                  55                  60

Trp Glu Arg Thr Tyr Leu Gly Asn Ala Leu Val Cys Thr Cys Tyr Gly
65                  70                  75                  80
```

```
Gly Ser Arg Gly Phe Asn Cys Glu Ser Lys Pro Glu Ala Glu Thr
                85                  90                  95
Cys Phe Asp Lys Tyr Thr Gly Asn Thr Tyr Arg Val Gly Asp Thr Tyr
                100                 105                 110
Glu Arg Pro Lys Asp Ser Met Ile Trp Asp Cys Thr Cys Ile Gly Ala
                115                 120                 125
Gly Arg Gly Arg Ile Ser Cys Thr Ile Ala Asn Arg Cys His Glu Gly
        130                 135                 140
Gly Gln Ser Tyr Lys Ile Gly Asp Thr Trp Arg Arg Pro His Glu Thr
145                 150                 155                 160
Gly Gly Tyr Met Leu Glu Cys Val Cys Leu Gly Asn Gly Lys Gly Glu
                165                 170                 175
Trp Thr Cys Lys Pro Ile Ala Glu Lys Cys Phe Asp His Ala Ala Gly
                180                 185                 190
Thr Ser Tyr Val Val Gly Glu Thr Trp Glu Lys Pro Tyr Gln Gly Trp
            195                 200                 205
Met Met Val Asp Cys Thr Cys Leu Gly Glu Gly Ser Gly Arg Ile Thr
        210                 215                 220
Cys Thr Ser Arg Asn Arg Cys Asn Asp Gln Asp Thr Arg Thr Ser Tyr
225                 230                 235                 240
Arg Ile Gly Asp Thr Trp Ser Lys Lys Asp Asn Arg Gly Asn Leu Leu
                245                 250                 255
Gln Cys Ile Cys Thr Gly Asn Gly Arg Gly Glu Trp Lys Cys Glu Arg
                260                 265                 270
His Thr Ser Val Gln Thr Thr Ser Ser Gly Ser Gly Pro Phe Thr Asp
            275                 280                 285
Val Arg Ala Ala Val Tyr Gln Pro Gln Pro His Pro Gln Pro Pro
        290                 295                 300
Tyr Gly His Cys Val Thr Asp Ser Gly Val Val Tyr Ser Val Gly Met
305                 310                 315                 320
Gln Trp Leu Lys Thr Gln Gly Asn Lys Gln Met Leu Cys Thr Cys Leu
                325                 330                 335
Gly Asn Gly Val Ser Cys Gln Glu Thr Ala Val Thr Gln Thr Tyr Gly
            340                 345                 350
Gly Asn Ser Asn Gly Glu Pro Cys Val Leu Pro Phe Thr Tyr Asn Gly
            355                 360                 365
Arg Thr Phe Tyr Ser Cys Thr Thr Glu Gly Arg Gln Asp Gly His Leu
        370                 375                 380
Trp Cys Ser Thr Thr Ser Asn Tyr Glu Gln Asp Gln Lys Tyr Ser Phe
385                 390                 395                 400
Cys Thr Asp His Thr Val Leu Val Gln Thr Arg Gly Gly Asn Ser Asn
                405                 410                 415
Gly Ala Leu Cys His Phe Pro Phe Leu Tyr Asn Asn His Asn Tyr Thr
            420                 425                 430
Asp Cys Thr Ser Glu Gly Arg Arg Asp Asn Met Lys Trp Cys Gly Thr
        435                 440                 445
Thr Gln Asn Tyr Asp Ala Asp Gln Lys Phe Gly Phe Cys Pro Met Ala
        450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
                485                 490                 495
Thr Cys Val Gly Asn Gly Arg Gly Glu Trp Thr Cys Ile Ala Tyr Ser
```

```
                500             505             510
Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
            530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
            610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
            675                 680                 685

His Gln Glu Val Thr Arg Phe Asp Phe Thr Thr Ser Thr Ser Thr
690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
                740                 745                 750

Glu Tyr Glu Leu Ser Glu Glu Gly Asp Glu Pro Gln Tyr Leu Asp Leu
            755                 760                 765

Pro Ser Thr Ala Thr Ser Val Asn Ile Pro Asp Leu Leu Pro Gly Arg
            770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
                820                 825                 830

Arg Pro Gln Ala Pro Ile Thr Gly Tyr Arg Ile Val Tyr Ser Pro Ser
            835                 840                 845

Val Glu Gly Ser Ser Thr Glu Leu Asn Leu Pro Glu Thr Ala Asn Ser
            850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
                900                 905                 910

Leu Gln Phe Val Glu Val Thr Asp Val Lys Val Thr Ile Met Trp Thr
            915                 920                 925
```

-continued

```
Pro Pro Glu Ser Ala Val Thr Gly Tyr Arg Val Asp Val Ile Pro Val
930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
                980                 985                 990

Gln Thr Thr Lys Leu Asp Ala Pro  Thr Asn Leu Gln Phe  Val Asn Glu
        995                 1000                1005

Thr Asp  Ser Thr Val Leu  Val Arg Trp Thr Pro  Arg Ala Gln
    1010             1015                1020

Ile Thr  Gly Tyr Arg Leu  Thr Val Gly Leu Thr  Arg Arg Gly Gln
    1025             1030                1035

Pro Arg  Gln Tyr Asn Val  Gly Pro Ser Val Ser  Lys Tyr Pro Leu
    1040             1045                1050

Arg Asn  Leu Gln Pro Ala  Ser Glu Tyr Thr Val  Ser Leu Val Ala
    1055             1060                1065

Ile Lys  Gly Asn Gln Glu  Ser Pro Lys Ala Thr  Gly Val Phe Thr
    1070             1075                1080

Thr Leu  Gln Pro Gly Ser  Ser Ile Pro Pro Tyr  Asn Thr Glu Val
    1085             1090                1095

Thr Glu  Thr Thr Ile Val  Ile Thr Trp Thr Pro  Ala Pro Arg Ile
    1100             1105                1110

Gly Phe  Lys Leu Gly Val  Arg Pro Ser Gln Gly  Gly Glu Ala Pro
    1115             1120                1125

Arg Glu  Val Thr Ser Asp  Ser Gly Ser Ile Val  Val Ser Gly Leu
    1130             1135                1140

Thr Pro  Gly Val Glu Tyr  Val Tyr Thr Ile Gln  Val Leu Arg Asp
    1145             1150                1155

Gly Gln  Glu Arg Asp Ala  Pro Ile Val Asn Lys  Val Val Thr Pro
    1160             1165                1170

Leu Ser  Pro Pro Thr Asn  Leu His Leu Glu Ala  Asn Pro Asp Thr
    1175             1180                1185

Gly Val  Leu Thr Val Ser  Trp Glu Arg Ser Thr  Thr Pro Asp Ile
    1190             1195                1200

Thr Gly  Tyr Arg Ile Thr  Thr Thr Pro Thr Asn  Gly Gln Gln Gly
    1205             1210                1215

Asn Ser  Leu Glu Glu Val  Val His Ala Asp Gln  Ser Ser Cys Thr
    1220             1225                1230

Phe Asp  Asn Leu Ser Pro  Gly Leu Glu Tyr Asn  Val Ser Val Tyr
    1235             1240                1245

Thr Val  Lys Asp Asp Lys  Glu Ser Val Pro Ile  Ser Asp Thr Ile
    1250             1255                1260

Ile Pro  Glu Val Pro Gln  Leu Thr Asp Leu Ser  Phe Val Asp Ile
    1265             1270                1275

Thr Asp  Ser Ser Ile Gly  Leu Arg Trp Thr Pro  Leu Asn Ser Ser
    1280             1285                1290

Thr Ile  Ile Gly Tyr Arg  Ile Thr Val Val Ala  Ala Gly Glu Gly
    1295             1300                1305

Ile Pro  Ile Phe Glu Asp  Phe Val Asp Ser Ser  Val Gly Tyr Tyr
    1310             1315                1320

Thr Val  Thr Gly Leu Glu  Pro Gly Ile Asp Tyr  Asp Ile Ser Val
    1325             1330                1335
```

-continued

```
Ile Thr Leu Ile Asn Gly Gly Glu Ser Ala Pro Thr Thr Leu Thr
    1340                1345                1350

Gln Gln Thr Ala Val Pro Pro Thr Asp Leu Arg Phe Thr Asn
    1355                1360                1365

Ile Gly Pro Asp Thr Met Arg Val Thr Trp Ala Pro Pro Ser
    1370                1375                1380

Ile Asp Leu Thr Asn Phe Leu Val Arg Tyr Ser Pro Val Lys Asn
    1385                1390                1395

Glu Glu Asp Val Ala Glu Leu Ser Ile Ser Pro Ser Asp Asn Ala
    1400                1405                1410

Val Val Leu Thr Asn Leu Leu Pro Gly Thr Glu Tyr Val Val Ser
    1415                1420                1425

Val Ser Ser Val Tyr Glu Gln His Glu Ser Thr Pro Leu Arg Gly
    1430                1435                1440

Arg Gln Lys Thr Gly Leu Asp Ser Pro Thr Gly Ile Asp Phe Ser
    1445                1450                1455

Asp Ile Thr Ala Asn Ser Phe Thr Val His Trp Ile Ala Pro Arg
    1460                1465                1470

Ala Thr Ile Thr Gly Tyr Arg Ile Arg His His Pro Glu His Phe
    1475                1480                1485

Ser Gly Arg Pro Arg Glu Asp Arg Val Pro His Ser Arg Asn Ser
    1490                1495                1500

Ile Thr Leu Thr Asn Leu Thr Pro Gly Thr Glu Tyr Val Val Ser
    1505                1510                1515

Ile Val Ala Leu Asn Gly Arg Glu Glu Ser Pro Leu Leu Ile Gly
    1520                1525                1530

Gln Gln Ser Thr Val Ser Asp Val Pro Arg Asp Leu Glu Val Val
    1535                1540                1545

Ala Ala Thr Pro Thr Ser Leu Leu Ile Ser Trp Asp Ala Pro Ala
    1550                1555                1560

Val Thr Val Arg Tyr Tyr Arg Ile Thr Tyr Gly Glu Thr Gly Gly
    1565                1570                1575

Asn Ser Pro Val Gln Glu Phe Thr Val Pro Gly Ser Lys Ser Thr
    1580                1585                1590

Ala Thr Ile Ser Gly Leu Lys Pro Gly Val Asp Tyr Thr Ile Thr
    1595                1600                1605

Val Tyr Ala Val Thr Gly Arg Gly Asp Ser Pro Ala Ser Ser Lys
    1610                1615                1620

Pro Ile Ser Ile Asn Tyr Arg Thr Glu Ile Asp Lys Pro Ser Gln
    1625                1630                1635

Met Gln Val Thr Asp Val Gln Asp Asn Ser Ile Ser Val Lys Trp
    1640                1645                1650

Leu Pro Ser Ser Ser Pro Val Thr Gly Tyr Arg Val Thr Thr Thr
    1655                1660                1665

Pro Lys Asn Gly Pro Gly Pro Thr Lys Thr Lys Thr Ala Gly Pro
    1670                1675                1680

Asp Gln Thr Glu Met Thr Ile Glu Gly Leu Gln Pro Thr Val Glu
    1685                1690                1695

Tyr Val Val Ser Val Tyr Ala Gln Asn Pro Ser Gly Glu Ser Gln
    1700                1705                1710

Pro Leu Val Gln Thr Ala Val Thr Asn Ile Asp Arg Pro Lys Gly
    1715                1720                1725

Leu Ala Phe Thr Asp Val Asp Val Asp Ser Ile Lys Ile Ala Trp
```

-continued

```
            1730                1735                1740

Glu Ser Pro Gln Gly Gln Val Ser Arg Tyr Arg Val Thr Tyr Ser
    1745                1750                1755

Ser Pro Glu Asp Gly Ile His Glu Leu Phe Pro Ala Pro Asp Gly
    1760                1765                1770

Glu Glu Asp Thr Ala Glu Leu Gln Gly Leu Arg Pro Gly Ser Glu
    1775                1780                1785

Tyr Thr Val Ser Val Val Ala Leu His Asp Asp Met Glu Ser Gln
    1790                1795                1800

Pro Leu Ile Gly Thr Gln Ser Thr Ala Ile Pro Ala Pro Thr Asp
    1805                1810                1815

Leu Lys Phe Thr Gln Val Thr Pro Thr Ser Leu Ser Ala Gln Trp
    1820                1825                1830

Thr Pro Pro Asn Val Gln Leu Thr Gly Tyr Arg Val Arg Val Thr
    1835                1840                1845

Pro Lys Glu Lys Thr Gly Pro Met Lys Glu Ile Asn Leu Ala Pro
    1850                1855                1860

Asp Ser Ser Ser Val Val Ser Gly Leu Met Val Ala Thr Lys
    1865                1870                1875

Tyr Glu Val Ser Val Tyr Ala Leu Lys Asp Thr Leu Thr Ser Arg
    1880                1885                1890

Pro Ala Gln Gly Val Val Thr Thr Leu Glu Asn Val Ser Pro Pro
    1895                1900                1905

Arg Arg Ala Arg Val Thr Asp Ala Thr Glu Thr Thr Ile Thr Ile
    1910                1915                1920

Ser Trp Arg Thr Lys Thr Glu Thr Ile Thr Gly Phe Gln Val Asp
    1925                1930                1935

Ala Val Pro Ala Asn Gly Gln Thr Pro Ile Gln Arg Thr Ile Lys
    1940                1945                1950

Pro Asp Val Arg Ser Tyr Thr Ile Thr Gly Leu Gln Pro Gly Thr
    1955                1960                1965

Asp Tyr Lys Ile Tyr Leu Tyr Thr Leu Asn Asp Asn Ala Arg Ser
    1970                1975                1980

Ser Pro Val Val Ile Asp Ala Ser Thr Ala Ile Asp Ala Pro Ser
    1985                1990                1995

Asn Leu Arg Phe Leu Ala Thr Thr Pro Asn Ser Leu Leu Val Ser
    2000                2005                2010

Trp Gln Pro Pro Arg Ala Arg Ile Thr Gly Tyr Ile Ile Lys Tyr
    2015                2020                2025

Glu Lys Pro Gly Ser Pro Pro Arg Glu Val Val Pro Arg Pro Arg
    2030                2035                2040

Pro Gly Val Thr Glu Ala Thr Ile Thr Gly Leu Glu Pro Gly Thr
    2045                2050                2055

Glu Tyr Thr Ile Tyr Val Ile Ala Leu Lys Asn Asn Gln Lys Ser
    2060                2065                2070

Glu Pro Leu Ile Gly Arg Lys Lys Thr Asp Glu Leu Pro Gln Leu
    2075                2080                2085

Val Thr Leu Pro His Pro Asn Leu His Gly Pro Glu Ile Leu Asp
    2090                2095                2100

Val Pro Ser Thr Val Gln Lys Thr Pro Phe Val Thr His Pro Gly
    2105                2110                2115

Tyr Asp Thr Gly Asn Gly Ile Gln Leu Pro Gly Thr Ser Gly Gln
    2120                2125                2130
```

| | | | | | | | | | | |
|---|---|---|---|---|---|---|---|---|---|---|
| Gln | Pro | Ser | Val | Gly | Gln | Gln | Met | Ile | Phe | Glu | Glu | His | Gly | Phe |
| | 2135 | | | | 2140 | | | | | 2145 | | | | |
| Arg | Arg | Thr | Thr | Pro | Pro | Thr | Thr | Ala | Thr | Pro | Ile | Arg | His | Arg |
| 2150 | | | | | 2155 | | | | | 2160 | | | | |
| Pro | Arg | Pro | Tyr | Pro | Pro | Asn | Val | Gly | Glu | Glu | Ile | Gln | Ile | Gly |
| 2165 | | | | | 2170 | | | | | 2175 | | | | |
| His | Ile | Pro | Arg | Glu | Asp | Val | Asp | Tyr | His | Leu | Tyr | Pro | His | Gly |
| 2180 | | | | | 2185 | | | | | 2190 | | | | |
| Pro | Gly | Leu | Asn | Pro | Asn | Ala | Ser | Thr | Gly | Gln | Glu | Ala | Leu | Ser |
| 2195 | | | | | 2200 | | | | | 2205 | | | | |
| Gln | Thr | Thr | Ile | Ser | Trp | Ala | Pro | Phe | Gln | Asp | Thr | Ser | Glu | Tyr |
| 2210 | | | | | 2215 | | | | | 2220 | | | | |
| Ile | Ile | Ser | Cys | His | Pro | Val | Gly | Thr | Asp | Glu | Glu | Pro | Leu | Gln |
| 2225 | | | | | 2230 | | | | | 2235 | | | | |
| Phe | Arg | Val | Pro | Gly | Thr | Ser | Thr | Ser | Ala | Thr | Leu | Thr | Gly | Leu |
| 2240 | | | | | 2245 | | | | | 2250 | | | | |
| Thr | Arg | Gly | Ala | Thr | Tyr | Asn | Ile | Ile | Val | Glu | Ala | Leu | Lys | Asp |
| 2255 | | | | | 2260 | | | | | 2265 | | | | |
| Gln | Gln | Arg | His | Lys | Val | Arg | Glu | Glu | Val | Val | Thr | Val | Gly | Asn |
| 2270 | | | | | 2275 | | | | | 2280 | | | | |
| Ser | Val | Asn | Glu | Gly | Leu | Asn | Gln | Pro | Thr | Asp | Asp | Ser | Cys | Phe |
| 2285 | | | | | 2290 | | | | | 2295 | | | | |
| Asp | Pro | Tyr | Thr | Val | Ser | His | Tyr | Ala | Val | Gly | Asp | Glu | Trp | Glu |
| 2300 | | | | | 2305 | | | | | 2310 | | | | |
| Arg | Met | Ser | Glu | Ser | Gly | Phe | Lys | Leu | Leu | Cys | Gln | Cys | Leu | Gly |
| 2315 | | | | | 2320 | | | | | 2325 | | | | |
| Phe | Gly | Ser | Gly | His | Phe | Arg | Cys | Asp | Ser | Ser | Arg | Trp | Cys | His |
| 2330 | | | | | 2335 | | | | | 2340 | | | | |
| Asp | Asn | Gly | Val | Asn | Tyr | Lys | Ile | Gly | Glu | Lys | Trp | Asp | Arg | Gln |
| 2345 | | | | | 2350 | | | | | 2355 | | | | |
| Gly | Glu | Asn | Gly | Gln | Met | Met | Ser | Cys | Thr | Cys | Leu | Gly | Asn | Gly |
| 2360 | | | | | 2365 | | | | | 2370 | | | | |
| Lys | Gly | Glu | Phe | Lys | Cys | Asp | Pro | His | Glu | Ala | Thr | Cys | Tyr | Asp |
| 2375 | | | | | 2380 | | | | | 2385 | | | | |
| Asp | Gly | Lys | Thr | Tyr | His | Val | Gly | Glu | Gln | Trp | Gln | Lys | Glu | Tyr |
| 2390 | | | | | 2395 | | | | | 2400 | | | | |
| Leu | Gly | Ala | Ile | Cys | Ser | Cys | Thr | Cys | Phe | Gly | Gly | Gln | Arg | Gly |
| 2405 | | | | | 2410 | | | | | 2415 | | | | |
| Trp | Arg | Cys | Asp | Asn | Cys | Arg | Arg | Pro | Gly | Gly | Glu | Pro | Ser | Pro |
| 2420 | | | | | 2425 | | | | | 2430 | | | | |
| Glu | Gly | Thr | Thr | Gly | Gln | Ser | Tyr | Asn | Gln | Tyr | Ser | Gln | Arg | Tyr |
| 2435 | | | | | 2440 | | | | | 2445 | | | | |
| His | Gln | Arg | Thr | Asn | Thr | Asn | Val | Asn | Cys | Pro | Ile | Glu | Cys | Phe |
| 2450 | | | | | 2455 | | | | | 2460 | | | | |
| Met | Pro | Leu | Asp | Val | Gln | Ala | Asp | Arg | Glu | Asp | Ser | Arg | Glu | |
| 2465 | | | | | 2470 | | | | | 2475 | | | | |

```
<210> SEQ ID NO 9
<211> LENGTH: 2386
<212> TYPE: PRT
<213> ORGANISM: Homo sapiens
<220> FEATURE:
<221> NAME/KEY: MISC_FEATURE
<223> OTHER INFORMATION: largest Fn splice variant

<400> SEQUENCE: 9
```

-continued

```
Met Leu Arg Gly Pro Gly Pro Gly Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
            115                 120                 125

Gly Arg Gly Arg Ile Ser Cys Thr Ile Ala Asn Arg Cys His Glu Gly
        130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
        290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Gln Gly Gly Asn Ser Asn
            405                 410                 415

Gly Ala Leu Cys His Phe Pro Phe Leu Tyr Asn Asn His Asn Tyr Thr
        420                 425                 430
```

```
Asp Cys Thr Ser Glu Gly Arg Arg Asp Asn Met Lys Trp Cys Gly Thr
        435                 440                 445
Thr Gln Asn Tyr Asp Ala Asp Gln Lys Phe Gly Phe Cys Pro Met Ala
450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
                485                 490                 495
Thr Cys Val Gly Asn Gly Arg Gly Glu Trp Thr Cys Ile Ala Tyr Ser
            500                 505                 510
Gln Leu Arg Asp Gln Cys Ile Val Asp Asp Ile Thr Tyr Asn Val Asn
        515                 520                 525
Asp Thr Phe His Lys Arg His Glu Glu Gly His Met Leu Asn Cys Thr
    530                 535                 540
Cys Phe Gly Gln Gly Arg Gly Arg Trp Lys Cys Asp Pro Val Asp Gln
545                 550                 555                 560
Cys Gln Asp Ser Glu Thr Gly Thr Phe Tyr Gln Ile Gly Asp Ser Trp
                565                 570                 575
Glu Lys Tyr Val His Gly Val Arg Tyr Gln Cys Tyr Cys Tyr Gly Arg
            580                 585                 590
Gly Ile Gly Glu Trp His Cys Gln Pro Leu Gln Thr Tyr Pro Ser Ser
        595                 600                 605
Ser Gly Pro Val Glu Val Phe Ile Thr Glu Thr Pro Ser Gln Pro Asn
    610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
                645                 650                 655
Ala Thr Ile Pro Gly His Leu Asn Ser Tyr Thr Ile Lys Gly Leu Lys
            660                 665                 670
Pro Gly Val Val Tyr Glu Gly Gln Leu Ile Ser Ile Gln Gln Tyr Gly
        675                 680                 685
His Gln Glu Val Thr Arg Phe Asp Phe Thr Thr Thr Ser Thr Ser Thr
    690                 695                 700
Pro Val Thr Ser Asn Thr Val Thr Gly Glu Thr Thr Pro Phe Ser Pro
705                 710                 715                 720
Leu Val Ala Thr Ser Glu Ser Val Thr Glu Ile Thr Ala Ser Ser Phe
                725                 730                 735
Val Val Ser Trp Val Ser Ala Ser Asp Thr Val Ser Gly Phe Arg Val
            740                 745                 750
Glu Tyr Glu Leu Ser Glu Glu Gly Asp Glu Pro Gln Tyr Leu Asp Leu
        755                 760                 765
Pro Ser Thr Ala Thr Ser Val Asn Ile Pro Asp Leu Leu Pro Gly Arg
    770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Pro Asp
                805                 810                 815
Pro Thr Val Asp Gln Val Asp Asp Thr Ser Ile Val Val Arg Trp Ser
            820                 825                 830
Arg Pro Gln Ala Pro Ile Thr Gly Tyr Arg Ile Val Tyr Ser Pro Ser
        835                 840                 845
Val Glu Gly Ser Ser Thr Glu Leu Asn Leu Pro Glu Thr Ala Asn Ser
```

-continued

```
            850                 855                 860
Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                    885                 890                 895

Glu Thr Thr Gly Thr Pro Arg Ser Asp Thr Val Pro Ser Pro Arg Asp
                    900                 905                 910

Leu Gln Phe Val Glu Val Thr Asp Val Lys Val Thr Ile Met Trp Thr
            915                 920                 925

Pro Pro Glu Ser Ala Val Thr Gly Tyr Arg Val Asp Val Ile Pro Val
        930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
                980                 985                 990

Gln Thr Thr Lys Leu Asp Ala Pro Thr Asn Leu Gln Phe Val Asn Glu
            995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200

Thr Gly Tyr Arg Ile Thr Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260
```

-continued

| | | | | | | | | | | | |
|---|---|---|---|---|---|---|---|---|---|---|---|
| Ile | Pro | Ala | Val | Pro | Pro | Thr | Asp | Leu | Arg | Phe | Thr | Asn | Ile |
| | 1265 | | | | 1270 | | | | 1275 | | |
| Gly | Pro | Asp | Thr | Met | Arg | Val | Thr | Trp | Ala | Pro | Pro | Ser | Ile |
| | 1280 | | | | 1285 | | | | 1290 | | |
| Asp | Leu | Thr | Asn | Phe | Leu | Val | Arg | Tyr | Ser | Pro | Val | Lys | Asn | Glu |
| | 1295 | | | | 1300 | | | | 1305 | | |
| Glu | Asp | Val | Ala | Glu | Leu | Ser | Ile | Ser | Pro | Ser | Asp | Asn | Ala | Val |
| | 1310 | | | | 1315 | | | | 1320 | | |
| Val | Leu | Thr | Asn | Leu | Leu | Pro | Gly | Thr | Glu | Tyr | Val | Val | Ser | Val |
| | 1325 | | | | 1330 | | | | 1335 | | |
| Ser | Ser | Val | Tyr | Glu | Gln | His | Glu | Ser | Thr | Pro | Leu | Arg | Gly | Arg |
| | 1340 | | | | 1345 | | | | 1350 | | |
| Gln | Lys | Thr | Gly | Leu | Asp | Ser | Pro | Thr | Gly | Ile | Asp | Phe | Ser | Asp |
| | 1355 | | | | 1360 | | | | 1365 | | |
| Ile | Thr | Ala | Asn | Ser | Phe | Thr | Val | His | Trp | Ile | Ala | Pro | Arg | Ala |
| | 1370 | | | | 1375 | | | | 1380 | | |
| Thr | Ile | Thr | Gly | Tyr | Arg | Ile | Arg | His | His | Pro | Glu | His | Phe | Ser |
| | 1385 | | | | 1390 | | | | 1395 | | |
| Gly | Arg | Pro | Arg | Glu | Asp | Arg | Val | Pro | His | Ser | Arg | Asn | Ser | Ile |
| | 1400 | | | | 1405 | | | | 1410 | | |
| Thr | Leu | Thr | Asn | Leu | Thr | Pro | Gly | Thr | Glu | Tyr | Val | Val | Ser | Ile |
| | 1415 | | | | 1420 | | | | 1425 | | |
| Val | Ala | Leu | Asn | Gly | Arg | Glu | Glu | Ser | Pro | Leu | Leu | Ile | Gly | Gln |
| | 1430 | | | | 1435 | | | | 1440 | | |
| Gln | Ser | Thr | Val | Ser | Asp | Val | Pro | Arg | Asp | Leu | Glu | Val | Val | Ala |
| | 1445 | | | | 1450 | | | | 1455 | | |
| Ala | Thr | Pro | Thr | Ser | Leu | Leu | Ile | Ser | Trp | Asp | Ala | Pro | Ala | Val |
| | 1460 | | | | 1465 | | | | 1470 | | |
| Thr | Val | Arg | Tyr | Tyr | Arg | Ile | Thr | Tyr | Gly | Glu | Thr | Gly | Gly | Asn |
| | 1475 | | | | 1480 | | | | 1485 | | |
| Ser | Pro | Val | Gln | Glu | Phe | Thr | Val | Pro | Gly | Ser | Lys | Ser | Thr | Ala |
| | 1490 | | | | 1495 | | | | 1500 | | |
| Thr | Ile | Ser | Gly | Leu | Lys | Pro | Gly | Val | Asp | Tyr | Thr | Ile | Thr | Val |
| | 1505 | | | | 1510 | | | | 1515 | | |
| Tyr | Ala | Val | Thr | Gly | Arg | Gly | Asp | Ser | Pro | Ala | Ser | Ser | Lys | Pro |
| | 1520 | | | | 1525 | | | | 1530 | | |
| Ile | Ser | Ile | Asn | Tyr | Arg | Thr | Glu | Ile | Asp | Lys | Pro | Ser | Gln | Met |
| | 1535 | | | | 1540 | | | | 1545 | | |
| Gln | Val | Thr | Asp | Val | Gln | Asp | Asn | Ser | Ile | Ser | Val | Lys | Trp | Leu |
| | 1550 | | | | 1555 | | | | 1560 | | |
| Pro | Ser | Ser | Ser | Pro | Val | Thr | Gly | Tyr | Arg | Val | Thr | Thr | Thr | Pro |
| | 1565 | | | | 1570 | | | | 1575 | | |
| Lys | Asn | Gly | Pro | Gly | Pro | Thr | Lys | Thr | Lys | Thr | Ala | Gly | Pro | Asp |
| | 1580 | | | | 1585 | | | | 1590 | | |
| Gln | Thr | Glu | Met | Thr | Ile | Glu | Gly | Leu | Gln | Pro | Thr | Val | Glu | Tyr |
| | 1595 | | | | 1600 | | | | 1605 | | |
| Val | Val | Ser | Val | Tyr | Ala | Gln | Asn | Pro | Ser | Gly | Glu | Ser | Gln | Pro |
| | 1610 | | | | 1615 | | | | 1620 | | |
| Leu | Val | Gln | Thr | Ala | Val | Thr | Asn | Ile | Asp | Arg | Pro | Lys | Gly | Leu |
| | 1625 | | | | 1630 | | | | 1635 | | |
| Ala | Phe | Thr | Asp | Val | Asp | Val | Asp | Ser | Ile | Lys | Ile | Ala | Trp | Glu |
| | 1640 | | | | 1645 | | | | 1650 | | |
| Ser | Pro | Gln | Gly | Gln | Val | Ser | Arg | Tyr | Arg | Val | Thr | Tyr | Ser | Ser |
| | 1655 | | | | 1660 | | | | 1665 | | |

```
Pro Glu Asp Gly Ile His Glu Leu Phe Pro Ala Pro Asp Gly Glu
    1670            1675                1680

Glu Asp Thr Ala Glu Leu Gln Gly Leu Arg Pro Gly Ser Glu Tyr
    1685            1690                1695

Thr Val Ser Val Val Ala Leu His Asp Asp Met Glu Ser Gln Pro
    1700            1705                1710

Leu Ile Gly Thr Gln Ser Thr Ala Ile Pro Ala Pro Thr Asp Leu
    1715            1720                1725

Lys Phe Thr Gln Val Thr Pro Thr Ser Leu Ser Ala Gln Trp Thr
    1730            1735                1740

Pro Pro Asn Val Gln Leu Thr Gly Tyr Arg Val Arg Val Thr Pro
    1745            1750                1755

Lys Glu Lys Thr Gly Pro Met Lys Glu Ile Asn Leu Ala Pro Asp
    1760            1765                1770

Ser Ser Ser Val Val Ser Gly Leu Met Val Ala Thr Lys Tyr
    1775            1780                1785

Glu Val Ser Val Tyr Ala Leu Lys Asp Thr Leu Thr Ser Arg Pro
    1790            1795                1800

Ala Gln Gly Val Val Thr Thr Leu Glu Asn Val Ser Pro Pro Arg
    1805            1810                1815

Arg Ala Arg Val Thr Asp Ala Thr Glu Thr Thr Ile Thr Ile Ser
    1820            1825                1830

Trp Arg Thr Lys Thr Glu Thr Ile Thr Gly Phe Gln Val Asp Ala
    1835            1840                1845

Val Pro Ala Asn Gly Gln Thr Pro Ile Gln Arg Thr Ile Lys Pro
    1850            1855                1860

Asp Val Arg Ser Tyr Thr Ile Thr Gly Leu Gln Pro Gly Thr Asp
    1865            1870                1875

Tyr Lys Ile Tyr Leu Tyr Thr Leu Asn Asp Asn Ala Arg Ser Ser
    1880            1885                1890

Pro Val Val Ile Asp Ala Ser Thr Ala Ile Asp Ala Pro Ser Asn
    1895            1900                1905

Leu Arg Phe Leu Ala Thr Thr Pro Asn Ser Leu Leu Val Ser Trp
    1910            1915                1920

Gln Pro Pro Arg Ala Arg Ile Thr Gly Tyr Ile Ile Lys Tyr Glu
    1925            1930                1935

Lys Pro Gly Ser Pro Pro Arg Glu Val Val Pro Arg Pro Arg Pro
    1940            1945                1950

Gly Val Thr Glu Ala Thr Ile Thr Gly Leu Glu Pro Gly Thr Glu
    1955            1960                1965

Tyr Thr Ile Tyr Val Ile Ala Leu Lys Asn Asn Gln Lys Ser Glu
    1970            1975                1980

Pro Leu Ile Gly Arg Lys Lys Thr Asp Glu Leu Pro Gln Leu Val
    1985            1990                1995

Thr Leu Pro His Pro Asn Leu His Gly Pro Glu Ile Leu Asp Val
    2000            2005                2010

Pro Ser Thr Val Gln Lys Thr Pro Phe Val Thr His Pro Gly Tyr
    2015            2020                2025

Asp Thr Gly Asn Gly Ile Gln Leu Pro Gly Thr Ser Gly Gln Gln
    2030            2035                2040

Pro Ser Val Gly Gln Gln Met Ile Phe Glu Glu His Gly Phe Arg
    2045            2050                2055

Arg Thr Thr Pro Pro Thr Thr Ala Thr Pro Ile Arg His Arg Pro
```

```
            2060                2065                2070

Arg Pro Tyr Pro Pro Asn Val Gly Glu Glu Ile Gln Ile Gly His
    2075                2080                2085

Ile Pro Arg Glu Asp Val Asp Tyr His Leu Tyr Pro His Gly Pro
    2090                2095                2100

Gly Leu Asn Pro Asn Ala Ser Thr Gly Gln Glu Ala Leu Ser Gln
    2105                2110                2115

Thr Thr Ile Ser Trp Ala Pro Phe Gln Asp Thr Ser Glu Tyr Ile
    2120                2125                2130

Ile Ser Cys His Pro Val Gly Thr Asp Glu Glu Pro Leu Gln Phe
    2135                2140                2145

Arg Val Pro Gly Thr Ser Thr Ser Ala Thr Leu Thr Gly Leu Thr
    2150                2155                2160

Arg Gly Ala Thr Tyr Asn Ile Ile Val Glu Ala Leu Lys Asp Gln
    2165                2170                2175

Gln Arg His Lys Val Arg Glu Glu Val Val Thr Val Gly Asn Ser
    2180                2185                2190

Val Asn Glu Gly Leu Asn Gln Pro Thr Asp Asp Ser Cys Phe Asp
    2195                2200                2205

Pro Tyr Thr Val Ser His Tyr Ala Val Gly Asp Glu Trp Glu Arg
    2210                2215                2220

Met Ser Glu Ser Gly Phe Lys Leu Leu Cys Gln Cys Leu Gly Phe
    2225                2230                2235

Gly Ser Gly His Phe Arg Cys Asp Ser Ser Arg Trp Cys His Asp
    2240                2245                2250

Asn Gly Val Asn Tyr Lys Ile Gly Glu Lys Trp Asp Arg Gln Gly
    2255                2260                2265

Glu Asn Gly Gln Met Met Ser Cys Thr Cys Leu Gly Asn Gly Lys
    2270                2275                2280

Gly Glu Phe Lys Cys Asp Pro His Glu Ala Thr Cys Tyr Asp Asp
    2285                2290                2295

Gly Lys Thr Tyr His Val Gly Glu Gln Trp Gln Lys Glu Tyr Leu
    2300                2305                2310

Gly Ala Ile Cys Ser Cys Thr Cys Phe Gly Gly Gln Arg Gly Trp
    2315                2320                2325

Arg Cys Asp Asn Cys Arg Arg Pro Gly Gly Glu Pro Ser Pro Glu
    2330                2335                2340

Gly Thr Thr Gly Gln Ser Tyr Asn Gln Tyr Ser Gln Arg Tyr His
    2345                2350                2355

Gln Arg Thr Asn Thr Asn Val Asn Cys Pro Ile Glu Cys Phe Met
    2360                2365                2370

Pro Leu Asp Val Gln Ala Asp Arg Glu Asp Ser Arg Glu
    2375                2380                2385

<210> SEQ ID NO 10
<211> LENGTH: 49
<212> TYPE: PRT
<213> ORGANISM: Streptococcus pyogenes
<220> FEATURE:
<221> NAME/KEY: MISC_FEATURE
<223> OTHER INFORMATION: Functional Upstream Domain (FUD) of F1 adhesion
      protein

<400> SEQUENCE: 10

Lys Asp Gln Ser Pro Leu Ala Gly Glu Ser Gly Glu Thr Glu Tyr Ile
1               5                   10                  15
```

```
Thr Glu Val Tyr Gly Asn Gln Gln Asn Pro Val Asp Ile Asp Lys Lys
            20                  25                  30

Leu Pro Asn Glu Thr Gly Phe Ser Gly Asn Met Val Glu Thr Glu Asp
            35                  40                  45

Thr

<210> SEQ ID NO 11
<211> LENGTH: 7
<212> TYPE: PRT
<213> ORGANISM: Streptococcus pyogenes

<400> SEQUENCE: 11

Met Gly Gly Gln Ser Glu Ser
1               5

<210> SEQ ID NO 12
<211> LENGTH: 44
<212> TYPE: PRT
<213> ORGANISM: Streptococcus pyogenes

<400> SEQUENCE: 12

Met Gly Gly Gln Ser Glu Ser Val Glu Phe Thr Lys Asp Thr Gln Thr
1               5                   10                  15

Gly Met Ser Gly Gln Thr Thr Pro Gln Ile Glu Thr Glu Asp Thr Lys
            20                  25                  30

Glu Pro Gly Val Leu Met Gly Gly Gln Ser Glu Ser
            35                  40

<210> SEQ ID NO 13
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 13

Gly Pro Gln Gly Ile Trp Gly Gln
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 14

Gly Asp Gln Gly Ile Ala Gly Phe
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION

<400> SEQUENCE: 15

Phe Lys Gly Gly Arg Gly Asp Ser Pro Gly
1               5                   10
```

```
-continued

<210> SEQ ID NO 16
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION

<400> SEQUENCE: 16

Phe Lys Gly Gly Gly Lys Phe Ile Thr Cys
1               5                   10
```